(12) United States Patent
Holland et al.

(10) Patent No.: US 7,405,066 B2
(45) Date of Patent: Jul. 29, 2008

(54) BACTERIOPHAGE AND THEIR USES

(75) Inventors: Keith Holland, Yorkshire (GB); Richard Bojar, Yorkshire (GB); David West, Salisbury (GB)

(73) Assignee: The University of Leeds, Yorkshire (GB)

( * ) Notice: Subject to any disclaimer, the term of this patent is extended or adjusted under 35 U.S.C. 154(b) by 0 days.

(21) Appl. No.: 11/483,178

(22) Filed: Jul. 10, 2006

(65) Prior Publication Data

US 2007/0014770 A1 Jan. 18, 2007

(30) Foreign Application Priority Data

Jul. 12, 2005 (GB) ................................ 0514324.3
Dec. 15, 2005 (GB) ................................ 0525552.6

(51) Int. Cl.
*C12N 7/00* (2006.01)
*C07H 21/04* (2006.01)

(52) U.S. Cl. .................................... 435/235.1; 536/23.1

(58) Field of Classification Search ....................... None
See application file for complete search history.

(56) References Cited

U.S. PATENT DOCUMENTS

| 6,121,036 A | 9/2000 | Ghanbari et al. |
| 2004/0241825 A1 | 12/2004 | Mandeville et al. |
| 2005/0032036 A1 | 2/2005 | Weber-Dabrowska et al. |

FOREIGN PATENT DOCUMENTS

| EP | 0 414 304 A3 | 2/1991 |
| WO | WO 01/51066 A2 | 7/2001 |
| WO | WO 01/90366 A2 * | 11/2001 |
| WO | WO 02/07742 A2 | 1/2002 |
| WO | WO 03/080823 A2 | 10/2003 |
| WO | WO 2005/009451 A1 | 2/2005 |

OTHER PUBLICATIONS

Guo et al, Proc Natl Acad Sci 101(25):9205-9210, 2004.*
Webster et al, J. Clin. Microbiology 7(1):84-90, 1978.*
Farrar et al, J. Bacteriology 189(11): 4161-4167, 2007.*
Search Result 1.*
Puhvel, S.M., et al; "Changes in biochemical characterisation of phase sensitive . . . "; V 201; Abstract Annual Meeting Amer. Soc. Microbiology; 72 (1972).
Jong, E.C., et al; "Studies on Bacteriophages of *Propionibacterium acnes*"; *Med. Microbiol. Immunol.*; 161; pp. 263-271 (1975).
Shallta, A.R., et al; "Acne Vulgaris: Pathogenesis and Treatment"; *Cosmetics & Toiletries*; vol. 98; pp. 57-60 (1983).
Mills, O.H., et al; "External Factors Aggravating Acne"; *Dermatologic Clinics*; vol. 1, No. 3; pp. 365-370 (1983).
Summers, W.C.; "Felix d'Herelle and the Origins of Molecular Biology"; Chapter 8, pp. 108-124, 199-200, (1999).
Williamson, P., et al; "A New method for the Quantitative Investigation of Cutaneous Bacteria"; *The Journal of Investigative Dermatology*; vol. 45, No. 5; pp. 498-503 (1965).
Cunliffe, B.; "Diseases of the Skin and their Treatment"; *The Pharmaceutical Journal*; vol. 267; pp. 749-752 (2001).
Besemer, J., et al; "Heuristic approach to deriving models for gene finding"; *Nucleic Acids Research*; vol. 27, No. 19; pp. 3911-3920 (1999).
Vieira, T., et al; (1999); "Viruses as Therapeutic Agents for Treating Bacterial Infections"; *Poster Presentation on Apr. 24, 1999 at the 53rd Annual Eastern Colleges Science Conference*; Sacred Heart University, Fairfield, CT.
Jedrzkiewicz, B., et al; (2000); "Combating the Antibiotic Resistance Crisis: Therapeutic use of Bacteriophages (Viruses) for Treating Acne, A Bacterial Disease"; *Poster Presentation on Apr. 1, 2000 at the 45th Annual Eastern Colleges Science Conference*, Wagner College, Staten Island, NY.
Hany, C., et al; (2001); "The Use of Bacteriophage to Treat Acne, A Bacterial Disease"; *Poster Presentation on Mar. 31, 2001 at the 55th Annual Eastern Colleges Sciences Conference*, Wilkes University, Wilkes-Barre, PA.
Armack, S., et al; (2002); "Bacteriophage Therapy for the Treatment of The Bacterial Disease Acne"; *Poster Presentation on Apr. 27, 2002 at the 56th Annual Eastern Colleges Science Conference*, Niagara University, Niagara, NY.
Aminti, K., et al; Bacteriophage Therapy for The Disease Acne: Identification and Purification of Candidate Bacteriophage; *Poster Presentation on Apr. 12, 2003 at the 57th Annual Eastern Colleges Science Conference*, Ithaca College, Ithaca, NY.
Geronimo, J., et al; "Bacteriophage Therapy for the Skin disease Acne"; *Poster Presentation on Apr. 2, 2004 at the 58th Annual Eastern Colleges Science Conference*, Manhattan College, Riverdale, NY.

* cited by examiner

*Primary Examiner*—Q. Janice Li
*Assistant Examiner*—Kevin K. Hill
(74) *Attorney, Agent, or Firm*—Nixon & Vanderhye

(57) ABSTRACT

There is provided a bacteriophage capable of lysing a *P. acnes* bacterium and incapable of lysing a bacterium which is not *P. acnes*, and which is incapable of sustaining lysogeny in a bacterium. There is also provided a pharmaceutical composition comprising such a bacteriophage.

2 Claims, 7 Drawing Sheets

P.acnes phage 103609

P.acnes phage 1894

Figure 7

```
1894      TCGGGAAACTTATCGTTGTTGTTGTCCCCG---TGCGTGTCGA---------------- 19731
103609    TCGGGAAACTCATCGTTGTTGTTGTCCCCG---TGCATGTCGA---------------- 19752
103672    TCGGGAAACTTATCGTTGTTGTTGTCCCCG---TACATGTCGA---------------- 19703
PA6       TCTGGCAGTGCGCCGTCACCCTGGTTGCTGGTTTGTGTGTCGAAGAGTGTTTTCTGGTTG 19700
              **  ** *      ***     * **   * *    *   ******

1894      -TCAAGTGTTGGGTTTTGGCG--ACCAT-------------CATGTTTCCTATG----- 19769
103609    -TCAAGTGTTGGGTTTTAGTA--ACCAT-------------CATGCCTCCTATG----- 19790
103672    -TCAAGTGTTGGGTTTTAGTA--ACCAT-------------CATGTCTCCTATG----- 19741
PA6       GTGAAATGCTCGGACACGGTGCCATTATGTACGGGTAGTATCCATGTTTTCCATTGTTGT 19760
           * ** ** * **         *    * **            ****  *   * **

1894      TGTGAAAGAGTGTGC------AAATACTATGCAGGTGTCATGG---------------- 19806
103609    TGTGAAAGAGTGTGC------AAATACTATGCAGGTGTCATGG---------------- 19827
103672    TGTGAAAGAGTGTGC------AAATACTATGCTGGTGTCATGG---------------- 19778
PA6       TGTAGCCGGGTGTTCCAGTGGAATTGTTTTGCTGCGTTCGTGGCTTGTTTGATGGTTTTG 19820
          ***    * **** *      **  *  *** *   ** ***

1894      ------------------GTGTTTA-TGCGGGTATGGTTTT--CATCACC----- 19835
103609    ------------------ATGTTTA-TGCGGGTATGGTTTT--CATCACC----- 19856
103672    ------------------ATGTTTA-TGCGGGTATGGTTTT--CATCACC----- 19807
PA6       TAGTAGCCGACGAGGATGCGCTGGTGTTCACTGTCGGGAGGGTTTTGGCCTCGCCAGTAT 19880
                            ****  *  **   **  ****** *  ** **

1894      -------------------TTGCTGAACGT-------------------------- 19846
103609    -------------------TTGCTGAACGT-------------------------- 19867
103672    -------------------TTGCTGAACGT-------------------------- 19818
PA6       TGTGCCGCCACGGCGTAGCGGTTGCTGGCTGTGAAGGCGTCCCAGCAGTATTCAATAATG 19940
                             ******  **

1894      --------------------------CACCTGGTT-------------------- 19855
103609    --------------------------TACTTGGTT-------------------- 19876
103672    --------------------------TACTTGGTT-------------------- 19827
PA6       TGTTGTAGTACACTATCGGGCATGTCTCGTACTTGGTTTTCGTCGAGCCACGCGTCGACA 20000
                                     **  *****

1894      ------------------------------------------------ACTGTA 19861
103609    ------------------------------------------------ACTGTA 19882
103672    ------------------------------------------------ACTGTA 19833
PA6       ATGATGTTGCGTATGGCGCGTTTGTCTTTGGTGGTGGGTTTGAATGCGATGCTCACAGTA 20060
                                                          **  ***

1894      C--------------------ATCATC--------------------------TGGG 19872
103609    C--------------------ATCATC--------------------------TGAG 19893
103672    C--------------------ATCATC--------------------------TGGG 19844
PA6       CGGGCCTGTCGTCTTGCATGAAATCATTAAAGGATGATTCGCTTGCGCGGCGTGCTTGTG 20120
          *                     ****                              **  *

1894      TGATTTCCTGATCCGTTTTGTCGGGGTGCTGCTTTCGCAGGTTCGCCCACTGGCAGGCGT 19932
103609    TGATTTCCTGATCAGTCTTATCGGGGTGCTGCTTTCGCAGGTTCGCCCACTGGCAGGCGT 19953
103672    TGATTTCCTGATCCGTTTTGTCGGGGTGCTGTTTTCGCAGGTTTGCCCATTGGCAGGCGT 19904
PA6       TGATTTGCTGGTCAGACCAGTCGGGGTGTTGCTGTTTCAGATAGTACCAGTGGCACGCAT 20180
          ****** *** **  *    ******** **  *   ***   * *** * **** ** *
```

Figure 8

```
1894      ATCCTTGTGTGGCTAGGGGT------------------------------------- 25946
103609    ATTCGTGTGTGGCTAGGGGT------------------------------------- 25973
103672    TTTCCTGTATGGTTAGATGT------------------------------------- 25942
PA6       TTTCTTGTGTGGCTAGGGGTGATGGCTTCTTTCGCCCAATAGGATGTGCCACCGCTGGTC 26281
            *  *  *** *** ***  **

1894      ------------------------------------------------------------
103609    ------------------------------------------------------------
103672    ------------------------------------------------------------
PA6       CAGTATCCGAGTTTGTTGCGCTGCATGCCCTTGGCGTCCATCTCGTCGATAGTGAGGCAC 26341

1894      ------------------------------------------------------------
103609    ------------------------------------------------------------
103672    ------------------------------------------------------------
PA6       CTGCGGCGATTGGGGCCTGTCTTGACCCCGTGGTCGCCTGTCCGGTGCATGTCGCCTGAG 26401

1894      ------------------------------------------------------------
103609    ------------------------------------------------------------
103672    ------------------------------------------------------------
PA6       GTGGTACTCGTGAATGTTTCATGGCAGATGGTACAGTGCTCTGGTCGATATCCGGTGATT 26461

1894      ------------------------------------------------------------
103609    ------------------------------------------------------------
103672    ------------------------------------------------------------
PA6       GTGCTATCGCACTTGTGGCATGTCCATTCCATGATTGCTCCTATTTTCCATTATAAGACT 26521

1894      ------------------------------------------------------------
103609    ------------------------------------------------------------
103672    ------------------------------------------------------------
PA6       TCCTGTAGTGCCATTTTAGCGCCTTGCGGGTCTTGGGGGTACAACTATATAGGTCAGGTG 26581

1894      -----------------------------------TTTATCGGGCACACAGGGTGA 25967
103609    -----------------------------------TTTATCGGCTGTACAGGGTGA 25994
103672    -----------------------------------TTTATCGGGCACACAGGGTGA 25963
PA6       TTTCTAGGCGATTCTAGGCTCATTGTGTGTGGCTGGGGTTTTATCGGGCACACAGGGTGA 26641
                                             ********  *********
```

BACTERIOPHAGE AND THEIR USES

The invention relates to bacteriophage and their uses. In particular, though not exclusively, it relates to their use in compositions for the treatment of acne.

CROSS-REFERENCE TO RELATED APPLICATIONS

This application claims benefit of UK 0514324.3, filed Jul. 12, 2005 and UK 0525552.6, filed Dec. 15, 2005.

BACKGROUND

Acne vulgaris is one of the most common diseases of the skin and in cases of extreme disfigurement can sometimes have severe consequences for the personality development of young people with ensuing social and economic problems. Adolescents suffering from acne show higher levels of anxiety, greater social inhibition and increased aggression compared to non-acne individuals. Amongst skin diseases, acne is the second highest cause of suicides.

Acne is an exclusively human disease and a unique condition of human sebaceous follicles of the face, chest and back. Spontaneous regression is common, taking about 15 years to complete. However, in about 5 percent of cases, acne persists beyond the age of 25 years and extends into the fourth and fifth decades of life. The earlier the symptoms start, the more severe is the course of the disease. The prevalence of the disease does not reflect any preference for male or female but usually the course is more severe in males.

The onset of the disease in an individual coincides with entry into puberty and is associated with an androgen-driven rise in sebum excretion rate and an increased colonisation of the sebaceous follicles with *Propionibacterium acnes* (*P. acnes*). Recent data indicates that the initiation of individual lesions is primarily inflammatory rather than via keratinocyte hyperproliferation.

Contrary to popular opinion, hygiene and diet have little or no effect on the aetiology of acne. Acne can be exacerbated by external factors such as friction (acne mechanica) (Shalita AR (1983) *Cosmetics and Toiletries* 98: 57-60) and pore-clogging cosmetics (acne cosmetica) (Mills O. H. & Kilgman A.M. (1988) *Dermatol. Clin.* 1: 365-370). The bacterium *P. acnes* is an inhabitant of the human skin and forms a major part of the natural skin flora. There is a wealth of circumstantial evidence implicating *P. acnes* as a major factor in the disease: increased colonisation of the skin by *P. acnes* is associated with the onset of the disease; patients with severe acne are significantly more sensitised to *P. acnes* than normal individuals; the overall immunological status of patients is elevated compared to acne-free individuals of the same age; successful antibiotic treatment reduces the density of *P. acnes* on the skin; and antibiotic therapeutic failure is associated with the presence of antibiotic resistant *P. acnes* on the skin of the patient.

Current treatments for acne focus on various factors contributing to the disease. In summary, anti-comedonal treatments include retinoids and azelaic acid (topical treatments) and isotretinoin (oral treatments); anti-*P.acnes* treatments include benzoyl peroxide, azelaic acid, erythromycin, tetracycline and clindamycin (topical treatments) and tetracycline, erythromycin, minocycline and trimethoprim (oral treatments); anti-inflammatory treatments include tetracycline, erythromycin, clindamycin and nicotinamide (topical treatments) and tetracycline, minocycline, trimethoprim and isotretinoin (oral treatments); and anti-seborrhoeic treatments include spironolactone (topical treatments) and Dianette™ and isotretinoin (oral treatments).

The more common mild and moderate cases of acne are treated with antibiotics, usually topically. There are increasing concerns emerging over the use of antibiotics for acne, where treatments last for long periods of time, up to 2-3 years in some cases. The concerns are two fold. First, the emergence of antibiotic resistant *P. acnes* world-wide with the consequence of reducing their efficacy for acne therapy. Second and possibly more importantly, there is the selection of an increasing pool of antibiotic resistant genes in the commensal microflora, mainly coagulase-negative staphylococci and corynebacteria, on patients' skin. These resistance genes may be horizontally transferred to related species, e.g. *Staphylococcus aureus*, which is a major opportunistic pathogen in the hospital and community environments. Therefore all efforts are required to restrict the use of antibiotics over extended treatment periods as used in the treatment of acne. Obtaining licences to market antibiotic therapies for acne is becoming especially difficult.

Side effects from these treatments are commonplace. Mild irritant dermatitis is associated with virtually all topical therapies (Cunliffe W. J., (2001) *Pharmaceut. J.* 267 749-752). Oral courses of antibiotics have side effects regardless of the condition for which they are prescribed and these often result from their lack of specificity, unbalancing (in due course) much of the bacterial flora in many sites in the body. This leaves room for resistant flora to flourish, resulting in, for example, vaginal candidiasis in women. Retinoid treatment has many side effects: it is a teratogen; causes cheilitis, facial dermatitis and conjunctivitis; leads to secondary skin infections; and has been associated with mood swings and depression. Therefore, there is a need to develop new approaches for acne therapy which specifically target *P. acnes*.

The idea of employing bacteriophage (naturally occurring bacterial viruses) for the treatment or prevention of bacterial diseases was realised relatively soon after the discovery of phage (the words "bacteriophage" and "phage" are used interchangeably throughout this specification) by Felix d'Herelle in 1917. The fact that bacteriophage can specifically infect a bacterial host and rapidly kill it suggested to d'Herelle that this was potentially a very effective way of controlling bacterial infection in man (for review, see "Felix d'Herelle and the Origins of Molecular Biology" William C. Summers (Yale University Press, ISBN 0-300-07127-2)). This potential was never fully realised because of the advent of the antibiotic era, but phage therapy has been pursued since then, in many cases successfully, in former states of the USSR and Eastern Europe.

The emergence of drug resistance and the difficulty in developing novel antibiotics and vaccines has highlighted a growing need to find alternative methods of treatment.

W003/080823 discloses a method for generating candidate bacteriophage for use in therapy by mutating temperate bacteriophage and producing a cocktail of phages. This disclosure specifically selects lysogenic phage, observing that for some bacteria they are more numerous and, therefore, easier to isolate than lytic phage. The phage then have to be mutated to produce lytic vir mutants, in order to avoid the problems associated with lysogenic phage as a therapy, as discussed further below. Treatment of *P. acnes* is mentioned.

EP0414304 relates to the use of bacteriophage to kill bacteria, including *P. acnes*. There is no disclosure of a bacteriophage capable of lysing multiple strains of *P. acnes* bacteria and yet which is incapable of lysing a bacterium which is not *P. acnes* and incapable of sustaining lysogeny in a bacterium.

Jong et al (Med. Microbiol. Immunol. 161 (1975) 263-271) describes isolation of *P. acnes* phage. The paper focuses on the classification of the phage and does not disclose a bacteriophage capable of lysing multiple strains of *P. acnes* bacteria and yet which is incapable of lysing a bacterium which is not *P. acnes* and incapable of sustaining lysogeny in a bacterium.

Puhvel & Reisner (Amer. Soc. Microbiol. 72 (1972) V201) is an abstract relating to the generation of lysogenic phage-resistant strains of *P. acnes*.

WO01/51066 relates to the use of bacteriophage to reduce risk of infection or sepsis, particularly in immunocompromised patients. The disclosed methodology aims to achieve the numerical reduction or elimination of various members of the body's natural bacterial flora, in order to reduce the chance of them causing disease in immunocompromised patients. This is specifically risk reduction rather than cure and is concerned in particular with infections which complicate conditions such as certain cancers, AIDS and cystic fibrosis and which complicate the condition of transplant patients. No mention is made of treatment of *P. acnes*.

U.S. Pat No. 6,121,036 relates to a purified, host specific, non-toxic, wide host range bacteriophage preparation containing at least two phage. The document describes some of the features of an effective phage therapy—that it should be safe, have broad host range and kill a large proportion of bacteria strains—and indicates that such a preparation of appropriate phage could be used to treat *P. acnes* infections. However, no disclosure is made about which phage are suitable for this purpose or that such safe, lytic, broad host range phage exist for *P. acnes*. WO02/07742 purports to disclose a method for potentiating a wider host range for a phage by cloning tail protein-encoding genes from another phage with different host specificity. The document indicates that wide specificity is desirable from a phage therapy point of view but, rather than selecting from naturally occurring phage variants, describes the synthetic construction of a hybrid bacteriophage with dual tail fibre types, therefore having corresponding dual host specificity. This specificity is hypothetically extended to apply the invention in the engineering of a phage which can infect not only different species strains but different bacteria within a species and even within different genera. However, there is no evidence for this potential beyond results showing that a hybrid phage had been created having the ability to infect two different strains of *Escherichia coli*. The application of a suitably modified phage for gene therapy in humans is also contemplated. Specific phage, modified or unmodified, for the treatment of acne are not disclosed. There is no mention of a *P. acnes* bacteriophage with a single host species specificity but with multiple strain specificity.

US2005/0032036 describes a method for sorting through a phage collection and determining the composition of a phage cocktail in order to optimise broad host range infection and lysis, particularly in reference to *Pseudomonas* and *Staphylococcus* strains. No disclosures are made in relation to the field of acne phage therapy.

WO2005/009451 relates in particular to the use of bacteriophage as a part of a combination therapy with traditional, chemical antibiotics, particularly in the treatment of *Pseudomonas aeruginosa* infections and particularly in the treatment of bacteria within biofilms. It describes the difficulty in finding phage with sufficiently broad host specificity to be of therapeutic value for treatment of any given infection and advocates the use of multiple bacteriophage types for therapy, whether simultaneously, separately or sequentially. It also indicates that greater virulence in a phage can be induced artificially by genetic manipulation methods to produce phage with broader specificity or greater infection potential. There is no mention of *P. acnes*, which is not characterised by biofilm formation.

US2004/0241825 discloses several methods for genetically labelling bacteriophage (with a non-functional stretch of DNA that can be detected by, for example, PCR, enabling identification of the phage), identifying non-cross reacting bacteriophage (a multi-step process to isolate phage against the target host and, from these, isolating bacteriophage which do not infect more than 5% of non-pathogenic, non-target hosts) and, finally, a method for selecting phage that are resistant to genetic modification by host bacteria (which involves infecting bacteria with a sample of bacteriophage, isolating progeny phage and comparing the restriction digest patterns of the original bacteriophage and the progeny to identify any differences that would be indicative of genetic modification). Implicit in this disclosure is the difficulty in identifying suitable candidate bacteriophage for use in a therapy. The application of this methodology to *P. acnes* is not described.

Several conference presentations by the research group of Michael Davis at Central Connecticut State University have outlined plans to identify lytic phage having broad host range specificity (Vieira T. and Davis M. A. (1999) Viruses as Therapeutic Agents for Treating Bacterial Infections. Poster presentation on Apr. 24, 1999 at the 53rd Annual Eastern Colleges Science Conference, Sacred Heart University, Fairfield CT; Jedrzkiewicz B. and Davis M. A. (2000) Combating the Antibiotic Resistance Crisis: Therapeutic Use of Bacteriophages (Viruses) for Treating Acne, A Bacterial Disease. Poster presentation on Apr. 1, 2000 at the 54th Annual Eastern Colleges Science Conference, Wagner College, Staten Island N.Y.; Hany C. et al., (2001) The Use of Bacteriophage to Treat Acne, A Bacterial Disease. Poster presentation on Mar. 31, 2001 at the 55th Annual Eastern Colleges Science Conference, Wilkes University, Wilkes-Barre PA; Armack S. et al. (2002) Bacteriophage Therapy For The Treatment Of The Bacterial Disease Acne. Poster presentation on Apr. 27, 2002 at the 56th Annual Eastern Colleges Science Conference, Niagara University, Niagara N.Y.; Aminti K. et al. (2003) Bacteriophage Therapy For The Disease Acne: Identification And Purification Of Candidate Bacteriophage. Poster presentation on Apr. 12, 2003 at the 57th Annual Eastern Colleges Science Conference, Ithaca College, Ithaca N.Y.; Geronimo J. et al (2004) Bacteriophage Therapy For the Skin Disease Acne. Poster presentation on Apr. 2, 2004 at the 58th Annual Eastern Colleges Science Conference, Manhattan College, Riverdale N.Y.). No disclosures have been made in relation to the specific properties of such phage or to specific phage isolates.

DESCRIPTION OF THE INVENTION

According to a first aspect of the invention there is provided a bacteriophage capable of lysing a *P. acnes* bacterium and incapable of lysing any bacterium which is not *P. acnes*, and which is incapable of sustaining lysogeny in a bacterium.

Such a phage has the ability to infect a wide range of bacterial strains within a species but with absolute species specificity. This is one of the most important and usually unachievable aims in the development of an effective phage therapy. In addition, a bacteriophage according to the invention is purely lytic, i.e. incapable of entering the lysogenic phase of the bacteriophage life cycle, a quiescent stage which is undesirable in the creation of an effective therapy and is also unacceptable from a regulatory point of view.

Advantageously, such a bacteriophage can be used in the treatment of acne. No side effects have been reported or are expected in the use of phage therapy, whether delivered systemically, orally or topically. The bacteriophage is specific to *P. acnes* and therefore leaves other members of the skin flora unaffected, reducing the opportunity for the overgrowth of potentially harmful flora. The protective nature of the normal resident microflora is therefore maintained. The specificity of a phage therapy approach to treatment of acne also eliminates the possibility of drug resistance emerging in other members of the microflora: other antibacterial treatments offer a broad brush stroke approach to eliminating bacteria and therefore, under the appropriate conditions, provide an opportunity for developing drug resistance not only in *P. acnes* but in other important commensals with pathogenic potential, e.g. *Staphylococcus aureus*. A further advantage of bacteriophage treatment is that it is self regulating: as the population of host *P. acnes* cells reduces, so will the bacteriophage numbers. In addition, such a bacteriophage can be used as a general prophylactic measure; the use of antibiotics in unprescribed cosmetic products (such as face washes, etc) is undesirable for many reasons relating to safety and the issue of antibiotic resistance. In fact there are strong arguments for limiting the use of antibiotics to reduce the incidence of resistance. Specificity of the bacteriophage means that it is suitable for widespread use in these situations and could be employed as part of a general hygiene routine for the prevention of acne. In addition, the use of the bacteriophage may be effective even against bacterial strains which have become resistant to antibiotics.

As mentioned above, the use of a bacteriophage which can lyse *P. acnes* but is incapable of sustaining lysogeny has the advantage that the bacteriophage cannot lie dormant within a bacterium, but must lyse the bacterium and hence kill it.

Preferably, the bacteriophage lacks the ability to express at least one gene necessary for sustaining lysogeny. The term "lacks the ability to express" is intended to indicate that the bacteriophage lacks the ability to produce a fully functional protein product necessary to sustain lysogeny, for example, as the result of one or more point mutations or full or partial deletions of the genome. More preferably, the phage has a genome which lacks all or part of at least one gene necessary for sustaining lysogeny. Alternatively or additionally, the phage may comprise defects (e.g. mutations, insertions or deletions) in the genome in non-coding regions which may, nonetheless, affect the ability of the phage to sustain lysogeny, for example defects in the genome integration site(s) (e.g. the /latt/site) or in the repressor binding site. The phage is preferably naturally occurring and isolated, with the added advantage that artificial mutations need not be introduced into the bacteriophage. Such mutations, whilst not ruled out, could have potentially unknown results which could be harmful to the individual to whom the bacteriophage is administered. If the phage contains artificial mutations, or is otherwise non-naturally occurring, it is still preferred that the phage is obtained in an isolated state.

In a preferred embodiment, the bacteriophage according to this aspect of the invention is capable of lysing a plurality of strains of the *P. acnes* bacterium. For example, the bacteriophage according to this aspect of the invention may be capable of lysing 5 strains of the *P. acnes* bacterium, preferably at least 10 strains, more preferably at least 16 strains, or at least 17 strains, or at least 18 strains, or at least 19 strains, or at least 20 strains. Most preferably, the bacteriophage is capable of lysing at least 21 strains.

Preferably, the bacteriophage according to this aspect of the invention is isolated and selected from those phage characterised hereinafter as: 103609; 103672; and 1894.

The following isolates of bacteriophage have been deposited under the terms of the Budapest Treaty at The National Collection of Industrial, Marine and Food Bacteria (NCIMB), Ferguson Building, Craibstone Estate, Bucksburn, Aberdeen, AB21 9YA, United Kingdom, under the following accession numbers: Accession no. NCIMB 41332 (isolate PA6); Accession no. NCIMB 41334 (isolate 1874); Accession no. NCIMB 41333 (isolate 1878); Accession no. NCIMB 41335 (isolate 1905); Accession no. NCIMB 41349 (isolate 1894); Accession no. NCIMB 41350 (isolate 103609); Accession no. NCIMB 41351 (isolate 103672). The host bacteria, *P. acnes*, AT1 was also deposited as NCIMB 41336.

The bacteriophage may have a genome which comprises the DNA sequence of SEQ ID NO:3, or a genome having sequence identity of at least 87% with the DNA sequence of SEQ ID NO:3, more preferably sequence identity of at least 88% with that sequence, yet more preferably sequence identity of at least 90% with that sequence, most preferably sequence identity of at least 95%, 96%, 97%, 98% or 99% with that sequence. Alternatively or in addition, the bacteriophage may have a genome comprising a functional fragment of the DNA sequence of SEQ ID NO:3. For example, the functional fragment may be selected from within the Open Reading Frames shown in FIG. 2. Alternatively, the functional fragment may comprise a DNA sequence having sequence identity of at least 95% with the DNA sequence of FIG. 6, preferably sequence identity of at least 96%, more preferably sequence identity of at least 97% with that sequence, most preferably sequence identity of at least 98% or 99% with that sequence. In a preferred embodiment, the functional fragment comprises the DNA sequence of FIG. 6.

Alternatively, the bacteriophage may have a genome which comprises the DNA sequence of SEQ ID NO:4, or a genome having sequence identity of at least 88% with the DNA sequence of SEQ ID NO:4, more preferably sequence identity of at least 89% with that sequence, yet more preferably sequence identity of at least 90% with that sequence, most preferably sequence identity of at least 95%, 96%, 97%, 98% or 99% with that sequence. Alternatively or in addition, the bacteriophage may have a genome comprising a functional fragment of the DNA sequence of SEQ ID NO:4. For example, the functional fragment may be selected from within the Open Reading Frames shown in FIG. 3. Alternatively, the functional fragment may comprise a DNA sequence having sequence identity of at least 95% with the DNA sequence of SEQ ID NO:7, preferably sequence identity of at least 96%, more preferably sequence identity of at least 97% with that sequence, most preferably sequence identity of at least 98% or 99% with that sequence. In a preferred embodiment, the functional fragment comprises the DNA sequence of SEQ ID NO:7.

In a further alternative, the bacteriophage may have a genome which comprises the DNA sequence of SEQ ID NO:5, or a genome having sequence identity of at least 88% with the DNA sequence of SEQ ID NO:5, more preferably sequence identity of at least 89% with that sequence, yet more preferably sequence identity of at least 90% with that sequence, most preferably sequence identity of at least 95%, 96%, 97%, 98% or 99% with that sequence. Alternatively or in addition, the bacteriophage may have a genome comprising a functional fragment of the DNA sequence of SEQ ID NO:5. For example, the functional fragment may be selected from within the Open Reading Frames shown in FIG. 4.

Alternatively, the functional fragment may comprise a DNA sequence having sequence identity of at least 95% with the DNA sequence of SEQ ID NO:8, preferably sequence identity of at least 96%, more preferably sequence identity of at least 97% with that sequence, most preferably sequence identity of at least 98% or 99% with that sequence. In a preferred embodiment, the functional fragment comprises the DNA sequence of SEQ ID NO:8.

Alternatively or additionally, the functional fragment may comprise the DNA sequence of one or more of:

a DNA sequence having sequence identity of at least 63%, 70%, 80%, 90%, 95% or 99% with ORF1 of SEQ ID NO:3, 4 or 5;

a DNA sequence having sequence identity of at least 91%, 95% or 99% with ORF2 of SEQ ID NO:3, 4 or 5;

a DNA sequence having sequence identity of at least 91%, 95% or 99% with ORF3 of SEQ ID NO:3, 4 or 5;

a DNA sequence having sequence identity of at least 91%, 95% or 99% with ORF4 of SEQ ID NO:3, 4 or 5;

a DNA sequence having sequence identity of at least 89%, 90%, 95% or 99% with ORF5 of SEQ ID NO:3, 4 or 5;

a DNA sequence having sequence identity of at least 92%, 95% or 99% with ORF6 of SEQ ID NO:3, 4 or 5;

a DNA sequence having sequence identity of at least 96%, 97%, 98% or 99% with ORF7 of SEQ ID NO:3, 4 or 5;

a DNA sequence having sequence identity of at least 94%, 95% or 99% with ORF8 of SEQ ID NO:3, 4 or 5;

a DNA sequence having sequence identity of at least 95%, 97%, 98% or 99% with ORF9 of SEQ ID NO:3, 4 or 5;

a DNA sequence having sequence identity of at least 91%, 95% or 99% with ORF10 of SEQ ID NO:3, 4 or 5;

a DNA sequence having sequence identity of at least 93%, 95% or 99% with ORF11 of SEQ ID NO:3, 4 or 5;

a DNA sequence having sequence identity of at least 97%, 98% or 99% with ORF12 of SEQ ID NO:3, 4 or 5;

a DNA sequence having sequence identity of at least 99% with ORF13 of SEQ ID NO:3, 4 or 5;

a DNA sequence having sequence identity of at least 91%, 95% or 99% with ORF14 of SEQ ID NO:3, 4 or 5;

a DNA sequence having sequence identity of at least 93%, 95% or 99% with ORF15 of SEQ ID NO:3, 4 or 5;

a DNA sequence having sequence identity of at least 94%, 95% or 99% with ORF16 of SEQ ID NO:3, 4 or 5;

a DNA sequence having sequence identity of at least 97%, 98% or 99% with ORF17 of SEQ ID NO:3, 4 or 5;

a DNA sequence having sequence identity of at least 67%, 70%, 80%, 90%, 95% or 99% with ORF18 of SEQ ID NO:3, 4 or 5;

a DNA sequence having sequence identity of at least 80%, 90%, 95% or 99% with ORF19 of SEQ ID NO:3, 4 or 5;

a DNA sequence having sequence identity of at least 88%, 90%, 95% or 99% with ORF20 of SEQ ID NO:3, 4 or 5;

a DNA sequence having sequence identity of at least 86%, 90%, 95% or 99% with ORF21 of SEQ ID NO:3, 4 or 5;

a DNA sequence having sequence identity of at least 97%, 98% or 99% with ORF22 of SEQ ID NO:3, 4 or 5;

a DNA sequence having sequence identity of at least 98% or 99% with ORF23 of SEQ ID NO:3, 4 or 5;

a DNA sequence having sequence identity of at least 93%, 95% or 99% with ORF24 of SEQ ID NO:3, 4 or 5;

a DNA sequence having sequence identity of at least 87%, 90%, 95% or 99% with ORF25 of SEQ ID NO:3, 4 or 5;

a DNA sequence having sequence identity of at least 63%, 70%, 80%, 90%, 95% or 99% with ORF26 of SEQ ID NO:3, 4 or 5;

a DNA sequence having sequence identity of at least 80%, 90%, 95% or 99% with ORF27 of SEQ ID NO:3, 4 or 5;

a DNA sequence having sequence identity of at least 78%, 80%, 90%, 95% or 99% with ORF28 of SEQ ID NO:3, 4 or 5;

a DNA sequence having sequence identity of at least 66%, 70%, 80%, 90%, 95% or 99% with ORF29 of SEQ ID NO:3, 4 or 5; and/or a DNA sequence having sequence identity of at least 87%, 90%, 95% or 99% with ORF30 of SEQ ID NO:3, 4 or 5.

Preferably, the functional fragment comprises a DNA sequence which is conserved between all of SEQ ID NO:3, 4 and 5.

The bacteriophage may have a genome having sequence identity of at least 88% with the genome of the bacteriophage deposited under Accession No. NCIMB 41349, preferably sequence identity of at least 89%, more preferably sequence identity of at least 90%, most preferably sequence identity of at least 95%, 96%, 97%, 98% or 99%.

The bacteriophage may have a genome having sequence identity of at least 87% with the genome of the bacteriophage deposited under Accession No. NCIMB 41350, preferably sequence identity of at least 88%, more preferably sequence identity of at least 90%, most preferably sequence identity of at least 95%, 96%, 97%, 98% or 99%.

The bacteriophage may have a genome having sequence identity of at least 88% with the genome of the bacteriophage deposited under Accession No. NCIMB 41351, preferably sequence identity of at least 89%, more preferably sequence identity of at least 90%, most preferably sequence identity of at least 95%, 96%, 97%, 98% or 99%.

The term "sequence identity", as used throughout this specification, is calculated as the percentage of nucleotides present in the smaller of the two sequences to be compared that may also be found in the larger of the two sequences, the nucleotides preferably being arranged in the same order in both sequences. The skilled person would readily be able to determine the level of sequence identity between sequences, for example by use of the Blast analysis tool at http://www.ncbi.nlm.nih.gov/BLAST/, using the default parameter settings. Preferably, the length of the shorter of the two sequences being compared is at least 60% of the length of the longer of the two sequences, more preferably at least 70% of the length, yet more preferably at least 80% of the length and still more preferably at least 90%, 95%, 96% 97% 98% or 99% of the length. In a most preferred embodiment, the sequences to be compared are identical in length.

The term "functional fragment", as used throughout this specification, indicates a portion of the full length sequence which has substantially identical functionality to the full length sequence itself. For example, when reference is made to a functional fragment of a bacteriophage genome, this indicates that the fragment, when contained in a bacteriophage, results in a bacteriophage according to the invention, i.e. a bacteriophage capable of lysing a *P. acnes* bacterium and incapable of lysing any bacterium which is not *P. acnes*, and which is incapable of sustaining lysogeny in a bacterium. Preferably, the size of the functional fragment is at least 30% of the size of the full length sequence, more preferably at least 40% of the size, yet more preferably at least 50% of the size, yet more preferably at least 60%, 70%, 80%, 85%, 90% or 95% of the size.

In a preferred embodiment, the bacteriophage has a genome which does not comprise one or more of the nucleotide sequences shown in SEQ ID NO:9, SEQ ID NO:10, SEQ ID NO:11, SEQ ID NO: 12 and SEQ ID NO:13. Without wishing to be bound by theory, it is considered that the properties of a bacteriophage according to the invention, namely that the bacteriophage is capable of lysing a *P. acnes* bacterium, incapable of lysing any bacterium which is not *P. acnes* and incapable of sustaining lysogeny in a bacterium, may be associated with the absence of one or more of these sequences from the genome of the bacteriophage.

Preferably, the bacteriophage is isolated and is selected from those herein characterised as 103609, 103672 and 1894.

The bacteriophage according to the first aspect of the invention may be modified to comprise a marker molecule. The term "marker molecule", as used throughout this specification, is intended to include, but not be limited to, markers or tags such as biotin, a his-tag or a label recognisable by a binding partner such as an antibody, useable, for example, to isolate the bacteriophage. Markers suitable for use in affinity purification processes include glutathione-S-transferase (GST), protein A, ScFv and lectins. Other modifications of the bacteriophage may be made, e.g. for reducing phage antigenicity, including use of a PEG (polyethylene glycol) conjugate or a polysialic acid conjugate. Modifications may also include the addition of molecules which enhance the lethality of the phage to the bacterial host. Examples are given in Westwater C. et al. (2003) *Antimicrob. Agents Chemotherapeutics* 47: 1301-1307. Other suitable markers and modifications will be well known to the skilled person. The marker molecule may be incorporated at the DNA level or may be attached chemically at the phage surface.

According to a second aspect of the invention, there is provided an isolated polynucleotide having the nucleotide sequence of the genome of a bacteriophage according to the first aspect of the invention. Alternatively or additionally, the polynucleotide may comprise the nucleotide sequence of any one of SEQ ID NO:3, SEQ ID NO:4, SEQ ID NO:5 or the complement thereof, or may comprise a functional fragment of the DNA sequence of any one of SEQ ID NO:3, SEQ ID NO:4 or SEQ ID NO:5; when a bacteriophage comprises a polynucleotide according to the second aspect of the invention, it has the properties of a bacteriophage according to the first aspect of the invention.

Preferably, the polynucleotide has sequence identity of at least 87% with the DNA sequence of SEQ ID NO:3, preferably sequence identity of at least 88%, more preferably sequence identity of at least 90%, most preferably sequence identity of at least 95%, 96%, 97%, 98% or 99% with that sequence.

In an alternative preferred embodiment, the polynucleotide has sequence identity of at least 88% with the DNA sequence of SEQ ID NO:4, preferably sequence identity of at least 89%, more preferably sequence identity of at least 90%, most preferably sequence identity of at least 95%, 96%, 97%, 98% or 99% with that sequence.

In a further alternative preferred embodiment, the polynucleotide has sequence identity of at least 88% with the DNA sequence of SEQ ID NO:5, preferably sequence identity of at least 89%, more preferably sequence identity of at least 90%, most preferably sequence identity of at least 95%, 96%, 97%, 98% or 99% with that sequence.

The functional fragment may be selected from one or more of the Open Reading Frames (ORFs) shown in any of FIGS. 2, 3 or 4, i.e. the ORFs within SEQ ID NO:3, 4, or 5 (respectively), the boundaries of which are defined in Table 5 below. Alternatively, the functional fragment may comprise a DNA sequence having sequence identity of at least 95% with any one of the DNA sequences selected from SEQ ID NO:6, SEQ ID NO:7 and SEQ ID NO:8, preferably sequence identity of at least 96%, more preferably sequence identity of at least 97% with any one of those sequences, most preferably sequence identity of at least 98% or 99% with any one of those sequences. In a more preferred embodiment, the functional fragment comprises the DNA sequence of SEQ ID NO:6, SEQ ID NO:7 or SEQ ID NO:8.

Alternatively or additionally, the functional fragment may comprise one or more of:

a DNA sequence having sequence identity of at least 63%, 70%, 80%, 90%, 95% or 99% with ORF1 of SEQ ID NO:3, 4 or 5;

a DNA sequence having sequence identity of at least 91%, 95% or 99% with ORF2 of SEQ ID NO:3, 4 or 5;

a DNA sequence having sequence identity of at least 91%, 95% or 99% with ORF3 of SEQ ID NO:3, 4 or 5;

a DNA sequence having sequence identity of at least 91%, 95% or 99% with ORF4 of SEQ ID NO:3, 4 or 5;

a DNA sequence having sequence identity of at least 89%, 90%, 95% or 99% with ORF5 of SEQ ID NO:3, 4 or 5;

a DNA sequence having sequence identity of at least 92%, 95% or 99% with ORF6 of SEQ ID NO:3, 4 or 5;

a DNA sequence having sequence identity of at least 96%, 97%, 98% or 99% with ORF7 of SEQ ID NO:3, 4 or 5;

a DNA sequence having sequence identity of at least 94%, 95% or 99% with ORF8 of SEQ ID NO:3, 4 or 5;

a DNA sequence having sequence identity of at least 95%, 97%, 98% or 99% with ORF9 of SEQ ID NO:3, 4 or 5;

a DNA sequence having sequence identity of at least 91%, 95% or 99% with ORF10 of SEQ ID NO:3, 4 or 5;

a DNA sequence having sequence identity of at least 93%, 95% or 99% with ORF 11 of SEQ ID NO:3, 4 or 5;

a DNA sequence having sequence identity of at least 97%, 98% or 99% with ORF12 of SEQ ID NO:3, 4 or 5;

a DNA sequence having sequence identity of at least 99% with ORF13 of SEQ ID NO:3, 4 or 5;

a DNA sequence having sequence identity of at least 91%, 95% or 99% with ORF14 of SEQ ID NO:3, 4 or 5;

a DNA sequence having sequence identity of at least 93%, 95% or 99% with ORF15 of SEQ ID NO:3, 4 or 5;

a DNA sequence having sequence identity of at least 94%, 95% or 99% with ORF16 of SEQ ID NO:3, 4 or 5;

a DNA sequence having sequence identity of at least 97%, 98% or 99% with ORF17 of SEQ ID NO:3, 4 or 5;

a DNA sequence having sequence identity of at least 67%, 70%, 80%, 90%, 95% or 99% with ORF18 of SEQ ID NO:3, 4 or 5;

a DNA sequence having sequence identity of at least 80%, 90%, 95% or 99% with ORF19 of SEQ ID NO:3, 4 or 5;

a DNA sequence having sequence identity of at least 88%, 90%, 95% or 99% with ORF20 of SEQ ID NO:3, 4 or 5;

a DNA sequence having sequence identity of at least 86%, 90%, 95% or 99% with ORF21 of SEQ ID NO:3, 4 or 5;

a DNA sequence having sequence identity of at least 97%, 98% or 99% with ORF22 of SEQ ID NO:3, 4 or 5;

a DNA sequence having sequence identity of at least 98% or 99% with ORF23 of SEQ ID NO:3, 4 or 5;

a DNA sequence having sequence identity of at least 93%, 95% or 99% with ORF24 of SEQ ID NO:3, 4 or 5;

a DNA sequence having sequence identity of at least 87%, 90%, 95% or 99% with ORF25 of SEQ ID NO:3, 4 or 5;

a DNA sequence having sequence identity of at least 63%, 70%, 80%, 90%, 95% or 99% with ORF26 of SEQ ID NO:3, 4 or 5;

a DNA sequence having sequence identity of at least 80%, 90%, 95% or 99% with ORF27 of SEQ ID NO:3, 4 or 5;

a DNA sequence having sequence identity of at least 78%, 80%, 90%, 95% or 99% with ORF28 of SEQ ID NO:3, 4 or 5;

a DNA sequence having sequence identity of at least 66%, 70%, 80%, 90%, 95% or 99% with ORF29 of SEQ ID NO:3, 4 or 5; and/or a DNA sequence having sequence identity of at least 87%, 90%, 95% or 99% with ORF30 of SEQ ID NO:3, 4 or 5.

The polynucleotide may comprise one or more of the Open Reading Frames shown in any of FIGS. 2, 3 or 4.

Preferably, the polynucleotide has a nucleic acid sequence which does not comprise one or more of the sequences shown in SEQ ID NO:9. SEQ ID NO:10, SEQ ID NO:11, SEQ ID NO: 12 and SEQ ID NO:13. Without wishing to be bound by theory, it is considered that the properties of a bacteriophage containing a polynucleotide according to the second aspect of the invention, namely that the bacteriophage is capable of lysing a *P. acnes* bacterium, incapable of lysing any bacterium which is not *P. acnes* and incapable of sustaining lysogeny in a bacterium, may be associated with the absence of one or more of these sequences from the polynucleotide according to the second aspect of the invention.

The polynucleotide may further comprise a nucleotide sequence encoding a marker molecule.

According to a third aspect of the invention there is provided an isolated polypeptide having an amino acid sequence encoded by the polynucleotide according to the second aspect of the invention.

According to a fourth aspect of the invention, there is provided a composition comprising at least one bacteriophage according to the first aspect of the invention and an adjuvant, carrier or vehicle.

Preferably, the composition is for use in the prevention or treatment of acne, or for use to improve the appearance of a mammal (preferably a human), the bacteriophage being present in an effective amount.

The term "treatment" (and equivalent terms such as "treating", "treat" etc), as used throughout this specification, is intended to indicate the reduction or elimination of the occurrence of the symptoms of acne. For example, symptoms include visible marks on the face such as papules (small raised red spots less than 5 mm in diameter), superficial pustules and deeper lesions (nodules and pustules larger than 5 mm in diameter). The deeper lesions can lead to scarring.

The composition preferably comprises two or more different isolates of bacteriophage. Each of the two or more isolates of bacteriophage may be a bacteriophage according to the first aspect of the invention.

Additionally or alternatively, the composition may comprise an isolated polynucleotide according to the second aspect of the invention or an isolated polypeptide according to the third aspect of the invention. Where the composition is for use in the prevention or treatment of acne, or for use to improve the appearance of a mammal (preferably a human), the isolated polynucleotide and/or isolated polypeptide is present in an effective amount.

The composition may be in a form suitable for oral, intravenous or topical administration. For example, the composition may be in a form suitable for oral administration and be a liquid, powder or tablet. Alternatively, the composition may be in a form suitable for intravenous administration and be a liquid, or a solid dissolvable in a liquid. In a further alternative, the composition may be in a form suitable for topical administration and be in the form of a cream, solution, powder, spray, aerosol, capsule, solid or gel, or may be bonded to a solid surface. The composition may also form part of a face wash, soap, application stick, cosmetic or dressing.

The bacteriophage, polynucleotide or polypeptide according to the invention contained in the composition may be within, or a part of, liposomes, capsules, carrier particles or, indeed, any other method of maintaining the bacteriophage, polynucleotide or polypeptide in a separate microenvironment within the composition. Alternatively, the bacteriophage, polynucleotide or polypeptide may be added directly to the composition, for example a bacteriophage may be added in a freeze-dried form.

The composition according to this aspect of the invention may further comprise at least one further agent selected from antibiotics, anti-comedonals, anti-*P. acnes*agents, anti-inflammatories and anti-seborrhoeics.

The composition may be a pharmaceutical composition or a cosmetic composition.

According to a fifth aspect of the invention, there is provided a method of preventing or treating acne comprising administering an effective amount of at least one bacteriophage according to the first aspect of the invention and/or of an isolated polynucleotide according to the second aspect of the invention and/or of an isolated polypeptide according to the third aspect of the invention and/or of a composition according to the fourth aspect of the invention to an individual in need of such prevention or treatment.

According to a sixth aspect of the invention, there is provided a method of improving the appearance of an individual, the method comprising administering to the individual an effective amount of a bacteriophage according to the first aspect of the invention and/or of an isolated polynucleotide according to the second aspect of the invention and/or of an isolated polypeptide according to the third aspect of the invention and/or of a composition according to the fourth aspect of the invention.

Preferably, the individual is a human individual. The method is a non-therapeutic cosmetic method.

According to a seventh aspect of the invention, there is provided a method for isolating a bacteriophage capable of lysing a *P. acnes* bacterium, incapable of lysing any bacterium which is not *P. acnes* and incapable of sustaining lysogeny in a bacterium, comprising:
  a) obtaining a sample of bacteria from a skin surface:
  b) isolating from the sample bacteriophage which lyse *propionibacteria;*
  c) isolating the bacteriophage to determine if it is capable of lysing at least one *P. acnes* strain;
  d) testing the bacteriophage to determine if it is capable of lysing non-*P. acnes* bacterial strains;
  e) testing the bacteriophage to determine whether it is capable of sustaining lysogeny in a *P. acnes* strain;
  f) detecting a bacteriophage which has been shown in steps (c), (d) and (e) to be capable of lysing a *P. acnes* bacterium, incapable of lysing any bacterium which is not *P. acnes*, and incapable of sustaining lysogeny in a bacterium.

According to an eighth aspect of the invention, there is provided a method for identifying a bacteriophage which is capable of lysing a *P. acnes* bacterium, incapable of lysing any bacterium which is not *P. acnes* and incapable of sustaining lysogeny in a bacterium, comprising:
  a) exposing a *P. acnes* bacterium to the bacteriophage and determining that the bacterium is lysed;
  b) exposing at least one species of bacteria which is not *P. acnes* bacteria to the bacteriophage and determining that the bacteria are not lysed;
  c) determining that the bacteriophage is not capable of sustaining lysogeny in a bacteria.

Preferably, in step (b), at least three species of bacteria which are not *P. acnes* are exposed to the bacteriophage, more preferably at least four, at least five, at least 10, at least 20, at least 30, at least 40, or at least 50 different strains of bacteria.

According to a ninth aspect of the invention, there is provided a bacteriophage isolated or identified using the method according to the seventh or eighth aspects of the invention.

According to a tenth aspect of the invention, there is provided a bacteriophage obtainable or identifiable by using a method according to the seventh or eighth aspects of the invention.

Embodiments of the invention will now be described, by way of example only, with reference to the accompanying FIGS. 1-8 in which:

FIG. 7 shows an alignment of a portion of the DNA sequences of bacteriophage strains 103609 (SEQ ID NO:3), 103672 (SEQ ID NO:4), 1894 (SEQ ID NO:5) and PA6 (SEQ ID NO: 1).

FIG. 8 shows an alignment of a further portion of the DNA sequences of bacteriophage strains 103609 (SEQ ID NO:3), 103672 (SEQ ID NO:4), 1894 (SEQ ID NO:5) and PA6 (SEQ ID NO:1).

EXPERIMENTAL MATERIALS AND METHODS

1. Materials

Figure 1:
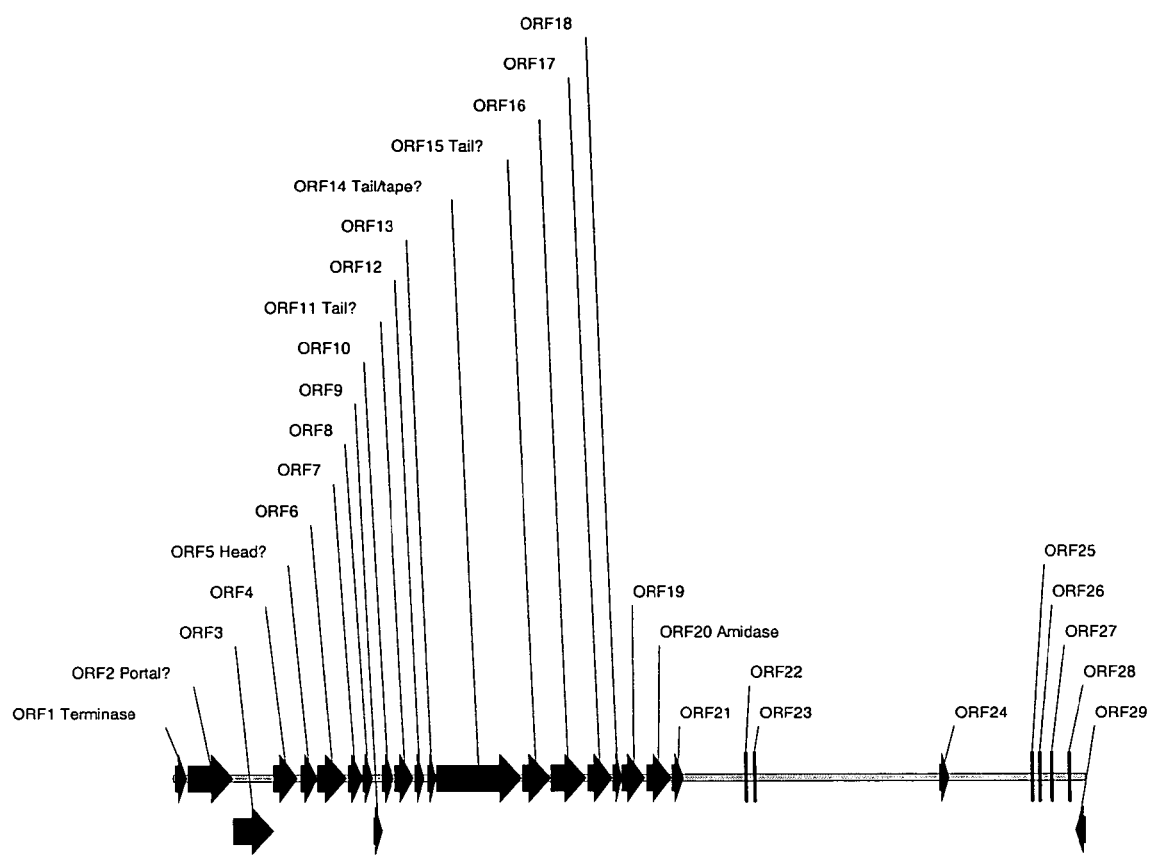
FIG. 1 shows the arrangement of open reading frames (ORFs) in the PA6 genome, with putative functions of various ORFs indicated.

Reinforced Clostridial Agar (RCA; Oxoid CM0151 (Oxoid Ltd., Basingstoke, UK))

TYG broth (1% (w/v) tryptone (Oxoid L42); 0.5% (w/v) yeast extract (Oxoid L21); 0.25% (w/v) glucose)

Top agarose (0.7g low-melting agarose added to 100 ml $dH_2O$, heated to melt, cooled to 45° C., dispensed into 3 ml volumes and autoclaved.)

SM buffer (2.92 g NaCl; 1 g $MgSO_4.7H_2O$; 25 ml 1M Tris-Cl pH7.5; 0.05 g Gelatin; Dissolved in 500 ml $dH_2O$ and autoclaved.)

2. Bacteriophage and Bacteria Collection 2.1 Sampling Method

The strains of *P. acnes* and phage isolates used in the screening were obtained from patients attending the Dermatology Department at the Leeds General Infirmary (except *P. acnes* NCTC737 and DSM16379). The method is based on that described in Williamson P. & Kligman A. M. (1965) *J. Invest. Dennatol.* 45: 498-503.

a) Place a sterile metal ring onto the surface of the skin and press to ensure a good seal;
   b) Pipette 1 ml wash fluid (75 mM phosphate buffer, pH7.9) into the ring;
   c) Gently scrub the surface of the skin for 1 min with a sterile Teflon rod;
   d) Remove the wash fluid to a sterile bottle and replace with another 1 ml of sterile wash fluid;
   e) Repeat scrubbing procedure then remove the fluid and pool with the first sample;
   f) Plate serial dilutions (or spiral plate) of the sample onto RCA containing 6 µg $ml^{-1}$ furazolidone (which inhibits growth of *staphylococci* but not of *propionibacteria*) and incubate anaerobically for 7 days at 34° C.;
   g) Recover individual bacterial colonies or bacteriophage plaques (using method 2.2 described below) and propagate by restreak (bacteria) or the method described below ('Preparation of phage stocks—lysate') for bacteriophage plaque.

2.2 Preparation of Phage Stocks—Plaque Pick
   a) Plate out phage-containing bacteria as described above and incubate for 24-48 h;
   b) Pick 2-3 plugs of agar from a single plaque into 1 ml SM buffer in a screw-top vial using a glass Pasteur pipette;
   c) Store at 4° C.

2.3 Preparation of Phage Stocks—Lysate
   a) Plate out phage-containing bacteria as described above and incubate for 24-48 h;
   b) Overlay plate with 5 ml SM buffer and leave for 1 h at room temperature with occasional swirling;
   c) Pipette buffer into a sterile tube (plastic universal or Falcon) then scrape top agarose off the plate into the tube;
   d) Centrifuge at >5000 rpm for 10 min at 4° C.;
   e) Remove supernatant and filter sterilise (0.2 µm filter);
   f) Aliquot and store at 4° C.

3. Host Range Testing 3.1 Plating of *P. acnes* Bacteriophage
   a) Melt top agarose in a 70° C. water bath then cool to 44° C.;
   b) Centrifuge cultures of *P. acnes* at 5000 rpm for 10 min in a bench-top centrifuge;
   c) Resuspend cells to an $OD_{600}$ of 2.5 in SM buffer;
   d) Add 100 µl of *P. acnes* to an aliquot of phage (usually 5-10 µl) in a microcentrifuge tube, briefly mix and then incubate at 34° C. for 15 min;
   e) Gently pipette the *P. acnes*/phage mixture into 3 ml top agarose and invert to mix;
   f) Pour onto a dry RCA plate and swirl to cover surface;
   g) Allow to set and incubate anaerobically at 34° C. for 24-48 h.

3.2 *P. acnes* Bacteriophage Infectivity Assay
   a) Melt top agarose in a 70° C. water bath then cool to 44° C.;
   b) Centrifuge cultures of *P. acnes* at 5000 rpm for 10 min in a bench-top centrifuge;
   c) Resuspend cells to an $OD_{600}$ of 2.5 in SM buffer;
   d) Add 100 µl of *P. acnes* to 3 ml top agarose and shake to mix;
   e) Pour onto a dry RCA plate and swirl to cover surface;
   f) Allow agarose to set then dry plate again for 15-20 min;
   g) Spot 5 µl of each phage onto the plate;
   h) Allow spots to soak in and incubate anaerobically at 34° C. for 48 h.

For high throughput screening of phage a multipoint inoculator can be used to apply phage spots to the surface of the plate.

3.3 Infectivity Assay of Bacteriophage Against Other Non-*P. acnes* Species

The bacteriophage strains were also tested against other species of bacteria, using the method outlined above but substituting other species for *P. acnes*. The species of bacteria tested were *Propionibacterium granulosum*, *Propionibacterium avidum*, *Staphylococcus epidermidis* and *Corynebacterium bovis*.

3.4 Infectivity Assay of Bacteriophage 103672 on *P. acnes* Immediately After Isolation From Skin of a Volunteer Natural *P. acnes* numbers on the volunteer's back were known to be approximately $10^6$ cfu $cm^{-2}$ ("cfu" denotes "colony forming units"). A scrub wash sample was taken from the back of the volunteer as set out in Method 2.1 above. A small aliquot was taken to determine the starting *P. acnes* count ($10^5$ cfu $cm^{-2}$). The rest of the sample was diluted 1:2 in 2×TYG broth (1×final TYG concentration) in order to grow the *P. acnes*. This was then further diluted in TYG to give 10-fold dilutions ranging from neat to $10^{-3}$. Two samples of each dilution were aliquoted, phage 103672 added to one ($10^6$ pfu $ml^{-1}$ final concentration, "pfu" denoting "plaque forming units") at a ratio of 6:1 phage:cell and SM added to the other as a control. These were then incubated anaerobically at 34° C. for 48 h.

Following incubation, each sample was diluted 10-fold from neat to $10^{-2}$, filtered and treated with 10 mM ferrous ammonium sulphate (FAS), a compound which can inactivate free phage and which, in this context, is used to prevent carry-over of free phage, which could give a false positive result. Filters were plated on RCA+furazolidone plates (RCAF) and incubated anaerobically at 34° C. for 6 days. At the end of this period, the number of colony forming units for $cm^3$ was determined, by counting the number of colonies on the filter and using this figure to calculate the cfu in the original, undiluted, sample.

4. Identification of Non-lysogenic *P. acnes* Bacteriophage

Bacteriophage were subjected to lysogeny and super-infection immunity testing as follows. Phage were spotted onto lawns of *P. acnes* AT1 to produce plaques and these were incubated for periods of time sufficient to allow growth of bacteria within plaques, such bacteria having developed resistance to phage infection. Resistance can develop through changes on the surface of the bacterial cell (e.g. receptor) or internally (e.g. restriction enzymes). However, lysogeny confers resistance to related phages in a process called "superinfection immunity". Repressor protein, expressed by the lysogen, prevents the integrated phage from synthesising the proteins necessary for reproduction. Repressor protein fulfils exactly the same function upon any homologous phage DNA coming into the cell, similarly preventing the production of phage. This can only happen if the incoming DNA is related to the lysogen such that the repressor can bind.

The centres of the turbid plaques were picked and streaked out to obtain single colonies of bacteria apparently resistant to infection by the phage, which may or may not have been lysogenic. At this stage, there was no way of knowing which mechanism of resistance, discussed above, had been acquired. Single colonies were picked and grown in tryptone/yeast extract/glucose (TYG) broth before plating as lawns in top agarose on reinforced clostridial agar (RCA) plates. First, spontaneous plaque formation was identified, indicating phage lysogeny as the result of earlier infection with a lysogenic phage. Second, phage were spotted onto the lawns to look for super-infection immunity to the same or other phage, an indication of lysogeny and/or resistance, since a plaque will form unless the bacteria are immune to infection by the particular phage. As outlined above, if they are immune to repeat infection by the same phage isolate, this suggests the presence of that phage in lysogenic phase in the cell. Similarly, if they are immune to infection by another phage isolate, this suggests the presence of the first phage in lysogenic phase in the cell. Phage which do not display such lysogenic qualities are considered to be suitable for use in embodiments of the invention.

Alternative methods of identifying whether a phage can become lysogenic are PCR detection using primers specific to, for example, the phage repressor DNA, where a positive PCR result would indicate the presence of phage repressor DNA and, therefore, that the bacteriophage in question had the ability to become lysogenic. Absence of a repressor gene is one way of avoiding lysogeny, but other deletions which would convert a lysogenic phage into a lytic phage would include any that removes other parts of the integration machinery, i.e. phage-encoded integrase proteins and DNA sequences required for insertion into host DNA (att sites). Any sort of error which inactivates these genes or sites will achieve the desired lytic phage phenotype, such as entire or partial removal of the gene/site and functionally inactivating point mutation(s). Alternatively, a PCR-based method could detect the ligated cos site in cells which have been exposed to a bacteriophage of interest. Another method would be Southern blotting using labelled phage DNA to probe lysogens in the bacterial genome. These and other such methods are easily within the ability of the skilled person, who would clearly understand how to approach such methods in order to reliably identify whether a phage can become lysogenic and whether, therefore, it falls within the scope of the present invention.

5. DNA Sequencing

Bacteriophage DNA was extracted and purified using the following method:

a) Prepare a plate lysate of the phage (10 ml)
b) Add NaCl to 1 M and PEG8000 to 10% (w/v) and dissolve slowly
c) Incubate on ice for 30 min to allow phage to precipitate
d) Harvest phage by centrifuging at 10,000 g for 10 min at 4° C.
e) Resuspend in 1 ml SM buffer
f) Add an equal volume of chloroform and vortex for 30 sec
g) Centrifuge at 3000 g for 15 min at 4° C.
h) Remove the upper layer containing phage to a sterile tube
i) Add proteinase K to 50 µml$^{-1}$ and SDS to 0.5% (w/v) and incubate at 56° C. for 1 hour
j) Cool, then extract twice with phenol:chloroform and once with chloroform
k) Precipitate DNA with 2 volumes of ethanol
l) Transfer DNA to 1 ml 70% (v/v) ethanol using a Pasteur pipette
m) Recover DNA by centrifugation at 12,000 g for 2 min, discard supernatant and redissolve the DNA in TE buffer or dH$_2$O Sequencing was carried out by Lark Technologies Inc. (Houston, Tex.). PA6, 103609, 103672 and 1894 DNA was prepared as above and then used to prepare a shotgun library from which clones were sequenced to derive the full genome sequence for each bacteriophage.

6. ORF Analysis

Open reading frames (ORF) in several bacteriophage isolates were analysed using software available through GeneMark™, a family of gene prediction programs provided by Mark Borodovsky's Bioinformatics Group at the Georgia Institute of Technology, Atlanta, Ga. The ORF analysis tool there uses a heuristic approach to identifying possible genes using a computational method described in: Besemer J. and Borodovsky M. (1999) *Nul. Acids Res.* 27: 3911-3920. The program can be found on the Internet at:

http://opal.biology.gatech.edu/GeneMark/heuristic_hmm2.cgi

Gene product function were determined by database comparison using the Blast analysis tool at http://www.ncbi.nlm.nih.gov/BLAST/.

Results

I. Testing of Bacteriophage Against Stock *P. ances* Strains

A collection of 46 independent bacteriophage isolates were tested against a panel of 21 *P. acnes* strains chosen for their deversity in age, origin and drug resistance profiles (listed in Table 1).

TABLE 1

List of strains used in bacteriophage host range screening tests.

| Strain number | Bacterial isolate |
|---|---|
| 1 | P37 |
| 2 | AT1 |
| 3 | NCTC737 |
| 4 | PF276 |
| 5 | PF286 |
| 6 | P506 |
| 7 | CavillA |
| 8 | CavillB |

TABLE 1-continued

List of strains used in bacteriophage host range screening tests.

| Strain number | Bacterial isolate |
|---|---|
| 9 | AT4 |
| 10 | AT5 |
| 11 | 101842c |
| 12 | 101845a |
| 13 | 101845b |
| 14 | 101846c |
| 15 | 101847a |
| 16 | 101848 |
| 17 | 101849 |
| 18 | 101850a |
| 19 | 101850b |
| 20 | 101851a |
| 21 | DSM16379 |

The ability of each bacteriophage to lyse each bacterial strain was tested to give an indication of the breadth of host specificity of each phage. The results in Table 2 show that, in general, all phages had broad specificity. Of these, 14 were able to infect all strains tested: PA6, 103609, 103625, 103629, 103664, 103672, 103715, 1869, 1874, 1878, 1894, 1905, 1909 and P37P.

TABLE 2

Summary of results from bacteriophage host range testing.

| Phage Isolate | *P. acnes* strain | | | | | | | | | | | | | | | | | | | | |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 |
| PA6 | + | + | + | + | + | + | + | + | + | + | + | + | + | + | + | + | + | + | + | + | + |
| 103205 | − | + | + | − | + | + | + | + | + | + | + | + | + | + | − | + | + | + | + | + | |
| 103600 | − | + | + | − | + | + | + | + | + | + | + | + | + | + | + | + | + | + | + | + | |
| 103601 | − | + | + | − | + | + | + | + | + | + | + | + | + | + | + | + | + | + | + | + | |
| 103609 | + | + | + | + | + | + | + | + | + | + | + | + | + | + | + | + | + | + | + | + | + |
| 103611 | + | + | + | + | + | + | + | + | + | + | + | + | + | + | + | + | + | + | + | + | − |
| 103614 | + | + | + | − | + | + | + | + | + | + | + | + | + | + | − | + | + | + | + | + | − |
| 103625 | + | + | + | + | + | + | + | + | + | + | + | + | + | + | + | + | + | + | + | + | + |
| 103629 | + | + | + | + | + | + | + | + | + | + | + | + | + | + | + | + | + | + | + | + | + |
| 103657 | − | + | + | − | + | + | + | + | − | + | + | + | + | + | + | + | + | + | + | + | |
| 103664 | + | + | + | + | + | + | + | + | + | + | + | + | + | + | + | + | + | + | + | + | + |
| 103666 | + | + | + | + | + | + | + | + | + | + | + | + | + | + | + | + | + | + | + | + | − |
| 103671 | + | + | + | + | + | + | + | + | + | + | + | + | + | + | + | + | + | + | + | + | − |
| 103672 | + | + | + | + | + | + | + | + | + | + | + | + | + | + | + | + | + | + | + | + | + |
| 103683 | + | + | + | + | + | + | + | + | + | + | + | + | + | + | + | + | + | + | + | + | − |
| 103695 | + | + | + | + | + | + | + | + | + | + | + | + | + | + | + | + | + | + | + | + | − |
| 103698 | − | + | + | − | + | + | + | + | − | + | + | + | + | + | − | + | + | + | + | + | |
| 103704 | + | + | + | + | + | + | + | + | + | + | + | + | + | + | + | + | + | + | + | + | − |
| 103713 | + | + | + | + | + | + | + | + | + | + | + | + | + | + | + | + | + | + | + | + | − |
| 103715 | + | + | + | + | + | + | + | + | + | + | + | + | + | + | + | + | + | + | + | + | + |
| 138 | − | + | + | − | + | + | + | + | + | + | + | + | + | + | + | + | + | + | + | + | |
| 139 | − | + | + | − | + | + | + | + | + | + | + | + | + | + | − | + | + | + | + | + | |
| 140 | − | + | + | − | + | + | + | − | + | + | + | + | + | + | − | + | + | + | + | + | |
| 1869 | + | + | + | + | + | + | + | + | + | + | + | + | + | + | + | + | + | + | + | + | + |
| 1874 | + | + | + | + | + | + | + | + | + | + | + | + | + | + | + | + | + | + | + | + | + |
| 1877 | − | + | + | − | + | + | + | + | + | + | + | + | + | + | − | + | + | + | + | + | |
| 1878 | + | + | + | + | + | + | + | + | + | + | + | + | + | + | + | + | + | + | + | + | + |
| 1880 | − | + | + | − | + | + | + | + | + | + | + | + | + | + | − | + | + | + | + | + | |
| 1881 | − | + | + | − | + | + | + | + | − | + | + | + | + | + | − | + | + | + | + | + | |
| 1883 | − | + | + | − | + | + | + | + | + | + | + | + | + | + | + | + | + | + | + | + | |
| 1885 | + | + | + | + | + | + | + | + | + | + | + | + | + | + | + | + | + | + | + | + | − |
| 1888 | − | + | + | − | + | + | + | + | + | + | + | + | + | + | − | + | + | + | + | + | |
| 1894 | + | + | + | + | + | + | + | + | + | + | + | + | + | + | + | + | + | + | + | + | + |
| 1895 | − | + | + | + | + | + | + | + | + | + | + | + | + | + | − | + | + | + | + | + | |
| 1900 | − | + | + | − | + | + | + | + | + | + | + | + | + | + | + | + | + | + | + | + | |
| 1901 | − | + | + | − | + | + | + | + | − | + | + | + | + | + | − | + | + | + | + | + | |
| 1902 | − | + | + | − | + | + | + | + | + | + | + | + | + | + | − | + | + | + | + | + | |
| 1905 | + | + | + | + | + | + | + | + | + | + | + | + | + | + | + | + | + | + | + | + | + |
| 1909 | + | + | + | + | + | + | + | + | + | + | + | + | + | + | + | + | + | + | + | + | + |
| 1922 | − | + | + | − | + | + | + | + | + | + | + | + | + | + | − | + | + | + | + | + | |

TABLE 2-continued

Summary of results from bacteriophage host range testing.

| Phage Isolate | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| 1923 | − | + | + | − | + | + | + | + | + | + | + | + | + | + | − | + | + | + | + | + |  |
| 1925 | + | + | + | + | + | + | + | + | + | + | + | + | + | + | + | + | + | + | + | + | − |
| 1928 | − | + | + | − | + | + | + | + | + | + | + | + | + | + | − | + | + | + | + | + |  |
| 1929 | − | + | + | − | + | + | + | + | + | + | + | + | + | + | − | + | + | + | + | + |  |
| P37P | + | + | + | + | + | + | + | + | + | + | + | + | + | + | + | + | + | + | + | + | + |

"+" denotes a positive reaction where bacteriophage is able to infect the host after applying neat phage stock to a seeded lawn of host bacteria in agar overlay.
"−" denotes a negative reaction where no infection was evident.

None of these strains showed an ability to infect the *P. granulosum, P. avidum, S. Epidermidis* and *C. bovis* species tested.

II. Testing of Bacteriophage PA6, 103609, 103625, 103629, 103664, 103672, 103715, 1869, 1874, 1878, 1894, 1905, 1909 and P37P Against *P. acnes* Isolated From Volunteers' Skin The 14 strains, shown above to have broad specificity, were further tested against 31 additional *P. acnes* strains, isolated from the skin of volunteers. The bacteriophage all showed lytic activity against these additional strains, as shown in Table 3:

TABLE 3

Summary of results from bacteriophage host range testing.

| Phage isolate | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|
| PA6 | + | + | + | + | + | + | + | + | + | + | + | + | + | + | + | + | + |
| P37P | + | + | + | + | + | + | + | + | + | + | + | + | + | + | + | + | + |
| 1869 | + | + | + | + | + | + | + | + | + | + | + | + | + | + | + | + | + |
| 1874 | + | + | + | + | + | + | + | + | + | + | + | + | + | + | + | + | + |
| 1878 | + | + | + | + | + | + | + | + | + | + | + | + | + | + | + | + | + |
| 1894 | + | + | + | + | + | + | + | + | + | + | + | + | + | + | + | + | + |
| 1905 | + | + | + | + | + | + | + | + | + | + | + | + | + | + | + | + | + |
| 1909 | + | + | + | + | + | + | + | + | + | + | + | + | + | + | + | + | + |
| 103609 | + | + | + | + | + | + | + | + | + | + | + | + | + | + | + | + | + |
| 103625 | + | + | + | + | + | + | + | + | + | + | + | + | + | + | + | + | + |
| 103629 | + | + | + | + | + | + | + | + | + | + | + | + | + | + | + | + | + |
| 103664 | + | + | + | + | + | + | + | + | + | + | + | + | + | + | + | + | + |
| 103672 | + | + | + | + | + | + | + | + | + | + | + | + | + | + | + | + | + |
| 103715 | + | + | + | + | + | + | + | + | + | + | + | + | + | + | + | + | + |

| Phage isolate | 39 | 40 | 41 | 42 | 43 | 44 | 45 | 46 | 47 | 48 | 49 | 50 | 51 | 52 |
|---|---|---|---|---|---|---|---|---|---|---|---|---|---|---|
| PA6 | + | + | + | + | + | + | + | + | + | + | + | + | + | + |
| P37P | + | + | + | + | + | + | + | + | + | + | + | + | + | + |
| 1869 | + | + | + | + | + | + | + | + | + | + | + | + | + | + |
| 1874 | + | + | + | + | + | + | + | + | + | + | + | + | + | + |
| 1878 | + | + | + | + | + | + | + | + | + | + | + | + | + | + |
| 1894 | + | + | + | + | + | + | + | + | + | + | + | + | + | + |
| 1905 | + | + | + | + | + | + | + | + | + | + | + | + | + | + |
| 1909 | + | + | + | + | + | + | + | + | + | + | + | + | + | + |
| 103609 | + | + | + | + | + | + | + | + | + | + | + | + | + | + |
| 103625 | + | + | + | + | + | + | + | + | + | + | + | + | + | + |
| 103629 | + | + | + | + | + | + | + | + | + | + | + | + | + | + |
| 103664 | + | + | + | + | + | + | + | + | + | + | + | + | + | + |
| 103672 | + | + | + | + | + | + | + | + | + | + | + | + | + | + |
| 103715 | + | + | + | + | + | + | + | + | + | + | + | + | + | + |

"+" denotes a positive reaction where bacteriophage is able to infect the host after applying neat phage stock to a seeded lawn of host bacteria in agar overlay.
"−" denotes a negative reaction where no infection was evident.

III. Identification of Non-lysogenic *P. acnes* Bacteriophage

Phage were screened for lysogenic activity as outlined in Method 4 above. Three of the broad host range phage listed in Table 3 above showed no evidence of lysogeny or resistance in these experiments, as outlined in Method 4 above, with results shown in Table 4. They were phages 1894, 103609 and 103672.

homology with other lysins and an amidase protein within the *P.acnes* g enome itself. The DNA sequence of this gene is shown in SEQ ID NO:2 and can be seen at nucleotides 15371-16233 of SEQ ID NO: 1.

Figure 2:
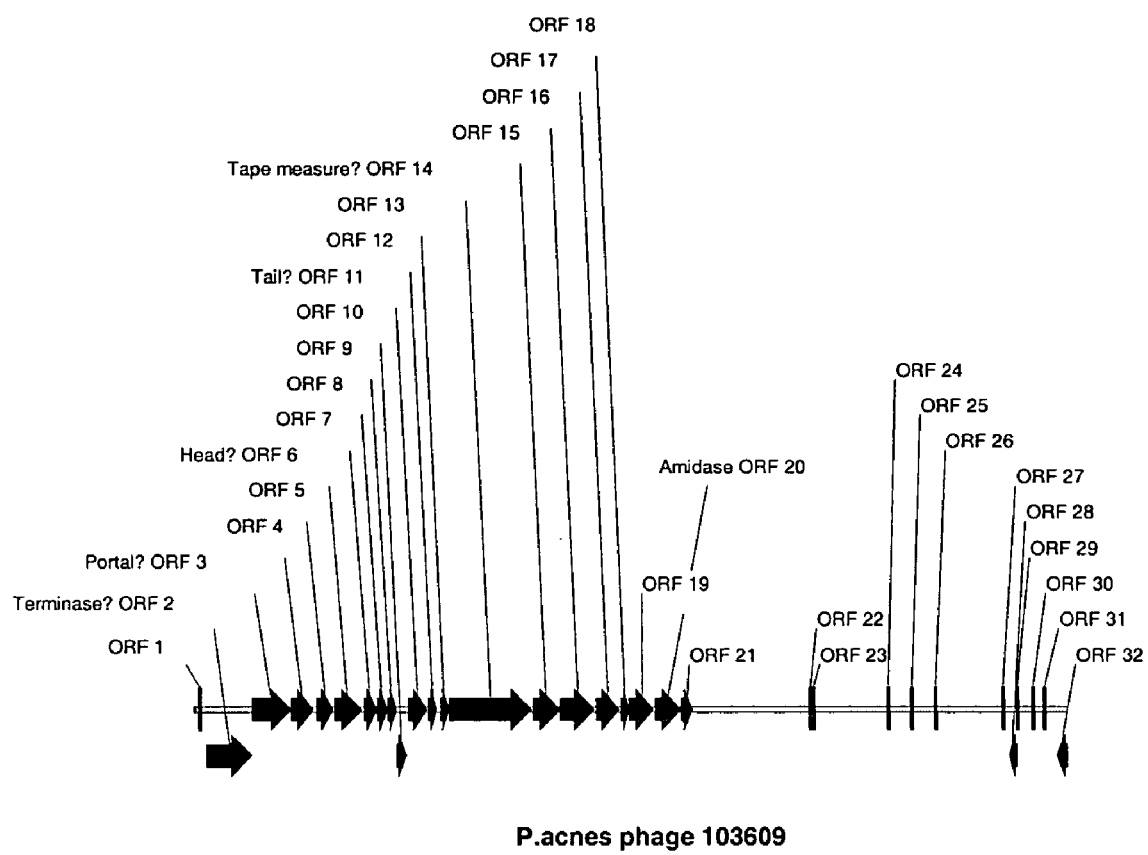
FIG. 2 shows the arrangement of open reading frames (ORFs) in the 103609 genome, with putative functions of various ORFs indicated.
Figure 3:
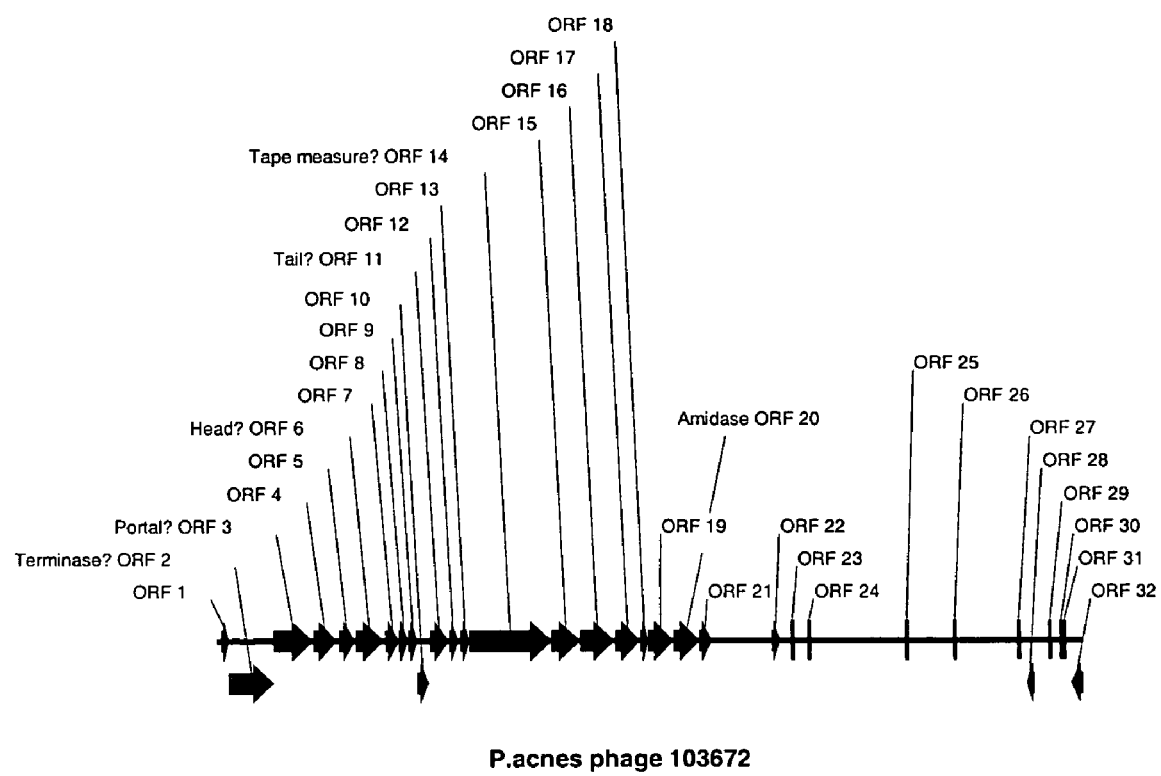
FIG. 3 shows the arrangement of open reading frames (ORFs) in the 103672 genome, with putative functions of various ORFs indicated.
Figure 4:
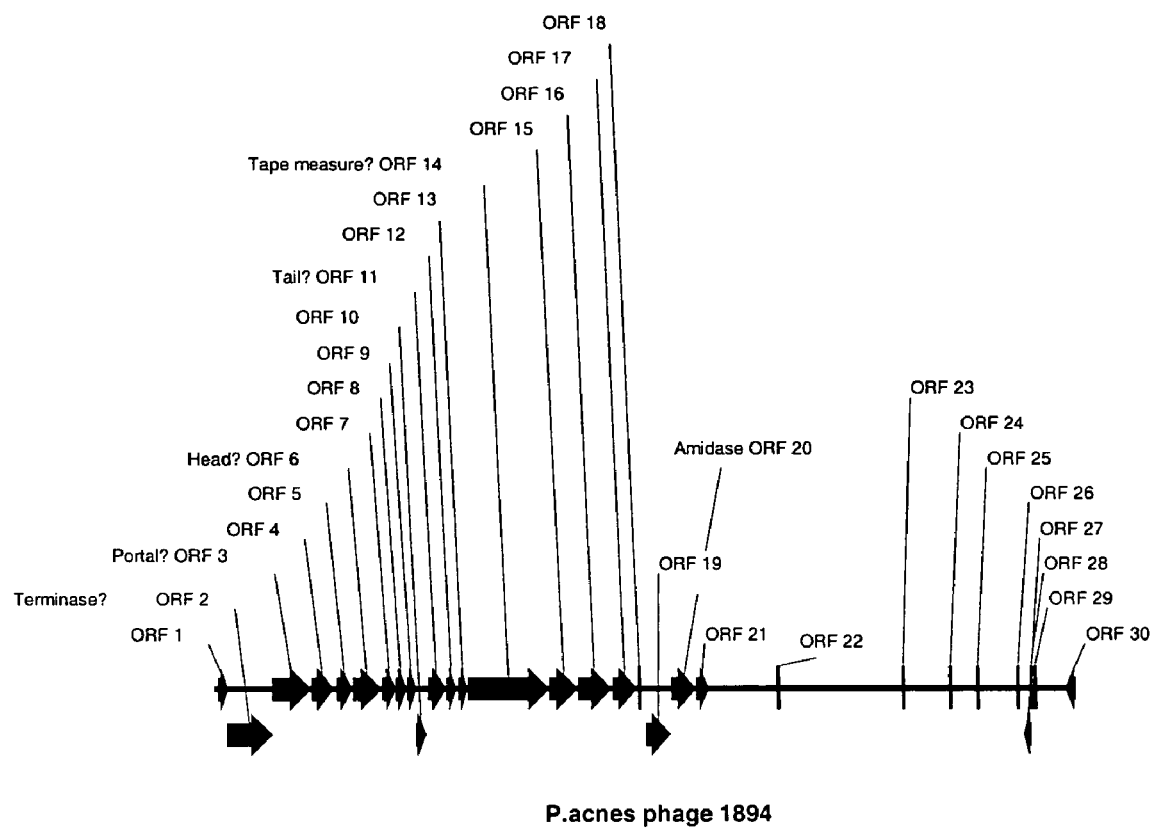
FIG. 4 shows the arrangement of open reading frames (ORFs) in the 1894 genome, with putative functions of various ORFs indicated.

A similar analysis was carried out for the genomes of 103609, 103672 and 1894, with the summary shown in FIG. 2 (103609), FIG. 3 (103672), FIG. 4 (1894) and Table 5.

TABLE 4

Data from repeated attempts to demonstrate lysogenic potential in phage. Phage infections (left column) of *P. acnes* strain AT1 were incubated for prolonged periods such that growth was visible within plaques. These emergent bacteria were sampled and tested for their susceptibility to infection with homologous or heterologous phage (top row).

| Potential Lysogen | PA6 | P37P | 1869 | 1874 | 1878 | 1894 | 1905 | 1909 | 103609 | 103625 | 103629 | 103664 | 103672 | 103715 |
|---|---|---|---|---|---|---|---|---|---|---|---|---|---|---|
| PA6 | N | N | N | N | N | Y | N | Y | Y | N | N | N | Y | N |
| P37P | N | N | N | N | N | Y | N | Y | Y | N | N | N | Y | N |
| 1869 | Y | Y | Y | Y | Y | Y | Y | Y | Y | Y | Y | Y | Y | Y |
| 1874 | Y | Y | N | Y | Y | Y | Y | Y | Y | Y | Y | Y | Y | Y |
| 1878 | N | N | Y | N | N | Y | N | Y | Y | N | N | N | Y | N |
| 1894 | Y | Y | Y | Y | Y | Y | Y | Y | Y | Y | Y | Y | Y | Y |
| 1905 | N | N | N | N | N | Y | N | Y | Y | N | N | N | Y | N |
| 1909 | N | N | N | N | N | Y | N | N | Y | N | N | N | Y | N |
| 103609 | Y | Y | Y | Y | Y | Y | Y | Y | Y | Y | Y | Y | Y | Y |
| 103625 | N | Y | N | N | Y | Y | Y | Y | Y | Y | Y | Y | Y | N |
| 103629 | N | Y | N | N | N | Y | N | N | Y | N | N | N | Y | N |
| 103664 | N | Y | N | N | N | Y | N | Y | Y | N | N | Y | Y | N |
| 103672 | Y | Y | Y | Y | Y | Y | Y | Y | Y | Y | Y | Y | Y | Y |
| 103715 | N | Y | N | N | N | Y | Y | Y | Y | N | Y | Y | Y | N |

'N' indicates resistance and therefore demonstration of lysogenic activity.
Three strains 1894, 103609 and 103672 (underlined) failed to demonstrate lysogenic activity.

IV. DNA Sequencing

The genome for each of bacteriophages PA6, 103609, 103672 and 1894 was sequenced as outlined in Method 5 above. The sequences for each are shown in SEQ ID NO:1 (PA6), SEQ ID NO:3 (103609), SEQ ID NO:4 (103672) and SEQ ID NO:5 (1894).

V. ORF Analysis of Bacteriophage Genomes

Analysis of open reading frames (ORF) within the PA6 genome and subsequent analysis of predicted protein sequences using the Blast database analysis tool identified various potential genes and highlighted possible functions (summary of analysis shown in FIG. 1). The 5' end of the phage genome appears to host many of the structural genes which comprise the phage coat and tail. Notable among the remaining genes is a potential lysin (ORF 20) which shares Again, ORF 20 in each case encodes a potential lysin. The DNA sequence for this gene is shown in SEQ ID NO: 6 (phage 103609, nucleotides 15442-16296 of SEQ ID NO: 3), SEQ ID NO:7 (phage 103672, nucleotides 15382-16245 of SEQ ID NO: 4) and SEQ ID NO:8 (phage 1894, nucleotides 15416-16273 of SEQ ID NO: 5). The boundaries for each ORF for each bacteriophage strain are shown in Table 5. No repressor protein is obvious from sequence homology analysis in these phage strains and this is an indication that these are purely lytic phage, unable to sustain lysogeny, as supported by the results shown in Table 4. Therefore, this confirms that these phage strains are ideal in this respect as candidates for phage therapy.

TABLE 5A

ORF boundaries for phage 103609, 103672 and 1894
(−) indicates that the ORF is coded on the reverse DNA strand

| 1894 ORFs (30 total) | 103609 ORFs (32 total) | 103672 ORFs (32 total) |
|---|---|---|
| ORF 1 Start: 53 End: 361 | ORF 1 Start: 145 End: 363 | ORF 1 Start: 113 End: 361 |
| ORF 2 Start: 361 End: 1872 | ORF 2 Start: 363 End: 1874 | ORF 2 Start: 361 End: 1872 |
| ORF 3 Start: 1869 End: 3194 | ORF 3 Start: 1871 End: 3196 | ORF 3 Start: 1869 End: 3194 |
| ORF 4 Start: 3201 End: 3956 | ORF 4 Start: 3203 End: 3958 | ORF 4 Start: 3198 End: 3953 |
| ORF 5 Start: 4067 End: 4621 | ORF 5 Start: 4069 End: 4629 | ORF 5 Start: 4057 End: 4611 |
| ORF 6 Start: 4628 End: 5575 | ORF 6 Start: 4636 End: 5583 | ORF 6 Start: 4618 End: 5565 |
| ORF 7 Start: 5620 End: 6081 | ORF 7 Start: 5627 End: 6088 | ORF 7 Start: 5613 End: 6074 |
| ORF 8 Start: 6083 End: 6430 | ORF 8 Start: 6090 End: 6437 | ORF 8 Start: 6076 End: 6422 |
| ORF 9 Start: 6437 End: 6727 | ORF 9 Start: 6444 End: 6734 | ORF 9 Start: 6430 End: 6720 |
| ORF 10 Start: 6724 End: 7095 | ORF 10 Start: 6731 End: 7102 | ORF 10 Start: 6717 End: 7087 |
| ORF 11 Start: 7147 End: | ORF 11 Start: 7154 End: | ORF 11 Start: 7140 End: |

TABLE 5A-continued

ORF boundaries for phage 103609, 103672 and 1894
(−) indicates that the ORF is coded on the reverse DNA strand

| 1894 ORFs (30 total) | 103609 ORFs (32 total) | 103672 ORFs (32 total) |
|---|---|---|
| 7776 | 7795 | 7769 |
| ORF 12 Start: 7803 End: 8099 | ORF 12 Start: 7824 End: 8120 | ORF 12 Start: 7797 End: 8093 |
| ORF 13 Start: 8198 End: 8485 | ORF 13 Start: 8219 End: 8506 | ORF 13 Start: 8192 End: 8479 |
| ORF 14 Start: 8493 End: 11258 | ORF 14 Start: 8514 End: 11279 | ORF 14 Start: 8487 End: 11252 |
| ORF 15 Start: 11274 End: 12215 | ORF 15 Start: 11295 End: 12236 | ORF 15 Start: 11270 End: 12211 |
| ORF 16 Start: 12223 End: 13380 | ORF 16 Start: 12244 End: 13401 | ORF 16 Start: 12219 End: 13376 |
| ORF 17 Start: 13430 End: 14218 | ORF 17 Start: 13451 End: 14239 | ORF 17 Start: 13425 End: 14213 |

TABLE 5B

ORF boundaries for phage 103609, 103672 and 1894 (continued)
(−) indicates that the ORF is coded on the reverse DNA strand

| 1894 ORFs (30 total) | 103609 ORFs (32 total) | 103672 ORFs (32 total) |
|---|---|---|
| ORF 18 Start: 14299 End: 14538 | ORF 18 Start: 14296 End: 14559 | ORF 18 Start: 14259 End: 14522 |
| ORF 19 Start: 14541 End: 15374 | ORF 19 Start: 14563 End: 15387 | ORF 19 Start: 14525 End: 15340 |
| ORF 20 Start: 15416 End: 16273 | ORF 20 Start: 15442 End: 16296 | ORF 20 Start: 15382 End: 16245 |
| ORF 21 Start: 16286 End: 16684 | ORF 21 Start: 16309 End: 16707 | ORF 21 Start: 16258 End: 16656 |
| ORF 22 Start: 19047 End: 19103 | ORF 22 Start: 20662 End: 20766 | ORF 22 Start: 18710 End: 18955 |
| ORF 23 Start: 23248 End: 23391 | ORF 23 Start: 20767 End: 20919 | ORF 23 Start: 19393 End: 19497 |
| ORF 24 Start: 24869 End: 25012 | ORF 24 Start: 23272 End: 23415 | ORF 24 Start: 19946 End: 20044 |
| ORF 25 Start: 25760 End: 25810 | ORF 25 Start: 24093 End: 24293 | ORF 25 Start: 23239 End: 23382 |
| ORF 26 Start: 27128 End: 27172 (−) | ORF 26 Start: 24899 End: 25042 | ORF 26 Start: 24863 End: 25006 |
| ORF 27 Start: 27340 End: 27582 (−) | ORF 27 Start: 27152 End: 27196 (−) | ORF 27 Start: 27006 End: 27164 |
| ORF 28 Start: 27586 End: 27708 (−) | ORF 28 Start: 27326 End: 27583 (−) | ORF 28 Start: 27268 End: 27522 (−) |
| ORF 29 Start: 27721 End: 27888 (−) | ORF 29 Start: 27593 End: 27715 (−) | ORF 29 Start: 28059 End: 28133 (−) |
| ORF 30 Start: 28743 End: 29108 (−) | ORF 30 Start: 28126 End: 28200 (−) | ORF 30 Start: 28424 End: 28465 (−) |
| | ORF 31 Start: 28528 End: 28569 (−) | ORF 31 Start: 28534 End: 28683 (−) |
| | ORF 32 Start: 28891 End: 29274 (−) | ORF 32 Start: 28779 End: 29153 (−) |

The % sequence identity of the DNA sequences in the ORFs between the three bateriophage is shown in Table 6:

TABLE 6

% sequence identity of each ORF between the three phage 103609, 103672 & 1894;

| ORF | Identity (%) |
|---|---|
| 1 | 62.7* |
| 2 | 90.3 |
| 3 | 90.0 |
| 4 | 90.0 |

TABLE 6-continued

% sequence identity of each ORF between the three phage 103609, 103672 & 1894;

| ORF | Identity (%) |
|---|---|
| 5 | 88.6 |
| 6 | 91.9 |
| 7 | 95.2 |
| 8 | 93.1 |
| 9 | 94.8 |
| 10 | 90.8 |
| 11 | 92.5 |

TABLE 6-continued

% sequence identity of each ORF between the three phage 103609, 103672 & 1894;

| ORF | Identity (%) |
|-----|--------------|
| 12 | 96.3 |
| 13 | 98.6 |
| 14 | 90.1 |
| 15 | 92.7 |
| 16 | 93.5 |
| 17 | 96.5 |
| 18 | 66.9 |
| 19 | 79.7 |
| 20 | 87.4 |
| 21 | 85.2 |
| 22 | 96.4 |
| 23 | 97.2 |
| 24 | 92.3 |
| 25 | 86.0 |
| 26 | 62.2 |
| 27 | 79.8 |
| 28 | 77.9 |
| 29 | 65.9 |
| 30 | 86.8 |
| 31 | — |
| 32 | — |

*ORF1 for 1894 is over 100 nucleotides longer than for either 103609 or 103672.

Figure 5:
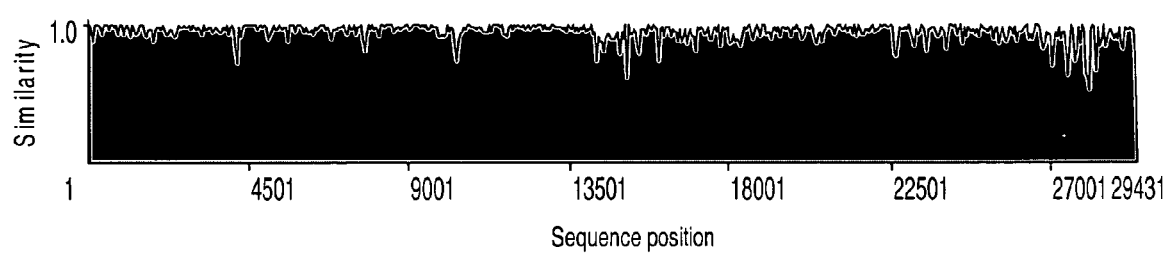
FIG. 5 shows a graphical representation of DNA sequence alignment of phages 103672, 103609 and 1894.

FIG. 5 shows the outcome of a sequence homology analysis between 103609, 103672 and 1894, in which similarity level of 1.0 indicates 100% identity, with similarity falling according to the nature and number of differences between the three sequences. This analysis demonstrates that overall sequence identity between all of these three phage is 86.1%.

Figure 6:
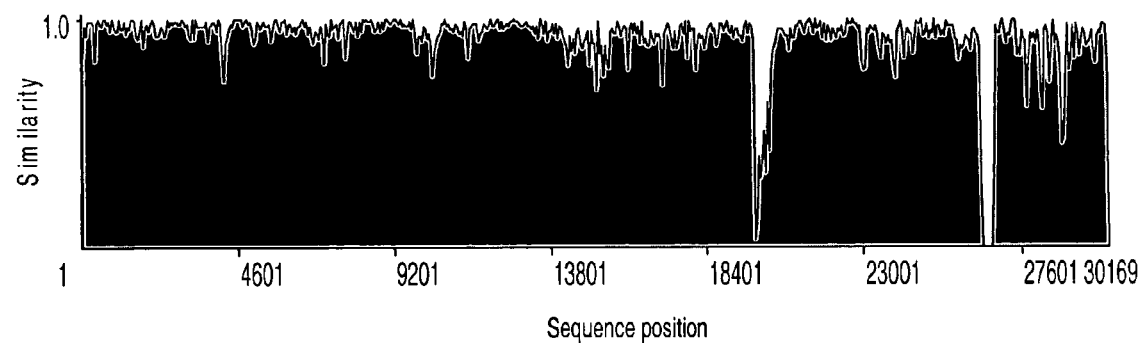
FIG. 6 shows a graphical representation of DNA sequence alignment of PA6 versus 103672, 103609 and 1894.

FIG. 6 shows the results of a similar analysis between these three phage and PA6, a bacteriophage which does not show the desired characteristic of being incapable of sustaining lysogeny in a bacterium (see results Section III above). This analysis demonstrates that overall sequence identity between all of these four phage is 80.1%. Overall sequence identity between 1894 and PA6 is 87.4%, between 103609 and PA6 is 86.8% and between 103672 and PA6 is 87.3%.

FIG. 6 clearly shows that there are two regions of low or zero % sequence identity when the DNA sequences of the three phage 103609, 103672 and 1894 are compared to that of PA6. FIGS. 7 and 8 show that this is the result of the presence of nucleotide sequences in PA6 which are not present in any of the other three phage.

Referring to nucleotide sequence numbering according to that shown in FIGS. 7 and 8, nucleotides 19804-10843 of PA6 are shown as SEQ ID NO: 9; nucleotides 19876-19901 of PA6 are shown as SEQ ID NO:10; nucleotides 19913-19969 of PA6 are shown as SEQ ID NO:11; nucleotides 19979-20054 of PA6 are shown as SEQ ID NO: 12; and nucleotides 26242-26620 of PA6 are shown as SEQ ID NO: 13.

Without wishing to be bound by theory, although these DNA inserts are present in PA6 in non-ORF regions of the genome, the presence of such large additional DNA inserts could have an effect on the overall structure of the genome and could affect, for example, the efficacy of expression of the ORF regions.

VI. Utilising Bacteriophage 103672 as an Anti-*P. acnes* Treatment

Bacteriophage 103672 was tested against *P. acnes* bacteria immediately after isolation of the bacteria from a volunteer's skin, as outlined in Method 3.4 above. The results are as shown in Table 7:

TABLE 7

Results of incubation of *P. acnes* isolated from the skin of a volunteer, in the absence or presence of bacteriophage 103672

| Initial propionibacterial count, cfu ml$^{-1}$ (Phage:cell ratio) | Final count, cfu cm$^{-2}$ (control) | Final count, cfu cm$^{-2}$ (+103672) |
|---|---|---|
| 1.585 × 10$^5$ (6:1) | Too much growth to quantify | 0 |

This clearly shows the efficacy of the bacteriophage against *P. acnes* directly isolated from the skin of the patients and demonstrates the usefulness of such bacteriophage as an anti-*P. acnes* agent, whether directly within a method of treatment of acne or as an ingredient in a medicament for use in such a method.

The invention claimed is:

1. An isolated bacteriophage having a genome which comprises the DNA sequence of SEQ ID NO: 3.

2. An isolated polynucleotide comprising the nucleotide sequence of SEQ ID NO:3.

* * * * *

SEQUENCE LISTING

<160> NUMBER OF SEQ ID NOS: 13

<210> SEQ ID NO 1
<211> LENGTH: 29739
<212> TYPE: DNA
<213> ORGANISM: Bacteriophage PA6

<400> SEQUENCE: 1

```
agtgaaatac ctcccttttg tggttttgtc tgtttgtcga cttttttgtgt tggtggtgag      60 tgttgtgcag cctgagcttc ctgagtctcg tgagtggtgt ggggagacgc gtcgttggtg     120
gcgtgtgtgg ggtgaggata gtcgcgcgcc gtatgtgtct gatgaggagt ggttgttttct    180 tatggatgct gcggtgattc atgattgtgt gtggcgtgag ggtcgcgcgg atttggtggc    240
ttcgcttcgt gcgcatgtga aggcttttat gggcatgttg gataggtatt cggttgatgt    300
ggcgtctggt ggccgtggtg ggggttctgc tgtggcgatg attgaccggt ataggaagcg    360 tagggggggct tgagtaggtg tctggtgttg ttgggtctca ggttcctcgt caccgtgtgg    420
```

```
ctgcggcgta ttcggtgtct gctgggggtg atgctgggga gcttggtcgt gcgtatgggt    480
tgacgcctga tccgtggcag cagcaggtgt tggatgattg gctggctgtc ggtagcaatg    540
gcaggcttgc ttctggtgtg tgtggggtgt ttgttccgcg gcagaatggc aagaatgcta    600
ttttggagat tgtggagttg tttaaggcga ctattcaggg tcgccgtatt ttgcatacgg    660
ctcacgagtt gaagtcggct cgtaaggcgt tatgcggtt gaggtcgttt tttgagaatg    720
agcggcagtt tcctgacttg tatcgtatgg tgaagtcgat tcgtgcgacg aatggtcagg    780
aggctattgt gttgcatcat ccggattgtg ccacttttga gaagaagtgt ggctgcagcg    840
gttggggttc ggttgagttt gtggctcgta gccggggttc ggctcgcggg tttacggttg    900
atgatttggt gtgtgatgag gctcaggagt tgtcggatga gcagttggag gctttgcttc    960
ctacggtaag tgctgccccg tctggtgatc cgcagcagat ttttccttggt acgccgcctg   1020
ggccgttggc tgatggttct gtggtgttgc gtttgcgtgg gcaggcgctt ggtggcggta   1080
aaaggtttgc gtggacggag ttttcgattc ctgacgagtc tgatccggat gatgtgtcgc   1140
ggcagtggcg gaagttggcg ggggatacga atccggcgtt ggggcgtcgc ctgaattttg   1200
ggaccgtaag cgatgagcat gagtcgatgt ctgctgccgg ttttgctcgg gagcggcttg   1260
gctggtggga tcgtggccag tctgctgcgt ctgtggttcc tgctgataag tgggctcagt   1320
ctgcggtgga tgaggcgagt ctggttggcg ggaaagtgtt tggtgtctcg ttttctcgtt   1380
ctggggatcg ggttgctttg gcgggtgccg gcaagactga tgctggggtt catgttgagg   1440
ttattgatgg gctgtcggga acgattgttg atggtgtggg ccggttggct gactggttgg   1500
cggttcgttg gggtgatact gaccggatca tggttgccgg gtctggtgcg gtgttgttgc   1560
agaaggcgtt gacggatcgt ggtattccgg gccgtggcgt ggtggttgct gatactggcg   1620
tttatgtgga ggcttgtcag gcgtttcttg agggtgtcag gtcgggtgtg atcagtcatc   1680
ctcgtgctga ttctcgccgt gacatgttgg atattgctgt gaggtcggct gtgcagaagc   1740
gtaaggggtc tgcgtggggt tggggttcct cgtttaagga tggttctgag gttcctttgg   1800
aggctgtgtc tttggcgttt ttgggggcta acgtgttcg tcgtggccgt cgggagcgta   1860
gtggtaggaa gcgggtgtct gtggtatgaa ctcggatgag ttggctctga ttgagggcat   1920
gtacgatcgt atccaaaggt tgtcttcgtg gcattgttgt attgagggct actatgaggg   1980
ctctaatcgg gtgcgtgacc ttggtgtggc tattccgccg gagttgcagc gtgtgcagac   2040
tgtggtgtcg tggcctggta tagctgtgga tgctttggag gagcgtctgg attggcttgg   2100
ctggactaat ggtgacggct acggccttga tggtgtgtat gctgcgaatc ggcttgctac   2160
ggcgtcgtgt gatgtgcatt tggatgcgct gattttggg ttgtcgtttg ttgcgatcat   2220
tcctcatggt gatggtacgg tgtcggttcg tccgcagtca ccaaagaatt gtacgggcaa   2280
gttttcggct gacgggtctc gtttggatgc gggtttggtg gtgcagcaga cgtgtgatcc   2340
tgaggttgtt gaggctgagc ttttgcttcc tgatgtgatt gttcaggtgg agcggcgggg   2400
ttcgcgtgaa tgggttgagg tggatcgtat accgaatgtg ttgggtgcgg ttccgttggt   2460
gcctattgtg aatcgtcgcc gtacttctag gattgatggc cgttcggaga ttacgaggtc   2520
tattagggct tacacggatg aggctgtgcg cacactgttg gggcagtctg tgaatcgtga   2580
ttttttatgcg tatcctcagc gttgggtgac tggcgtgagc gcggatgagt tttcgcagcc   2640
tggctgggtc ctgtcgatgg cttctgtgtg ggctgtggat aaggatgatg acggtgacac   2700
tccgaatgtg gggtcgtttc ctgtcaatag tcctacaccg tattcggatc agatgagact   2760
```

```
gttggcgcag ttgactgcgg gtgaggcggc tgttccggaa cgctatttcg ggtttatcac   2820
gtctaaccca cctagtgggg aggctttggc tgccgaggaa tctcggcttg tgaagcgtgc   2880
tgagcggcgt caaacgtcgt ttggtcaggg ttggctgtcg gttggttttt tggctgccaa   2940
ggcgttggat tctcgtgttg atgaggccga ttttttttggt gatgttggtt tgcgttggcg   3000
tgatgcttcg acgcctaccc gggcggctac ggctgatgct gtgacgaagc ttgttggtgc   3060
cggtattttg cctgctgatt ctcgtacggt gttggagatg ttggggcttg atgatgtgca   3120
ggttgaggct gtgatgcgtc atcgtgctga gtcgtctgac ccgttggcgg tgcttgctgg   3180
ggctatatcg cgtcaaacta acgaggtatg ataggcgatg gcttcggggg ttgaggcgag   3240
gcttgcggcg actgagtatc agcgtgaggc ggtcaggttt gctgggaagt atgcgggcta   3300
ttattctgag cttggtcgtt tgtggcgtgc cggcaggatg agtgacacgc agtatgtgcg   3360
tttgtgtgtg gagttggagc gtgccggcca tgatggttcg gcatcgttgg ctgccaggtt   3420
tgtgtcggat tttcgccggt tgaatggtgt ggatccgggt ttgattgtgt atgacgagtt   3480
tgatgctgcg gcggctttgg ctaggtctat ttcgaccacg aagattcttg agagtgaccc   3540
ggatagggcg aatgacacga ttgatgcgat ggcggcgggt tttgatcggg ctgttatgaa   3600
tgctggccgt gacacggttg agtggtctgc gggtgcgcag ggtaggtcgt ggcgtcgggt   3660
gacggatggt gatccgtgtg cttttttgtgc catgttggct acgaggtcgg attatacgac   3720
aaaagagagg gcacttacta ctggacatac tcggcgtcat aagcgtggtg gtaagcgtcc   3780
gtttggttcg aagtatcatg atcattgtgg ttgtacggtg gttgaggttg ttggcccttg   3840
ggaaccaaat agggctgatg ccgagtatca gaggacgtat gagaaggcct gtgagtgggt   3900
tgatgatcat gggttgcagc aatcgcctgg caatattttg aaggctatgc gtactgttgg   3960
cgacatgaga taatttgatg tggtttccgg ttgtgcgccg ccggttattg gtgcacaggg   4020
ttgtctcccg cacgggggtc aacaatattg tgttgttttc cgcaaggagt gtagggttag   4080
gctatggccg atcagagtgt tgaggaacag aatgttgaca atgatgttgt ggagtccgga   4140
aaggataacg gcattgttga tacagtaaaa gacgatggcg ggcaggaggt agccgacaat   4200
cagttgaaga atgaaggcga gggtaaatcg ccggggactg attggaaggc tgaggcccgt   4260
aagtgggagt ctcgtgctaa aagtaatttt gccgagttgg agaagcttcg cgcctcggat   4320
ggtgatgcgg ggtctacgat tgatgagctt cgccgcaaga atgaggaact cgaagaccgg   4380
atcaatgggt ttgttcttga gggtgtgaag cgccgaggtgg ctgccgagtg tggcctgtcg   4440
ggtgatgctg tcgctttctt gtcgggtggc gataaggagt cgcttgccga gtctgcgaaa   4500
gctttgaagg gtttgatcga ccatagtagt ggtggcgcgg gtgtgcgccg tcttgcgggg   4560
agtgcccccg ttgatgatgt taaacgacgt gagggtgtcg cgtttgtgga tgctcttgtc   4620
aataattcta ggagatgatt tgtgatggct gacgattttc tttctgcagg gaagcttgag   4680
cttcctggtt ctatgattgg tgcggttcgt gaccgtgcta tcgattctgg tgttttggcg   4740
aagctttcgc cggagcagcc gactattttc gggcctgtga agggtgccgt gtttagtggt   4800
gttcctcgcg ccaagattgt tggtgagggc gaggttaagc cttccgcgtc tgttgatgtt   4860
tcggcgttta ctgcgcagcc tatcaaggtt gtgactcagc agcgtgtctc ggatgagttt   4920
atgtgggctg atgctgatta ccgtctgggt gtgcttcagg atctgatttc cccggctctt   4980
ggtgcttcga ttggtcgcgc cgtggatctg attgctttcc atggtattga tcctgccact   5040
ggtaaagcgg cttccgctgt gcatacttcg ctgaataaga cgaagaatat tgttgatgcc   5100
acggattctg ctacggctga tcttgttaag gctgtcggcc tgattgctgg tgctggtttg   5160
```

```
caggttccta acggggttgc tttggatccg gcgttctcgt ttgcgctgtc tactgaggtg    5220
tatccgaagg ggtctccgct tgccggtcag cctatgtatc ctgccgccgg gtttgccggt    5280
ttggataatt ggcgcgggct gaatgttggt gcttcttcga ctgtttctgg cgccccggag    5340
atgtcgcctg cctctggcgt taaggctatt gttggtgatt tctctcgtgt tcattggggt    5400
ttccagcgta acttcccgat cgagcttatc gagtatggtg acccggatca gactgggcgt    5460
gacttgaagg gccataatga ggttatggtt cgtgccgagg ctgtcctgta tgttgcgatt    5520
gagtcgcttt attcgtttgc tgttgtgaag gagaaggctg ccccgaagcc taatccgccg    5580
gccgagaact gattcatttg ttgcggtgat gttttctatg tgcagggggt ggtgttgatg    5640
ggtatcattt tgaagcctga ggatattgag cctttcgccg atattcctag agagaagctt    5700
gaggcgatga ttgccgatgt ggaggctgtg gctgtcagtg tcgcccctg tatcgctaaa    5760 ccggatttca aatacaagga tgccgctaag gctattctgc gcagggccct gttgcgctgg    5820
aatgataccg gggtttcggg tcaggtgcag tacgagtctg cgggcccgtt tgctcagact    5880
acacggtcga atactcccac gaatttgttg tggccttctg agattgccgc gttgaagaag    5940
ttgtgtgagg gtgatggtgg ggctggtaaa gcgttcacta ttacaccgac catgaggagt    6000
agtgtgaatc attctgaggt gtgttccacg gtgtggggtg agggttgctc gtgcggatct    6060
gatattaacg gctatgctgg ccctttgtgg gagatatgat atgaccggtt tccttacgg    6120 tgaaacggtt gtgatgcttc aaccgactgt tcgtgtcgat gatcttggcg acaaggtgga    6180
agactggtct aagcctgtcg agactgtgta ccataacgtg gccatctatg cttccgtttc    6240
gcaggaggat gaggctgccg gccgtgactc tgactatgag cattggtcga tgcttttcaa    6300
gcagcctgtt gtgggtgccg gttatcgttg ccggtggcgt attcggggtg tggtttggga    6360
ggcggacggg tctcctatcg tgtggcatca tccgatgtct ggttgggatg ctggtacgca    6420
ggttaatgtg aagcgtaaga agggctgatg ggttgtggct caggatgtga atgtgaagct    6480
gaacttgccg ggtattcgtg aggtgttgaa gtcttctggg gtgcagtcga tgttggctga    6540
gcgtggcgag cgggtgaggc gtgcggcttc ggcgaatgtt ggcggtaatg cttttgatag    6600
ggcccaatac cgtagtggtt tgtcgtcgga ggtgcaggtt caccgtgtgg aggctgtggc    6660
gaggattggc accacctata agggtgggaa gcgtattgag gcgaagcatg gcacgttggc    6720
gaggtcgatt ggggctgcgt cgtgatcgtt tacggtgatc cgcgtgtgtg ggctaaacgt    6780
gtgctcaagg atgatggctg gctgtccgat atacccgtgt ggggacggt gcctgacgat    6840 ttcagcggtg acctgatttg gttggcgttg gatggcggcc cacagttgca tgttcgcgag    6900
caggtgtttt tgcgggtgaa cgtgtttct gatatgcctg atcgtgccat gtcgctagcc    6960 aggcggggttg aggctgtcct tgtagacggt gtggacggtg acccggtggt gttttgtcga    7020
cggtctactg gccctgattt gctggttgat ggtgcacgtt ttgatgtgta ttcgctgttt    7080
gagctgatat gcaggcctgt cgaatccgag taaacgtttt gttttgatat tgttgtttgt    7140
ttttgttttg atattgtttt tgggggttat gatggctgga acacgtaaag cgtctaatgt    7200
tcgttccgcg gttacggggtg acgtctatat tggtaaagct catgccggtg acactattga    7260
tggtgtgaag acggttcctg acgggcttac agctttaggg tatctgtctg atgacgggtt    7320
taagattaaa ccggagcgta aaacggatga tttgaaggct tggcagaatg cggatgttgt    7380
tcgcactgtg gctacggaat cgtctatcga gatttctttc cagctgatcg agtctaagaa    7440
ggaggttatc gagctgtttt ggcagtcgaa ggttactgcc ggagccgatt cgggttcgtt    7500
```

-continued

```
cgatatttct cctggtgcca cgacgggtgt tcatgccctg ttgatggata ttgttgatgg   7560
cgatcaggtt attcgctact atttccctga ggttgagttg atcgatcgtg acgagattaa   7620
gggtaagaat ggcgaggtgt atgggtatgg tgtgacgttg aaggcgtatc ctgcccagat   7680
taataagaag ggtgatgcgg tgtctggtcg ggggtggatg acggctttaa aagctgatac   7740
tcctccgact cctcctccgg ccccgaatcc tccgaagcct gagccggatc cgaatccgcc   7800
gtctaataac tgatacacat agtttgaggg attgttgata gatgagtgac acgggttaca   7860
cgttgaagat tggtgaccgt agctgggtgt tggcggatgc ggaggagacg gctcaggctg   7920
ttcctgcccg cgttttccgt cgtgctgcta agattgccca gtcgggtgag tctgcggatt   7980
tcgcccaggt tgaggtgatg ttttctatgt tggaggctgc cgccccggct gacgcggtgg   8040
aggccctgga ggggcttcct atggttcgtg tggccgagat tttccgccag tggatggaat   8100
acaagcctga cggtaagggt gcctcgctgg gggaatagtt tggctccacg gcctgattga   8160
tgattatcgt ggggccatcg aatacgattt ccgcaccaag tttggtgttt ctgtttatag   8220
tgttggtggc ccgcagatgt gttggggtga ggctgtccgg ctggctggcg tgttgtgtac   8280
cgatacgtct agccagttgg cggcccacct gaatggttgg aagcgcccgt ttgagtggtg   8340
cgagtgggct gtgttggaca tgctggatca ttacaggtct gctaatagtg aggggcagcc   8400
ggagcctgtg gcgaggccta cggatgagcg taggcgccgg tttacgtctg ggcaggtgga   8460
cgatattttg gcgcgtgttc gtgctggtgg cggggtgtct cgcgagatta atattatggg   8520
gtgaatagtg tatgtctggt gagattgctt ccgcatatgt gtcgttgtat acgaagatgc   8580
ctggtttgaa ggcggatgtt ggtaaacagc tttctggggt gatgcctgct gagggtcagc   8640
gttcgggtag tttgtttgct aagggaatga agttggctct tggtggtgcg gcgatgatgg   8700
gtgccatcaa tgttgctaag aagggcctca agtcgattta tgatgtgact attggtggcg   8760
gtattgctag ggcgatggct attgatgagg ctcaggctaa gttgactggt ttgggtcata   8820
cgtcttctga cacgtcttcg attatgaatt cggctattga ggctgttact ggtacgtcgt   8880
atgcgttggg ggatgcggcg tctacggctg cggcgttgtc tgcttcgggt gtgaagtctg   8940
gcgggcagat gacggatgtg ttgaagactg tcgccgatgt gtcttatatt tcgggtaagt   9000
cgtttcagga tacgggcgct atttttacgt ctgtgatggc tcgcggtaag ttgcagggcg   9060
atgacatgtt gcagcttact atggcgggtg ttcctgtcct gtctttgctt gccaggcaga   9120
ctggtaaaac gtctgctgag gtgtcgcaga tggtgtcaaa ggggcagatt gattttaaca   9180
cgtttgcggc tgcgatgaag cttggcatgg gtggtgctgc gcaggcgtct ggtaagacgt   9240
ttgagggcgc tatgaagaat gttaagggcg ccctgggtta tcttggtgct acggctatgg   9300
ccccgttttct taacgggttg cggcagattt tgttgcgtt gaatccggtt atcaagtctg   9360
tcacggattc cgtgaagccg atgtttgctg ccgtcgatgc tggtattcag cgtatgatgc   9420
cgtctatttt ggcgtggatt aaccgtatgc cggctatgat cactcgaatg aatgcacaga   9480
tgcgcgccaa ggtggagcag ttgaagggcg ttttttgcaag gttgcatttg cctgttccta   9540
aggtgaattt gggtgccatg tttgctggcg gcaccgcagt gttcggtatt gttgctgcgg   9600
gtgttgggaa gcttgtcgcg gggtttgccc cgttggcggt gtcgttgaag aatctgttgc   9660
cgtcgtttgg tgcttgagg ggtgccgccg ggggcttgg tggcgtgttt cgcgccttgg   9720
gtggccctgt tggtattgtg atcggcttgt ttgctgccat gttttgctacg aacgcccagt   9780
tccgtgccgc tgttatgcag cttgtggggg tggttggccg ggctttgggg cagattatgg   9840
tcgccttgca gccattgttc gggattgttg ctggcgtggt tgccaggttg gctcccgttt   9900
```

```
ttggccagat tattggtatg gttgctggtt tggctgcccg gctggtgcct gttattggta   9960
tgcttattgc ccggctggtt cctgttatca cccagattat tggtatggta acccaggttg  10020
ctgccatgtt gttgcctatg ctgatgccgg ttattcaggc tgttgttgct gtgatacggc  10080
aggttattgg tgtggtcatg cagttgatac ctgttttgat gccggttgtg cagcagattt  10140
tgggtgctgt catgtctgtt tgccgccga ttgttggttt gatacggtcg ctgataccgg  10200
tgatcatgtc gattatgcgt gtggtggtgc aggttgttgg tgccgtgcta caggtggtgg  10260
cccgtattat tccggttgtt atgccgattt atgtttcggt gattggattc attgccaaga  10320
tttatgctgc ggttatcgtt tttgaggcta aggttattgg cgctattctt cgtactatta  10380
cgtggattgt gaatcattca gtgtctggcg tgaggtctat gggcacggcc atccagaatg  10440
gctggaatca tatcaaatcg tttacgtcgg cgtttattaa cggtttcaag tcgatcattt  10500
ctgccggtgt tgccgcggtt gtggggtttt ttacgcggct tggtttgtcg gttgcctccc  10560
atgtgaggtc tggtttttaac gcggcccgtg gtgctgtttc ttctgcgatg aatgctattc  10620
ggagtgttgt gtcttcggtg gcgtctgctg ttggcgggtt tttcgggtcg atggcgtcta  10680
gggttcgtag tggtgctgtg cgcgggttta atggtgcccg gagtgcggct tcttctgcta  10740
tgcatgctat ggggtctgcg gtgtctaacg gtgtgcatgg tgtgctgggg ttttccgga   10800
atttgcctgg caatattagg ggcgccttgg gtagtatggg gtccctgttg gtgtcggctg  10860
gccgtgatgt ggtgtctggt ttgggtaacg gtatccggaa tgctttgagt ggcctgttgg  10920
atacggtgcg taacatgggt tcccagattg cgaacgcggc gaagtctgcg ctgggtattc  10980
attccccgtc tcgggtgttt cgtgacgagg ttggccgtca ggttgttgcc ggtttggctg  11040
aggggatcac cgggaatgct ggtttggcgt tggatgcgat gtctggtgtg gctggccgtc  11100
ttccggatgc tgtggatgcc cggtttggtg tgcgatcgtc tgtgggctcg tttacccgt   11160
acgaccggta tcggcgtgcg aacgagaaga gtgttgtggt gaatgtgaac ggacccacgt  11220
atggggatcc tgccgagttt gcgaagcgga ttgagcgtca gcagcgtgac gctttgaatg  11280
cgttggctta cgtgtgatcg agggggtgtt gtgcatgttt attcctgacc cgtctgatcg  11340
tgccggtttg actgtggatt ggactatgtt tccgttggtg ggtaatgctc cggagcgtgt  11400
gcttcatttg acgattata cggggtcgtc tccggtcatg ttgttgaatg attcgttgcg  11460
cggcctgggt atgcctgagg tggagcagtt ttctcaaacg catgttggtg tgcatggttc  11520
ggagtggcgc gggtttaatg tgaagcctcg cgaggtgact ttgccggtgt tggtgtcggg  11580
tgttgacccg gatccggtgg gcgggtttcg tgacggtttt ttgaaggcgt atgacgcgtt  11640
gtggtctgcg tttcctccgg gcgaggtggg ggagttgtct gtgaagactc ctgccggtcg  11700
tgagcgtgtg ttgaagtgcc ggtttgattc ggctgatgac acgtttacgg ttgatccggt  11760
gaaccgtggc tatgcgcgct atctgttgca tttgacagct tatgatccgt tttggtatgg  11820
ggatgagcaa aagtttcgtt ttagtaacgc gaagttgcag gattggttgg gtggcggccc  11880
tgtcggcaag aagggtaccg cgtttcctgt ggtgttaaca ccgggtgtgg gctcgggctg  11940
ggataacctg tctaataagg gtgatgtgcc tgcgtggcct gtgattcgtg ttgagggtcc  12000
tttggagtcg tggtctgtgc agattgatgg tttgcgtgtg tcttcggact atccggtcga  12060
ggagtttgat tggatcacta ttgatacgga tcctcgccag cagtctgcgt tgttgaacgg  12120
gtttgaggat gtgatggatc gtttgacaga gtgggagttt gcgcctatcc cgcctggcgg  12180
ttctaagagt gtgaatattg agatggttgg tttgggtgct attgttgtgt cggtgcagta  12240
```

```
caggtttttg agggcttggt gaatagttga tggctggtct tgttccgcat gtaacattgt   12300
ttacacctga ttatcgccgt gtggcgccta tcaattttt tgagtcgttg aagttgtcgt   12360
tgaagtggaa tggtttgtcg actttggagt tggtggtgtc gggggatcat tcgaggcttg   12420
acgggttgac gaagccgggt gcgcggctgg ttgttgatta tggtggtggc cagatttttt   12480
ctgggcctgt gcgtaaagtg catggtgtgg gtccgtggcg ttcttcccgt gtgactataa   12540
cgtgtgagga tgatattcgg ctgttgtggc gtatgttgat gtggcctgtg aattatcgtc   12600
ctggtttggt tggtatggag tggcgtgcgg acagggatta tgcccactat tcgggtgcgg   12660
ctgagtcggt tgctaagcag gtgttggggg ataatgcttg gcgttttccg cctggtttgt   12720
ttatgaacga tgatgagagt cgtggccgct atattaagga ttttcaggtg cggtttcacg   12780
tgtttgccga taagttgttg ccggtgttgt cgtgggctcg gatgactgtc acggtgaacc   12840
agtttgagaa tgcgaagttt gatcagcgtg gtttgttgtt tgattgtgtg cctgctgtga   12900
cccgacgca tgtgttgact gccgagtctg gttcgattgt gtcgtgggag tatgtgcgtg   12960
acgccccgaa ggctacttcg gtggtggttg gtggccgcgg cgagggcaaa gatcggctgt   13020
tttgcgagga tgttgattcg atggccgagg atgactggtt tgatcgtgtc gaggtgttta   13080
aggatgcccg taacacggat tccgagaatg tgcatcttat tgatgaggct gagcgggtgt   13140
tgtccgagtc gggggctacg tcggggttta agatcgagtt ggctgagtcg gatgtgttgc   13200
ggtttgggcc tggccgcctg atgccggtg atcttatcta tgtggatgtg ggctcggggc   13260
ctattgcgga gattgtgcgc cagattgatg tggagtgtga ttcgcctggt gatgggtgga   13320
cgaaggtgac tccggttgct ggggattatg aggataatcc gtcggcgctg ttggctcgcc   13380
gtgtggctgg tttggctgcg ggtgtgcggg atttgcaaaa attctaattg ttaggggttt   13440
gttgtgggta ttgtgtgtaa agggtttgat ggtgtgttga ccgagtatga ttgggctcaa   13500
atgtctggtc tgatgggtaa tatgccgtcc gtgaaagggc cggatgattt tcgtgtcggc   13560
actacgattc agggttccac ggtgttgtgt gaggtcctgc cggggcaggc ttgggctcac   13620
ggggtgatgt gcacgtcgaa tgctgttgag acggtgacag tcagcttcc gggcccgggt   13680
gagacccgct acgactatgt tgtcctgtcg cgggattggc aggagaatac ggccaagttg   13740
gagattgttc ctgggggggcg tgcggagcgt gcccgtgacg tgttgcgtgc ggagcctggc   13800
gtgtaccatc agcagttgtt ggctactttg gtggtgtcgt ctaacgggtt gcagcagcag   13860
cttgacagga gggctatagc ggcccgtgtg gcgtttgggg agtctactgc atgtgatcct   13920
accccctgtgg agggtgaccg ggtgatggtg ccttctgggg ctgtgttggc taatcatgct   13980
aacgagtgga tgctgttgtc tccgcggatt gagacgggca ctaagtcgat catgtttggc   14040
gggtctgctg tgtatgctta cacgattccg tttgatcgcc agtttgctag tccgcctgtt   14100
gtggtggcgt ctatggctac ggcggctggg ggcacgaccc agattgatgt gaaagcctac   14160
aatgtgactg cccaaaattt tagttttgcg tttattacga atgatggttc gaagccgaat   14220
ggtgtgcctg cggtggctaa ttggattgct gtcggcgtgt gactgtacag gtgttgtggc   14280
ggatggtgtg atgttggggg gctgtggtgt cgtggtttac tcctgcactg gtggcctcta   14340
tttgtaccgc gttggccacg gttttgggtt ctgttcaggc tgtcacgtct aaatctagga   14400
ggcgtttgcg ccgcctgtcg gcgcaggtgg atgcgatgga agagtatacg tggggtgtgc   14460
ggcgcgaggt gcgaaggttt aacgccgggc ttcctgacga ggtggagcct atgcatctcc   14520
ctgatttgcc cgagtttttg aaagatactg ttgatggtgg aggtgagtag ggttgaggga   14580
gttggaggag gagaagcggc agcgccgcaa ttttgagaag gcttcactgg tgttgctgtt   14640
```

```
tttgtcgctt gtgttattgg ctgtggttgc tgcgggtgct ttgcgtttcg gggctgtatc   14700
ctctgagcgg gattcggagc aggcgagggc ccagtcgaat ggtacagccg ccaagggttt   14760
agccagcagt gtgcgcagg tgtgtgctca gggtggacgg gagtctgtgc ggcttcacca   14820
gtctggtttg tgtgtggatg ctcagcgtgt tgagcgtagt gtgcagggtg tgccgggtcc   14880
tgccggtgag cgcggcccgc aaggcccggc aggtgtggac ggccgggatg gtgttaatgg   14940
ttcggctggg ctggttggcc ctgtgggtcc gcaggggtcc ccgggtttga atggtgtgaa   15000
aggtcctgac gggttgcctg cgctaacgg ttcggatggc cgtgatggtg tggacgtgt   15060 gaacggcaat gatggcgctg atggtcggga tggttcggcc ggtgagcgcg gtgatgtggg   15120
cccctcaggt cctgccggcc cgcaaggtgc acagggtgaa cggggtgagc gcggccccgc   15180
cggtgcgaat ggcacgaatg gcaaggacgg taaggatggt gccgacggcc gtgatgggcg   15240
ttcggttgtg tctgtgtact gtttcggtgg cctgccaggg tgtgaaacca tcacctgtgg   15300
ttaccgtgtc atcccgtaaa tagaagaaga gggaagggtg ttactagtgt tgattgtggt   15360
ttttggtggt ggtgtgtggt gagatacatt cctgcagcgc atcactctgc cggctctaat   15420
aatccggtga acagggttgt gattcatgca acatgcccgg atgtggggtt tccgtccgcc   15480
tcacgtaagg ggcgggcggt gtctacagca aactatttcg cttccccatc gtctggtggt   15540
tcggcgcatt atgtgtgtga tattggggag acggtgcaat gcttgtcgga gtctacgatt   15600
ggttggcatg ccccgccgaa tccgcattct ttgggtatcg agatttgcgc ggatgggggt   15660
tcgcatgcct cgttccgtgt gccggggcat gcttacactc gggagcagtg gcttgatccg   15720
caggtgtggc ctgccgttga gagggcggcg gtgctgtgta acgtttgtg tgacaaatat   15780 aatgttccga aaaggaaact gtcggctgcc gatttgaagg ctgcaggcg gggtgtgtgt   15840 ggccatgtgg atgttacgga tgcgtggcat cagtcggatc atgacgatcc tgggccgtgg   15900
tttccgtggg acaaatttat ggccgtcgtc aacggcggca gtggagatag tggggagtta   15960
actgtggctg atgtgaaagc cttgcatgat cagattaaac aattgtctgc tcagcttact   16020
ggttcggtga taagctgca ccatgatgtt ggtgtggttc aggttcagaa tggtgatttg   16080
ggtaaacgtg ttgatgcctt gtcgtgggtg aagaatcctg tgacggggaa gctgtggcgc   16140
actaaggatg ccctgtggag tgtctggtat tacgtgttgg agtgtcgtag ccgtcttgac   16200
aggctcgagt ctgctgtcaa cgatttgaaa aagtgatggt ggtttgttgt gggtaaacag   16260
ttttggttag gtttgctaga gcgggcggct aagacttttg tgcaaacgtt tgttgctgtg   16320
ttgggggtga cggcgggtgt cacgtatacg gcggagtcgt ttcgtggttt gccgtgggag   16380
tctgcgttga ttacggctac ggttgctgcg gtcctgtcgg tggctacctc gtttggtagc   16440
ccgtcgtttg tggctggtaa gccgaaaacc acgcctgtgg atgcgggttt ggttccgccg   16500
gatgatcccg gaatagtgga gcctcacatg gtggatgtgt cggatcctgg catgatcgag   16560
cctgcagatg atgtggatct tggtgtaggc tatgtgccga acatgctgcc gagtcggag   16620 gttggcacgg tagagtcgac tgttgcataa gtgaatatag atgtgtgccc cagcggtgct   16680
gccacgattg tgtggtggtt ccgctgggg cactatttt gtatattgcg gtgtggctat   16740
gattcgttgc tgtcgatggt gtcttcgagc atctggtaca ggtggaggca ggtagagata   16800
gtttcgctgg cctggtcgag aacgttccgg ccgataacat ttttgttgtt gtcgcggtgg   16860
cggatgatag accacatgat ctcgtcggct gccgcctgca atagttttgc ctggtatgcg   16920
attccagcga gccagtctag tgcttcctgg cttgcatagg gtgtctggtc ctcgctgttg   16980
```

```
cttgtggggt gtcctgcact gtcgcatagc cacaggattt cgctgcactc gtctagcgtg   17040
tcctggtcta tagcgagatc gtcgaggctg acattgttga cggtaaggtt cacgttgtcg   17100
agggagatgg gtacaccgta ctggttttcg acaccgtcaa caatgttttc caattgctgc   17160
atgttggtgg gctgttgttg gacgatacgg tgtatcgctg tgttgagggt ggtgtaggtg   17220
atattgtgtg tgttgttcat cgtgttatgc cattccttcg ttatcgtctg gcctgtagta   17280
tgtgctgttt gcgtactcgg ttaacgtcat cagtgtttgg tctgcccact gtttcacagt   17340
ctgccttgtc actccgagtc gttgggcggc tgtggcgtag gtttggtcat acccgtatac   17400
ttccctgaat gctgccaacc gtgccaaatg ttttcgctgt ttggatggct ggcaggcgag   17460
ggtgtagtcg tcgatggcta gctgtagatc gatcatggtg gcaatgttgt tgccgtggtg   17520
ttgtggcgcg gttggtgggg gtggcattcc tggctccaca ctgggtttcc atgggcctcc   17580
gttccagatc cattgggcgg cttggatgat gtctgcggtg gtgtaggttc ggttcactgg   17640
tcatcccctg aacaggttgt ctgggttgct ggtgcggatt gtgtcgaatc gtccgacgca   17700
gtggcagtag tcgtacatga gtttgataat gtgttggtgg tctcccaaat aggtgtttcc   17760
gctgatgctg taggtggctg tgccgtcttt actaatagtg tatttggcgg tgatggtttc   17820
ggggttttcg gtgtcggtga tgatggctgt ggtggtggtg cctacggttt ggagcacggt   17880
ggtttgggtt ccgtcgtcga tggtggtttt aaccatgagg tgtgttctcc ctttgtgtta   17940
gttgctggtt tggttgtcgg ctagatgaat gatgtcgggt aagggtttcg gctggtctaa   18000
atgttgtgtg gttttgttgg ctagccgttt ggctaccctg tagcacattt tggtgtagtg   18060
tttgttgtct aggttgtggt attgttcccg caccgcaata tatagcaggg agtcttggta   18120
caggtcgtct gcattgattg cggggtagtg tgcggctgtt ttagtgcatg cccggttgag   18180
tgtgcgtaga tgatggtctg tggcccacac ccacgatgcg gtggtggcta ggtcggcttt   18240
tgttggtcgt cggctcatgg catctctttc atctggctat ctggtagttg tttggtgttt   18300
tgttgttgat agtgtagcac acgagtccgg ggtttccggt ggtgcccgtc ttgtgccggt   18360
accatgtgga ttcgccttcc atggatgggc attggatgaa ggtgcgttgt ccttgttcgg   18420
agatttctag gtggtgcctg tgtccggcca tgaggatgtg ggatgtggtg ccgttgtgga   18480
attcttgtcc gcgccaccaa tcatagtgtt tgccggtgcg ccattggtgg ccgtgggcgt   18540
gtagtatccg tgtgccggct acttcgacgg tggtggtcat ttcgtctcgg ctggggaaat   18600
aaaagtgtag gttggggtat tggttggtga gctggtaggc ttctgcgatg gcgcggcagc   18660
agtctacgtc gaaggagtcg tcgtaggtgg tgactccttt gccgaagcgt acggcttctc   18720
cgtggttgcc ggggatggat gtgatggtca cgttttttgca gtggtcgaac atgtggatga   18780
gttgcatcat ggccatgcgg gtgagcctga tttgttccgt caaggggggtt tgtgtgcgcc   18840
aggcgttgtt gcctccttgt gacacgtatc cttcgatcat gtcgccgagg aatgcgatgt   18900
ggactcgttc gggtttgcct gcctgctgcc agtagtgttt agctgatgtg agggagcgca   18960
ggtagtcgtc ggcgaagtgt gatgtttccc cgccggggat gcctttgccg atttggaagt   19020
cgcctgcccc gatgacgaag gccgcagtgc tgtagtcggt gcgggtgtcc tgttcggtt   19080
ttgggggtgt ccattcggct agtttatcga cgagttcgtc tacagggtag gggtttgttg   19140
cgggttggtg gtcgatgatt ttttgtacgg atctgcctgt ttctccgttg gggagtgtcc   19200
attcggagat gcgtgtgcgg cgtacggtgc cgtttgcgag atcatcgcag atggtgtctg   19260
cttcgctatc gtggttggct agctgggtga gtagccggtc tatgttgtct atcactgggt   19320
atcctcttct tgcggggtgg tgttggcttg tttgcggcgg tagtcttta taacggtggc   19380
```

```
ggagatgggg tatcctgcct gggtgagctg ttttgctagc catgaggcgg ggatggtttt   19440
gtcggcgagc acgtcggcag ccttgttgcc gtagcgttgg atgagtgttt cagttttggt   19500
tgccatggtg tcctatcggt tgtgtggtgg gctgccatcc tgtgcggcag tcgccgtcgt   19560
ggcctggttt gcgtgtgcac cacgatacgg ttctgtctgt gtggttgagt gttttgccgc   19620
acatgacgtt ttgtagatgc tctggcagtg cgccgtcacc ctggttgctg gtttgtgtgt   19680
cgaagagtgt tttctggttg gtgaaatgct cggacacggt gccattatgt acgggtagta   19740
tccatgtttt ccattgttgt tgtagccggg tgttccagtg gaattgtttt gctgcgttcg   19800
tggcttgttt gatggttttg tagtagccga cgaggatgcg ctggtgttca ctgtcgggag   19860
ggttttggcc tcgccagtat tgtgccgcca cggcgtagcg gttgctggct gtgaaggcgt   19920
cccagcagta ttcaataatg tgttgtagta cactatcggg catgtctcgt acttggtttt   19980
cgtcgagcca cgcgtcgaca atgatgttgc gtatggcgcg tttgtctttg gtggtgggtt   20040
tgaatgcgat gctcacagta cgggcctgtc gtcttgcatg aaatcattaa aggatgattc   20100
gcttgcgcgg cgtgcttgtg tgatttgctg gtcagaccag tcggggtgtt gctgtttcag   20160
atagtaccag tggcacgcat tgtaggtttc gtcttgtagc cgggtgagat ggttttcggt   20220
gatgatttgt ttccacatag tccatgacac gtcgagccgg tccaatattt ccattgctgg   20280
aatgttgaac tggttcagga agagtatttc gtgggtgtag tattccttct cgtactggtc   20340
ccatccactt cggtgcctgt tgggctggtt tttggggtag gcttcccggc atactttgtg   20400
caaatgtttg gccatgtcgt cgggtagttt aatgtcaggg ttggcgcgga tcatggatcg   20460
catcccatca taggtggtgc cccaggtgtg catgatgtag gtggggtctt caccatcagc   20520
ccattttcct gcacagatgg cgaggcggat gcgtctcctg gctgattggc tggtgttgcg   20580
ccggttgggg atggggcacg tgtcgagggg atccatgatg ttttggtgta cctttcttgg   20640
tttaggttgc ttgtgtggtt ttattgtagc actgtgtcta gtgcttgtgt caaccctgtt   20700
ttgccggcct gaaggtaggt gtctgtgaca tcccccaggg tgaggggcac atgggtggct   20760
tgggggagtg cggcctggag tgtttgggcc atctggtggc ccgccttgtc tgggtctgac   20820
cagatgtaga tgtggtcgta gccttcaaaa aatttggtcc aaaaagtttg ccacgaggtt   20880
gcgccgggta gggctacggc tggccatccg cattgttcga ggatcatgga gtcgaattcg   20940
ccttcgcaaa tgtgcatttc ggctgccggg ttggccatgg cggccatgtt gtagatggag   21000
cctgtgtctc ctgccggggt tagatatttg gggtggttgt gggttttgca atcatgttgg   21060
agtgagcagc ggaaacgcat ttttcgtatt tcggctggcc cttcccagac ggggtacatg   21120
tatgggatgg tgatgcactg gttgtagttt tcgtggcctt ggatgggtc attgtcgatg   21180 tatccaaggt ggtggtagcg ggctgtttct tcgctgatgc ctcttgccga gagcaggtcg   21240
agtatgtttt cgaggtgggt ttcgtagcgg gctgaggctt tctggattcg gcggcgttcc   21300
gcaatgttgt aggggcgtat gctgtcgtac attcgggttt tcttcctcta atcgttgttt   21360
cagtttgtgg agtccgcctc cgataccgca tgtgtggcag taccagacgc ccttgtcgag   21420
gttgatgctc atggagggct ggtggtcgtc gtggaacggg cagaggatgt gttgctcgtt   21480
ccgtgacggg ttgtagcgta tctggtgggc gtctaggagg cggcaggtgt cagaggtgtg   21540
ggaggagctc gttgagggtt gataccacat aggcttcgct ccagggtttg ttgcgctgtt   21600
tcatgatgac gagtccgatg gtggattggt tttcgcggtt tcggtgtgtt tcgtagttgc   21660
gtgcctcccg gctggcttgt ttcacgaatt cggctaggtg tgcctgtcct gctttggctt   21720
```

-continued

```
cgatcacata ggttttgttg ccggttgtga ggatgaggtc gccttcgtct tctttaccgt   21780
tgaggtggag gcgttctata tcatagccgg tgtcgcgtag ctggtggagg agtcttgttt   21840
cccattcggc gccggctcgg cggttgcgtg cctgttgtgt tgacatgata gtcctttatg   21900
ttcttgtgtc atgttccagg gctgtttttc tactaggggc ccgaagaatg tgtattcggg   21960
gtaggctcgt agtcgttcgt attttgttcc gtctgggctg gatttgccgg ttctctgttt   22020
caggacggcg atgcgtgcct cggcggggat ggtgaggccg ttgccgttgt cttcgccacc   22080
atacagggag actcccaata tgagttgtgg ttttcggag aggccgtttt tgatttcccg   22140
cctagctggg gggtgttcga tgtcggtgcc ggttttgtcg gttgcgtggt gggtgacgat   22200
gatggtggag ccagtatctc tacctaaggc tgtgatccat tgcatggctt cttgctgtgc   22260
ctgatagtcg gattcgcagt cttggatgtc catcaggttg tctataacaa taatgggtgt   22320
gaaggtgttc cacatttcca tgtaggcttg cagttccatg gtgatgtctg tccatgtgat   22380
gggtgactgg aatgagaagg tgatgtgtcc gccgtggtgg atgctgtctc gatagtattc   22440
tggcccgtag ttgtcgatgt tgtgttgtat ctgttgggtg gtgtgttggg tgttgagtga   22500
gatgattcgt gtggaggcct cccagggtgt catgtcccct gatatgtaga gggctggctg   22560
gttgagcatc gcggtgatga acatggctag ccctgatttt tggctgccgg accgccccgc   22620
gatcatgacc aaatcccctt tgtggatgtg catgtccagg ttgtcataca agggtgctag   22680
ttggggtatg cggggcagtt cggcggctgt ttgggaggcc ctctcgaagg atctttggag   22740
agagagcatc gggaccttaa tctatctgtt ggttgggtgt gttttggtgg tcagatggag   22800
tcgatgtcga tgtcagcatc ggcgggggct gtggtgtcgt ctagctggcc gttgtcgcgt   22860
ttgtctacat attcggcaac cttatcgtag atggcgtcgt cgaggggttt gaggacgacc   22920
gcgttgaacc cgttttggt gcgcacggtg gcaagtttga aggcttgttc ttcgccgaga   22980
tatgcttcta ggtcgcggat catggagtgt gggcggtcgt tgttgccgcg tgcttttcg   23040
atgatggcgt tggggatggt ttctggggtg ccgttgttga gatcctggag ggtgtggaag   23100
attgtgacat cagcgtagat gcggtctgcg acctgtccac cgtagccttc ggtgttgtgt   23160
tctacgtcgc ggattttgaa ggcgatggcg gtggcgtcct ggtttcggga gggggttgaag   23220
aaggtgctgt tgctgttgtt gtggtagttg gcgagtgcca tgattgtgtt atcctttact   23280
gttgtgtctg tttttgttgt cttatattgg tttatcgggt gaggctgttt cgtttgctgc   23340
ggaaagcctc ggaaacgtca ctgttactgg tgatggtctt cttgtactgt ttgagtaggt   23400
ctgctagctg tgtcttgctg gtggcttgt ttatccggtc gatgatgatg tcgttttcct   23460
gtgatgcgat tttgttgacg tagtcttggg cggctttatc gtatcggtct tgaagcagga   23520
ttgctgcgct agcgatgagg gttgcagat cccagtcttt ggatacggtt tcgtctttca   23580
atcctcctag cagatcaata atggattgtt tgatgtcttc tgcggtgtct ccgcggatga   23640
ctgtccatgg ggcggcatag tcgccaccgt atttgagtgt gatagttagt tttccgctgt   23700
ctgtggtgtg ctcgtcggtc acgtgttttc cttttcgttg ttttcggctt ctggtggctg   23760
tacggtggtt tctatcgggt atctgtaggc gtctttcccg ttgacggccc agcaggcgtc   23820
cttgacgggg catcctttgc agagtgtggt gacgtggggt acgaagatgc cttggctgat   23880
tcctttcatt gcttgactgt acatggatga tacatgccgg taggtgttgt tgtcaagatc   23940
aatgagttcg gttgctgtgc cctgctcgac tgattgctcg tctcccttgg tggtggcggg   24000
tgtccaaaac atgcctttcg tcacatggat gccgtgttgg gcgagcatgt accggtatgt   24060
gtgcagctgc atactgtctg cgggtaggcg tccggttttg aggtccaaaa tgaaggtttc   24120
```

```
gccggtgtcg gtgtcggtga atacccggtc aatatatccg actattttg tgtcatcgtc    24180
gagggtggtt tctaccgggt attcgatgcc tggctggccg tcaataacag cggtggcgta    24240
ttctgggtgg ttgcgcctcc atgttttcca gcggtccaca aaggtggggc cgtacatcat    24300
ccaccaattg tagtctttct tgtgtggccc gcctgactcg cacatgtttt tgcatattct    24360
gccggagggc tttatgtttg tgccttcgga ttcggcgagg gcgatttggg tgtcgaaaat    24420
gtttgtgaag gatgagagtt tgtctggcag tgcagggtat tcggcggggt tgtacaggtg    24480
taggtcgtat tgttcggtga tgtggtgtat ggcgcttccg gcgatggtgg cgtaccaggt    24540
gtggtgttgg gcgtggtagc cgtgtgctag gcgccatttt tcgccgcatt cggcccactg    24600
tgtgagtgaa ctgtaggaga tgtggcctgg atggttgatg gttttcgggt attgtgctag    24660
gggcattact tgtcgccttt tgggtgttc catgggttgc gggtgtcttt gccggcgtgg    24720
tgttgctggt aggcgaggag tgcgaggcag tgccaggcag cgtgtgccag atgcggcaaa    24780
tgtgattcgt tgtcgaggtt gttgccttgc tgccatgata acaggtgccg gtagagggcg    24840
tcgacactgt ggctccacgg gtatcctccg gtccagttgt tgtcgccgta cttggtggca    24900
ccgtagcctg ccacggagcc tagggcgtgc aaggctgcgg ggtcgatgag ggagagcctg    24960
cagagtttca attcttttcg ggcaccgctg ttggggtcgg tgtacatgct ggtgggctca    25020
tccatggtgt gtgtgctcct taagcgtggg ttactggtta ttgtcgtggg cgagtgctac    25080
ggcgagaata atgatggcga gggtttcagc gatcagtatg ggtgttgtga tcatttagtg    25140
tctcggggat tattggtgag tgttgatgca cctaggaggg tggcgagggc gcatgcggcg    25200
atggtggcga gggctgcctt tgtgggggtg ccggttgcgt acatccatgt gatgatgccg    25260
ccttggatcc aggctagact ggtgaagaac gtttcgtaac tgtgtagctc aatgttgttg    25320
ttgggtgtgt tcatgcttgc tcctgaagaa tggtgttgat ggttttataa atgttgtaca    25380
ggtcggtttc gatagataac agttggttga tttggtggtc gagatcaatg tctgggttga    25440
gggtgtcgat gcgggcggcg atatcggtgg cggtgcgtag gcttactgct gcaccgtgga    25500
tgatgtggca catgtcggtg aggccgactt tggcgatata gtgtgacatg agaggcataa    25560
taggtgtgct gtctttctgg tcagcgtgaa gggttgatgg acatatcctc tacctgtggt    25620
ttgtcttcgg tgccggagac ttggcagaag actttcacat gcgtcttgga tgctccggcc    25680
tgtttggcgg tggcaccgta ggcgatagta aaggtgtctt tgtgggcgcc gatgactttg    25740
tgtaggaaga ggtcgatgtc gggttgccg ttccatttga caccgttttc tgcggctgtc    25800
tgggtggctt tctgattgca ggcgtgtgcg gcggtgatca tggtgagacc cttgctggtt    25860
tcttcacccc ttgcttgggc ttgccggtgg gctttggcct gctcggcttg tagggagcgg    25920
actgctgcgg cctggcgggc cttcttctca gccttgcgct gctggacggt tttgggtgtc    25980
cattcggtgt tggctgtggt tacctgtggt gcgggttgtg aggcgagtgg cggattgtcg    26040
tctggggctg gcatgaagga tgctgcggca ataatggcga ctgtggcgcc tgcgatggtc    26100
tagcctgttt tcttgttcat gatttatgt tcccctttcc ggggtgttgt tcgttgctga    26160
catggttaat actttcagcg gctgggccca ctgtcaaggc tgcgctcagt ttgtgtgagc    26220
gtttcttgtg tggctagggg tgatggcttc tttcgcccaa taggatgtgc caccgctggt    26280
ccagtatccg agtttgttgc gctgcatgcc cttggcgtcc atctcgtcga tagtgaggca    26340
cctgcggcga ttggggcctg tcttgacccc gtggtcgcct gtccggtgca tgtcgcctga    26400
ggtggtactc gtgaatgttt catggcagat ggtacagtgc tctggtcgat atccggtgat    26460
```

```
tgtgctatcg cacttgtggc atgtccattc catgattgct cctatttcc attataagac   26520
ttcctgtagt gccattttag cgccttgcgg gtcttggggg tacaactata taggtcaggt   26580
gtttctaggc gattctaggc tcattgtgtg tggctgggt tttatcgggc acacagggtg    26640
agcaggtggc caacattgat gcgggtcaca ttccagtaga gttgcgtggc ttccccactg   26700
gtgagcggct tccactcgtc atggctgaac acggtgccat cggatgcgat gaacgtgttg   26760
gggcgtagct tgtggagttc ggcttccacg ctctgccggt aggcttcggc gaggccctca   26820
aaatccatgt ggtcgcaggg gaggttttcg aggcgtgtca ggtcgaaggg tgtggggcag   26880
tcgtagctgg cggggtgta gagctgggtg aagtggttgg cgatcttctg catcatgatt    26940
cctttctga tgatggtgtg ttgagggttt atcgggtgga tgcgacaagg atggcgtcta    27000
catcgatcat gtcgatgaga tcgtggagtt cctcggcctc gttctcagtg agtggctgcc   27060
aggcgtagtc gccgtatacg cgccgtcga gggtgacagt ccacgggggc cggatgagtc    27120
gtatggcttc ttgtacttta gcgtggtaca tgcggcgcac catatccaga tcgatgtcgt   27180
ctgaatggtt tccggtgagg ctgtggaggc tgagcgggtc gatgtctgtc tgcctgtaga   27240
gggatgtgaa ggatggggtg atgagtgtgc catccatgag tgtgctcctt tcggtggttg   27300
taggggttgt tgtggtttct agagtgtgcg ggctgcgacc ccacagtcaa ggtgtcgctc   27360
aaactcagtg agcgtttcat atgggtgtgt tgggtgtgac agatgtcact taagccttga   27420
tggcctctct cagcgcctca aatcttctag gggtaggatt atgaagggtt ggccctgctg   27480
atcgattcta ggccccatac agggcgtctg aggggtgtgt ctgagtgata gtgggtgtgg   27540
cagatgatct agcgagtcaa ggtgccgagc tgagacataa gatctatcat ctaggtgtgt   27600
gagatgtatc acatcctccc ggcttggtgt gcaccctcaa ggccacccag tcgatctgac   27660
gtggagggtg tagcccagaa atactgttta aagccttcac acggcgccta ggagcgcctt   27720
acagggtggg ggctaggtat ttataccccc agcacattct gatcgattct agacgcctac   27780
aggagcccga tacacgatca gccatccaga cgcagatcat cagcacctat catggttagc   27840
taagcctcaa ctatgtggac agtgttggtt actgtggggg aagaaggaca cggtaaaaga   27900
aagaggggga gtatcagctt taaagcctta aggtcttagc gcttagcacc gatggtctta   27960
gcagttagca ccgagccccc tcaagggctc ggcatcagcc cgaacaggca cagccatgaa   28020
aggagtacac gccatcaggg aaggctttcg agtacgagga gcctcagcga cgagtactcg   28080
aaagcctgag ggaacaccca tcagcactga tgagcctagc gtattcggaa aggacacaag   28140
agtgaagtgt gacagctgtc cgggagtgaa ccccgttctg actaggggtt tcagccttaa   28200
ccaccctcaa aggttacaag actctaagaa aatttaagga aagtttagg tttaattttt     28260
ggaccttac taccaaaaac acccgtttac agccctcaaa cccgcctata gagccaaaac     28320
caccagtttg actcatccca ggtggggtat gataggctgg acaggtagcc agctggacgc   28380
aaggccggaa agtgctaacg cactttccaa cctcgcttac catcagtcta ccaaacactt   28440
aaagacctaa gggcttagcg ctaaggtgct gatagcttag caccgagccc cctcaagggc   28500
tcggcatcag tcttaaagcc ttaaatactt aaagtaacta taaaacttta aaagcttaac   28560
acttaaggat ataaactta catcagtgtt taagacttaa aaacttaaaa taactattaa    28620
gacttaaagt aactataaaa cattaaagac cttaagtact taaagttaac catcagtctt   28680
aaactttact atgataacct ataagtctta aagcttatag gtataataat ataatataag   28740
tattaaagct tataagttat aaaagttta gaagagttaa agggtaact tctttacttc     28800
tcttctctct ttggttcttt ctctcttctc ttcttttctt catcggggga gaagaggaac   28860
```

```
ctttaacgtc aacgctgatg gacttttcgc cgtgtgtctc gtgtgcttct ggtcgcaagc    28920
tcccatcgca cactccccac actctttcac ctgtgtccct ttcaggctta gcgtgttcag    28980
ctgaaggcgt acagcgtgtc acgcttaaac ccttaacacc aggtaagact taaagtgcat    29040
attataagta gaagacttta aaaccttaag ggtgttcctg cttagcctgt gtcctttaac    29100
gctaggcgct aagccgtgaa acgtgaacac ccatccaccc ctcttctttt taccgtgtcc    29160
ttcttctttt gacaccgctg gggggcgatg tgatctttt  aacatgccag ggggtgcggg    29220
tagaaaacaa ccaccccacc acaaacagaa caccccctca aacgcacaaa acagccccca    29280
ggatcgatga acagggcaag ggcaaggtat tcataccccc agacgattcc aggccgttag    29340
agaggcaaat aagacccgta cagggctagg tgaggaatag acatcatg   gcacgcacca    29400 atcgcacagc tagccaagcc caccgacgct ggcggcaacg actcatcacc caagcccaac    29460
aacaaggcca aaccgaatgc ccactctgcg gagtcaccat cacctgggac acacgaccc    29520 taccaaccag ccccgaagcc gaccacatca cacccgtcag caggggagga ctcaacaccc    29580
tcgacaacgg gcaaatcatc tgcagaacat gcaacagaag caaaggcaat cgcagcgaac    29640
caaacatcaa attccaacaa caaaccacaa aaacattgat tccatggtga caaacccgcc    29700
aacccccacc ggggacaccc cctgcacagg cgtgcaaga                          29739
```

<210> SEQ ID NO 2
<211> LENGTH: 863
<212> TYPE: DNA
<213> ORGANISM: Bacteriophage PA6

<400> SEQUENCE: 2

```
ggtgtgtggt gagatacatt cctgcagcgc atcactctgc cggctctaat aatccggtga     60
acagggttgt gattcatgca acatgcccgg atgtggggtt tccgtccgcc tcacgtaagg    120
ggcgggcggt gtctacagca aactatttcg cttccccatc gtctggtggt tcggcgcatt    180
atgtgtgtga tattggggag acggtgcaat gcttgtcgga gtctacgatt ggttggcatg    240
ccccgccgaa tccgcattct ttgggtatcg agatttgcgc ggatggggt  tcgcatgcct    300 cgttccgtgt gccggggcat gcttacactc gggagcagtg gcttgatccg caggtgtggc    360
ctgccgttga gagggcggcg tgctgtgta  gacgtttgtg tgacaaatat aatgttccga    420
aaaggaaact gtcggctgcc gatttgaagg ctggcaggcg gggtgtgtgt ggccatgtgg    480
atgttacgga tgcgtggcat cagtcggatc atgacgatcc tgggccgtgg tttccgtggg    540
acaaatttat ggccgtcgtc aacggcggca gtggagatag tggggagtta actgtggctg    600
atgtgaaagc cttgcatgat cagattaaac aattgtctgc tcagcttact ggttcggtga    660
ataagctgca ccatgatgtt ggtgtggttc aggttcagaa tggtgatttg ggtaaacgtg    720
ttgatgcctt gtcgtgggtg aagaatcctg tgacggggaa gctgtggcgc actaaggatg    780
ccctgtggag tgtctggtat tacgtgttgg agtgtcgtag ccgtcttgac aggctcgagt    840
ctgctgtcaa cgatttgaaa aag                                           863
```

<210> SEQ ID NO 3
<211> LENGTH: 29275
<212> TYPE: DNA
<213> ORGANISM: Bacteriophage 103609

<400> SEQUENCE: 3

```
cctcccttt  gtggattgtc tgtttgtcga cttttttgtgt tggtggtgag tgctgtgcag     60
```

```
cctgagcttc ctgggtctcg tgagtggtgt ggggagacgc gtcgttggtg gcgtgtgtgg    120
ggtgaggata gccgtgcatc gtacgtgtct gatgaggagt ggctgtttct cttggatgct    180
gcggtgattc atgattgtgt gtggcgtgag ggtcgcgcgg atttggtggc ttcgcttcgt    240
gctcatgtga aggcttttat gggtatgttg gatcggtatt cggttgatgt ggcgtctggt    300
ggccgtggtg ggggttctgc ggtggcgatg attgaccggt atcggaagcg taaaggggcc    360
taatgtcgag tgtggttggt tctcaggtgc ctcgtcatcg ggtggctgcg gcgtattcgg    420
tgtctgctgg cggtgatgct ggggagttgg gtcgtgcgta tgggttgacg cctgatccgt    480
ggcagcagca ggtgttggat gattggctgg ctgtcggtag caatggcagg cttgcttcgg    540
gtgtgtgtgg ggtgtttgtg cctcgccaga atggcaagaa tgctattttg gagattgtgg    600
agttgtttaa ggcgactatt cagggtcgcc gtattttgca tacggctcac gagttgaagt    660
cggctcgtaa ggcgtttatg cggttgaggt cgttttttga aatgagcgg cagtttcctg     720 acttgtatcg tatggtgaag tcgattcggg cgacgaatgg tcaggaggct attgtgttgc    780
atcatccgga ttgtgccacg tttgagaaga agtgtggctg cagtggttgg ggttcggttg    840 agttgtggc tcgttctcgg ggttctgctc gcgggtttac ggttgatgat ttggtgtgtg     900
atgaggctca ggagttgtcg gatgagcagt tggaggcttt gcttcctacg gtgagtgctg    960
ccccgtctgg tgatcctcag cagatttttcc ttggcacgcc gcctgggccg ttggcggatg   1020
gttctgtggt gttgcgtctt cgtgggcagg cttttgtctgg tggtaaaagg tttgcgtgga   1080
cggagttttc gattcctgac gagtctgatc cggatgatgt gtcgcggcag tggcggaagt   1140
tggcggggga tacgaatccg gcgttggggc gtcgcctgaa ttttgggacc gtaagcgatg   1200
agcatgagtc gatgtctgct gccggttttg ctcgggagcg gcttggctgg tgggatcgtg   1260
gccagtctgc tacgtctgtg attccggcgg ataagtgggc tcagtctgcg gtggatgagg   1320
cgaagctttc tggcgggaaa gtgtttggtg tctcgttttc tcgttcgggg gatcgtgtcg   1380
cgttggcggg tgccggccgg actgatgctg gtgttcatgt tgaggttatt gatgggctgt   1440
cggggacgat tgttgatggt gtgggccggt tggctgactg gttggcggtt cgttggggtg   1500
atactgaccg gatcatggtt gccgggtctg gtgcggtgtt gttgcagaag gcgttgacgg   1560
atcgtggtgt tccgggccgt ggcgtggtgg ttgccgatac tggtgtgtat gtggaggctt   1620
gtcaggcgtt tcttgagggt gttcgttcgg gtgttgtgtc tcatcctcgt gctgattctc   1680
gccgtgacat gttggatatt gctgtgaggt cggctgtgca gaagcgtaag gggtctgcgt   1740
ggggttgggg ttcctcgttt aaggatggtt ctgaggttcc tttggaggct gtgtcgctgg   1800
cgtatcttgg tgcgaaaaca gttaaagtga agcggcgtga acggtctggt aggaagcggg   1860
tgtctgtggt atgaacgtgg acgagttggc tctgattgag ggcatgtacg atcgtatcca   1920
aaggttgtct tcgtggcatt gccgtattga gggctactat gagggctcga gccgggtgcg   1980
tgatttgggg gtggctattc ctccggagtt gcagcgtgtg cagactgtgg tgtcgtggcc   2040
tggtatagct gtggatgctt tggaggagcg tctggattgg cttggctgga ctaatggtga   2100
cggctacggc ctgatggtg tgtatgctgc gaatcggctt gctacggctt catgcgacgt    2160
ccaccttgat gcactaattt ttgggttgtc gtttgttgcg atcattcctc atggtgatgg   2220
tacggtgtcg gttcgtccgc agtcaccaaa gaattgtacg ggcaagtttt cggctgacgg   2280
gtctcgtttg gatgcgggtt tggtggttca gcagacgtgt gatcctgagg tggttgaggc   2340
tgagcttttg cttcctgatg tgattgttca ggtggagcgg cggggttcgc gtgaatgggt   2400
tgaggtggat cgtataccga atgtgttggg tgctgttccg cttgtgccta ttgtgaatcg   2460
```

-continued

```
tcgccgtacg tctaggattg atggccgttc ggagattacg aggtctatta gggcttacac    2520
ggatgaggct gttcgcacac tgttggggca gtctgtgaat cgtgattttt atgcgtatcc    2580
tcagcgttgg gtgactggtg tgagcgcgga tgagttttca cagcctggct gggtcctgtc    2640
gatggcttct gtgtgggctg tggataagga tgatgatggt gacactccga atgtggggtc    2700
gtttcctgtc aattcgccta caccgtattc ggatcagatg agactgttag cgcagttaac    2760
tgcgggtgag gcggctgttc cggaacgcta tttcgggttt atcacgtcta acccacctag    2820
tggggaggct ttggctgccg aggaatctcg gcttgtgaag cgtgctgagc ggcgtcaaac    2880
gtcgtttggt cagggctggc tgtcggttgg ttttttggct gccaaggcgt tggattctcg    2940
tgttgatgag gccgattttt ttggtgatgt tggtttgcgt tggcgtgatg cttcgacgcc    3000
tacccgggcg gctacggctg atgctgtgac gaagcttgtt ggtgccggta ttcttccggc    3060
ggattctcgg atggtgttgg agatgttggg tttggatgat gtgcaggttg aggctgtgat    3120
gcgtcatcgt gccgagtctt cggatccgtt ggcggcactg gctgggcta tttctcgtca    3180 aactaacgag gtatgatagg cgatggcttc gggtgctgtg tcgaggcttg ttgcgactga    3240
gtatcagcgt gaggcggtca ggtttgctgg gaagtatgcg gggtattatt cggagcttgg    3300
tcgtttgtgg cattccggga agatgacaga tgtgcagtat gtgcgtttgt gtgtggagtt    3360
ggagcgtgcc ggccatgatg gttcggcatc gttggctgcc aggtttgtgt cggattttcg    3420
ccggttgaat ggtgtggatc cgggtttgat tgtgtatgac gagtttgatg ctgcggcggc    3480
tttggctagg tcgttttcga ctatgaagat tcttgagagt gacccggata gggcgaatga    3540
cacgattgat gcgatggctg cgggttttga tcggctgtt atgaatgctg gccgtgacac    3600
ggttgagtgg tctgcgggtg cgcagggtag gtcgtggcgc agggtgactg atggtgatcc    3660
gtgtgctttt tgtgccatgt tggctacgag gtcggattat acgactaagg aaagggcact    3720
cacttccggt catacgcggc gtcataagcg tggtggtaag cgtccgtttg gttcgaagta    3780
tcatgatcat tgtggttgta cggtggttga ggttgttggc ccttgggaac caaatagggc    3840
tgatgccgag tatcggagga cgtatgagaa ggcccgtgag tgggttgatg atcatggggtt   3900 gcagcagtcg cctggcaata ttttgaaggc tatgcgtact gttggtggca tgagataatt    3960
tgatgtggtt tccggttgtg cgccgccggt tattggtgca cagggttgtc tcccgcacgg    4020
gggtcaacaa tgttgtgttg ttttccgcaa ggagtgtagg gttaggctat ggccgatcag    4080
agtgttgagg aacagaatgt tgacaatgat gctgttgagc ccggaaaggg tggagacatt    4140
gttgatgttg tgaaggatgg gcaggctgcc ggcgatgatc atgccggtga tgtttccgtg    4200
aagggtgagg cttctgggcc gtctgggact gattggaagg cggaggcccg taagtgggag    4260
tctcgtgcta aaagtaattt cgccgagttg gagaagcttc gtacatcgag tgacgattct    4320
ggatctacta ttgatgagct tcgccgcaag aatgaggaac tcgaagacag gatcaacggg    4380
tttgttcttg agggtgtgaa gcgcgaggtg gcttcagagt atggtttgtc cagtgatgcg    4440
atcgctttct tgtcgggtgg cgataaggag tcgcttgccg agtctgcgaa agctttgaag    4500
ggtttgattg accatagtag tggtggcgcg ggtgtgcgcc gtcttgcggg gagtgccccc    4560
gttgatgatg ttaaacgacg tgagggtgtc gcgtttgtgg atgctcttgt caataattct    4620
aggagatgat ttctgatggc tgacgatttt ctttctgcag gtaagcttga gcttcctggt    4680
tctatgattg gtgcggttcg tgaccgtgct atcgattctg gtgttttggc gaagctttcg    4740
ccggagcagc cgactatttt cggcccggtg aagggtgccg tgtttagtgg tgttcctcgc    4800
```

```
gccaagattg ttggcgaggg cgaggttaag ccttccgcgt ctgttgatgt ttcggcgttt    4860
actgcgcagc ctatcaaggt tgtgactcag cagcgtgtct cggacgagtt tatgtgggct    4920
gatgctgatt accgtctggg tgttttgcag gatctgattt ccccggctct tggtgcttcg    4980
attggtcgcg ccgtggatct gattgctttc cacggtattg atcctgccac tgggaagcct    5040
gccgcggctg tcaaggtgtc gctgataag acgaagaaga cggttgatgc caccgattcc    5100
gctacggctg atctggtcaa ggctgtcggc cttatcgctg gggctggttt gcaggttcct    5160
aacggtgttg cttttggatcc ggcgttctcg tttgctctgt ctactgaggt gtatccgaag    5220
gggtctccgc ttgccggtca gccgatgtat cctgccgccg ggtttgctgg tttggataat    5280
tggcgtgggc tgaatgttgg tgcttcttcg actgtttcgg gtgccccgga gatgtcgcct    5340
gcctctggtg ttaaggctat tgttggtgat ttctctcgtg ttcattgggg gttccagcgt    5400
aacttcccga tcgagctgat cgagtatggt gacccggatc agactggccg tgacttgaag    5460
ggccataatg aggttatggt tcgtgccgag gctgtgctgt atgtggctat cgagtcgctt    5520
gattcgtttg ctgttgtgaa ggagaaggct gccccgaagc ctaatcctcc ggccgagaac    5580
tgatttattg ttgcggtgat gtgtcaatgt gcaggggtg gtgttgatgg gtatcatttt    5640
gaagcctgag gatattgagc cttttcgccga tattcctaga gagaagcttg aggcgatgat    5700
tgccgatgtg gaggctgtgg ctgtcagtgt cgccccctgt atcgctaaac cggatttcaa    5760
atacaaggat gccgctaagg ctattctgcg cagggctttg ttgcgctgga atgatactgg    5820
cgtttcgggt caggtgcagt atgagtctgc ggtgtcctttc gctcagacta cacggtctag    5880
tactcccacg aatttgttgt ggccttctga gattgccgcg ttgaagaagc tgtgtgaggg    5940
tgatggtggg gctggtaaag cgttcactat tacaccgacc atgaggagta gtgtgaatca    6000
ttctgaggtg tgttccacgg tgtggggtga gggttgctcg tgcgggtcga atattgacgg    6060
ctacgctggc cctttgtggg agatatgata tgaccagttt tccttatggt gaaacggttg    6120
tgatgcttca accgactgtt cgtgtcgatg atcttggtga caaggttgag gattgggagc    6180
atcctgtaga aaccgtgtac cataacgtgg ccatctatgc ttccgtttcg caggaggatg    6240
aggccgcggg gcgtgactct gactatgagc attggtcgat gctgttcaag cagcctgttg    6300
tgggcgctga ttatcgttgc aggtggcgta tccggggtgt tgtgtgggag ctgacgggt    6360 ctcctatggt gtggcatcat ccgatgtctg gctgggatgc tggtacgcag gttaatgtga    6420
agcgtaagaa gggctgatgg gtagtggctc aggatgtgaa tgtgaagctg aacttgccgg    6480
gtattcgtga ggtgttgaag tcttctgggg tgcaggctat gttggctgag cgtggcgagc    6540
gtgtcaagcg tgcggcctcg gcgaatgtgg gcggtaacgc tttcgataag gcccaatacc    6600
gtaatggttt gtcgtcggag gtgcaggttc accgtgttga ggctgtcgct cgtataggca    6660
ccacatataa gggtgggaag cgtattgagg cgaagcatgg cacgttggct cgttcgattg    6720
gggctgcgtc gtgatcgtct acgatgaccc caggaagtgg gctaaacgcg tgctcaagga    6780
tgatggctgg ctgtctggga taccgtgtac ggggacggtg cctgaccggt ttgagggtga    6840
ccttatttgg ttggctcttg atggtggccc gcagttgcat gttcgtgagc gagtgttttt    6900
gcgggtgaat gtgttttctg atacgccgga tcgtgctatg tcgttggcgc gtcgtgttga    6960
ggctgttctg gctgacgggg tggacggtga ccctgtggtg tactgtaaac ggtctactgg    7020
tcctgatttg ctggttgatg gtgcacgttt tgatgtgtat tcgctgttcg agctgatatg    7080
taggccggca gagtctgaat aagcttattg ttttgtttt aatgtaattg tttgatattt    7140
aatgggggtt gtgatggctg caacacgtaa agcgtctaat gttcgctctg ctgttactgg    7200
```

```
tgacgtgtat attggtgacg cgcacgccgg tgacactatt gatggtgtga agacggttcc   7260
ttctgggctt accgcgttag ggtatctgtc ggatgacggg tttaagatta agcctgagcg   7320
taaaacggat gatttgaagg cttggcagaa tgcggatgtt gttcgcacgg tggctacaga   7380
gtcgtctatc gagatttctt tccagctgat cgaatccaag aaagaagtta ttgaactgtt   7440
ttggcagtcg aaggttactg ccggatccga ttcgggttcg ttcgatattt ctcctggtgc   7500
caccactggc gtgcacgctt tactgatgga tattgtggat ggcgatcagg ttattcgcta   7560
ctatttcccc gaggttgagc tcattgatcg tgacagagatc aagggtaaga atggcgaggt   7620
gtatgggtat ggtgtgacgt tgaaggcgta tcctgcccag attaataaga agggtgatgc   7680
ggtgtctggt cggggtgga tgacggcttt aaaagctgat actcctccga ctcctcctcc   7740
ggccccggtt cctccgaagc ctgagcctga tccgaatccg ccgtctaata actgatacac   7800
atagtttgag ggattgttga tagatgagtg acacaggtta cacgttgaag attggtgacc   7860
gtagctgggt gttggcggat gcggaggaga cggctcaggc tgttcctgcc cgtgtgtttc   7920
gtcgtgcagc taagattgcc cagtcggggg agtctgcgga tttcgcccag gttgaggtga   7980
tgttttctat gctagaagcg gccgccccgg ctgatgcggt ggaggccctg gaggggcttc   8040
ctatggttcg tgttgccgag attttccgtc agtggatgga atacaagcct gacggtaagg   8100
gtgcctcgct gggggaatag tttggctcca cggcctgatt gatgattatc gtggggccat   8160
cgaatacgat ttccgcacca gtttggtgt ttctgtttat agtgttggtg gcccgcagat   8220
gtgttggggt gaggctgtcc ggctggctgg cgtgttgtgt accgatacgt ctagccagtt   8280
ggcggcccac ctgaatggtt ggcagcgccc gtttgagtgg tgcgagtggg ctgtgctgga   8340
catgctggat cattacaggt ctgctaatag tgaggggcag ccggagcctg tggcgaggcc   8400
tacggatgag cgtagggccc ggtttacgtc ggggcaggtg gacgatattt tggcgcgtgt   8460
tcgtgctggt ggcggggtgt ctcgcgagat taatattatg gggtgaatag tgtatgtctg   8520
gtgagattgc ttccgcatat gtgtcgttgt atacgaagat gcctggtttg aaggctgatg   8580
ttggtaaaca gttgtcgggt gttatgcctg ctgagggtca gcgttcgggt agtctttttg   8640
ctaagggcat gaagttggcg cttggtggcg cggcgatggt gggtgctatc aatgttgcta   8700
agaagggcct caagtcgatt tatgatgtga ctattggtgg cggtattgct agggcgatgg   8760
ctattgatga ggctcaggct aagttgactg gtttgggtca cacgtcgtct gatacgtctt   8820
cgattatgaa ttcggctatt gaggctgtta ctggtacgtc gtatgcgttg ggggatgcgg   8880
cgtctacggc tgcggcgttg tctgcttcgg gtgtgaagtc tggcgggcag atgacggatg   8940
tgttgaagac tgtcgcggat gtgtcttata tttcgggtaa gtcgtttcag gatacgggcg   9000 ctattttttac gtctgtgatg gcccgcggta agttgcaggg cgatgacatg ttgcagctta   9060
cgatggcggg tgttcctgta ctgtctttgc ttgccaggca gacgggtaaa acgtcggctg   9120
aggtgtcgca gatggtgtcg aaggggcaga ttgattttgc cacgtttgcg gctgcgatga   9180
agcttggcat gggtggtgct gcgcaggcgt ctggtaagac gtttgagggc gctatgaaga   9240
atgttaaggg cgccctgggt tatcttggtg ctacggctat ggcgccgttt cttaacgggt   9300
tgcggcagat ttttgttgcg ttgaatccgg ttatcaagtc tatcacggat tctgtgaagc   9360
cgatgtttgc tgccgtcgat gctggtattc agcgtatgat gccgtctatt ttggcgtgga   9420
ttaatcgtat gccgggcatg atcacgagaa tgaatgcaca gatgcgcgcc aaggtggagc   9480
agttgaaggg cattttttgcg agaatgcatt tgcctgtccc taaagtgaat ttgggtgcca   9540
```

```
tgtttgctgg cggcaccgca gtgttcggta ttgtggctgc cggtgtgggg aagcttgtcg      9600
cggggtttgc cccgttggcg gtgtcgttga agaatctgtt gccgtcgttt ggtgctttga      9660
ggggtgccgc cggcgggctt ggcggcgtgt ttcgcgccct gggtggcccc gtcgggattg      9720
tgatcggctt gtttgctgcc atgtttgcca ctaacgccca gttccgtgcc gctgttatgc      9780
agcttgtcgg ggttgttggc caggcttttgg gccagattat ggccgctgtg cagccgctgt      9840
ttggttttggt ggctggtttg gtggcacggt tggctcccgt ttttggccag attattggtt      9900
tggttgccgg tttggctgcg cagcttgtgc ctgtgattag tatgctggtt gctcggctgg      9960
ttcctgtgat cacgcagatt attggtgcgg tgacacaggt tgccgcaatg ttgttgccgg     10020
tgttgatgcc ggtgttgcag gctgttgttg ctgtgatacg gcaggttgtt ggcgtgatca     10080
tgcagttggt gcctgttttg atgcctgtga ttcaacagat tttgggtgcg gtcatgtctg     10140
ttctgccgcc tatcatcggt ctgatccggt cgttgatacc agtcatcatg tcgattatgc     10200
gtgtggtggt gcaggttgtt tcggttgtgc tgcaggtggt ggcccgcatt attccggttg     10260
tgatgccgat tgtgacagct gtgatcgggt ttgttgcccg tattgttggt gctgtcgtgt     10320
cggctgttgc ccgtgttatt gctgctgttg cccgtgttat cgggtgggtt gtggcccatt     10380
ttgtgtctgg tttggcgcgt atgggttcgg ttattcaggc tggctggaat catattagag     10440
cgtttacgtc tgcgtttatt aacggtttca agtcggttat ttctgccggt gttgccgcgg     10500
ttgtggggtt ttttgcccgg cttggttctt cggttgcttc tcatgtgagg tctggttttta     10560
acgcggctcg tggtgctgtt tcttctgcga tgaatgctat ccggagtgtt gtgtcttcgg     10620
tggcgtctgc tgttggcggg ttttttcagtt cgatggcgtc tagggttcgt agtggtgctg     10680
tgcgcggttt taatggtgcc cggagtgcgg cttcttctgc tatgcatgct atggggtccg     10740
ctgtgtctag tggtgtgcat ggtgtgctgg gttttttccg gaatttgcct ggcaatattc     10800
ggcgtgcgct tggtaatatg gggtccttgt tggtgtctgc tggccgtgat gtggtgtctg     10860
gtttgggtaa tggtatccgg aatgctatga gtggcttgtt ggatactgtg cgtaatatgg     10920
gttctcaggt tgctaatgcg gcgaagtcgg tgttgggtat tcattcccg ctctcgggtgt      10980
ttcgtgacca ggttggtcgc caggttgttg ccggtttggc tgagggtatt actgggaatg     11040
ctggtttggc gttggatgcg atgtcggtgt tggctggtcg gcttccggat gctgtggatg     11100
cccggtttgg tgtgcgatcg tctgtgggct cgtttacccc gtatggcagg tatcagcgtg     11160
ctaagggtga gagtgttgtg gtgaatgtga atggacctac gtatggtgat cctaacgagt     11220
ttgcgaagcg gattgagcgg cagcagcgtg acgctttgaa cgcgttggct tacgtgtgat     11280
tgggggtgtt gttcatgttt cttcctgacc cgtctgatcg ttctggtttg actgtgacgt     11340
ggtttatgga tccgctgttt ggtggggagc gtgtgcttca tttgacggat tatacggtgtg     11400
cgtctcctgt catgttgttg aatgattcgt tgcgcggttt gggtgttccc gaggtggagc     11460
attttttctca aacacatgtt ggggtgcacg gctcggagtg gcgcgggttt aatgtgaagc     11520
ctcgcgaggt gacgctaccg gtgttggtgt cgggtgttga cccggatccg gatggcgggt     11580
ttcgtgacgg ttttttgaaa gcctatgacg agttgtggtc tgcttttcct cctgcgagg     11640
aggggggagtt gtcggtgaag accccgtctg gtcgtgagcg tgtgctgcgg tgccggtttg     11700
attcggctga tgacacgttt acggtggatc cggtaaatcg tggctatgcg cgctatctgt     11760
tgcatttgac agcttatgac ccgtttttggt atggggagga gcaaaagttt cgtttcagta     11820
acgctaagtt gcaggattgg ctgggtgcg gccctgtcgg caaggatggc acggcttttc      11880
ctgtggtgtt gacgcctggt gttggttctg gctgggataa tctgtctaat aagggtgatg     11940
```

-continued

```
tgcctgcgtg gcctgtgatt cgtgttgagg ggcctttgga gtcgtggtct gtgcagattg      12000
atggtttgcg tgtgtcttcg gattatcctg tcgaggagtt tgattggatc acgattgata      12060
cggatcctcg ccagcagtct gcgttgttga atgggtttga ggatgtgatg gatcgtttga      12120
aggagtggga gtttgcgcct atcccgcctg gcggttctaa gagtgtgaat attgagatgg      12180
ttggtttggg tgccattgtt gtgtcggtgc agtacaggtt tttgagggct tggtgaatag      12240
ttgatggctg gtcttgtccc gcatgtaacg ttgtttacgc cggattatcg ccgtgtggcg      12300
cctatcaatt tttatgagtc gttgaagttg tcattgaagt ggaatggttt gtcgacgctg      12360
gagttggtgg tgtcggggga tcattccagg cttgacgggt tgactaggcc gggtgcgcgg      12420
cttgtggttg attatggtgg tggccagatt ttttctgggc ctgtgcgtaa ggttcatggt      12480
gtgggtccgt ggcgttcttc gcgggtgact atcacgtgtg aggatgatat ccggctgttg      12540
tggcgtatgt tgatgtggcc tgtgaattat cgtcctggta tggttggtat ggagtggcgt      12600
gccgacaggg attatgccca ctattcgggt gcggctgagt cggtggctaa gcaggtgttg      12660
ggggataatg cttggcgttt tccgcctggt ttgtttatga ccgatgatga gcgtcgtgga      12720
cgctatatta aggattttca ggtgcggttc cacttgtttg cagacaagtt gttgccggtg      12780
ttgtcgtggg ctcggatgac tgtcacggtg aaccagtttg agaatgcgca gtttgatcag      12840
cggggtttgc tgtttgattg tgtgcctgct gtgacccgga agcatgtgtt gactgccgag      12900
tctggttcga ttgtgtcgtg ggagtatgtg agggatgccc ctaaggctac ttcggtggtg      12960
gttggtggcc gcggcgaggg taaggatcgg ctgttttgtg aggatgttga ttcgatggcc      13020 gaggggatt ggtttgatcg tgtagaggtg tttaaggatg cccgtaacac ggattctgag       13080
catgtgcatc tcatcgatga ggctgagcag gtgctgtccg agttagggc cacgtcgggg       13140 tttaagatcg agttggctga gtcggatgtg ttgcggtttg gccaggcaa tctgatgccg       13200 ggtgatctta tctatgtgga tgtgggttct ggccctattg cggagattgt gcggcagatt      13260
gatgtggagt gtgattcgcc tggtgatggt tggacgaagg tgactcctgt tgcggggggat     13320 tatgaggata atccgtcggc gttgttggct cgccgtgtgg ctggtttggc tgcgggtgtg      13380
cgggatttgc aaaagttttg acaagtgatt ggggtttgtt gtgggtattg tgtgtaaagg      13440
gtttgatggt gtgttgaccg agtatgattg ggctcaaatg tctggtctga tgggtaatat      13500
gccgtccgtg aaagggccgg acgattttcg tgtcggcacg acaattcagg gtgccacagt      13560
gttgtgtagt gttttgccgg ggcaggcttg ggctcacgga gtgatgtgca cgtcgaatag      13620
tgttgagacg gtgacagggc agctgcctgg cccgggcgag acccgatacg actatgttgt      13680
tctgtctcgg gattgggagc agaacacagc caagttggag attgttcccg gtggccgtgc      13740
ggagcgtgcc agggatgtgt tgcgtgccga gcctggcgtg tttcatcagc aactgttggc      13800
gactttggtg gtgtcgtcta acgggttgca gcagcagctg gataggcgtg ctatagcggc      13860
ccgtgtggcg tttggcgagt ctgcggcttg tgatcctacc cctgtggagg gtgaccgggt      13920
gatggttcct tcgggggctg tgtgggctaa tcatgctaac gagtggatgt tgttgtctcc      13980
gaggattgag acgggttcta agtcgatcat gtttggcggg tctgctgtgt atgcttacac      14040
gatcccgttt gagcggccgt ttagtagtgc gcctgttgtg gtggcgtcta tggctacggc      14100
ggctgggggc acgcagcaga ttgatgtgaa agcctacaat gtgactgcca aggattttgg      14160
tttagcgttt atcacgaatg acgggtctaa accgaatggt gtgcctgcgg tagctaactg      14220
gattgctgtc ggcgtgtaat gcgctgcttg tgtgtgcggg atatgttgtg gtggttgtag      14280
```

```
tggtaggggg ctgtagtgtc atggcttaca cccacactcg tagcctctat ttgtaccgct   14340
atcgctactg tccttggttc gattcaggcg gttacttaca ggtcgaagaa gaggcttagg   14400
cagttgtctg cacaggttga tgcgatggaa gaatacacat ggaatattcg ccatattgtt   14460
catcgctata acgcgaattt gcctgagaat gttgagcctg taaaaatgcc tgatttgccc   14520 gagttttga aggatactgt tgatagtggt gggggtgaa ttgtgaggga gttggaggaa    14580
gagaaacggc agcgccgcaa ttttgagaag gtttcattgg tgttgctgtt tttgtcgctt   14640
gtgctactgg tggcgatggc tggggtgct ttgcggtatg gttctgtggc ttcgcaaagg    14700
gattcggagc aggcgagggc ccagtctaat ggtacagccg ctaaagggtt ggccagccgt   14760
gtgcggcagg tgtgtgcttc ggatgggcag gagtcggtgc ggcttcatca gtctggtttg   14820
tgtgtggatg ctgtgcgtgt tgagcgtagc gtgcagggtg tgccgggccc tgccggtgtg   14880
cgcggcccgc aaggaccggc tggtgttgca ggtgttgacg gccgtgacgg tgtgaatggt   14940
tcggcgggtg ttgtggggcc tgtgggtccg cagggttctc cgggtttgaa tggtgtggct   15000
ggcccggacg ggttgcctgg cgtgaatgga tcggatggcc atgatggtgt tccaggtcgt   15060
gcaggtgctg acggtgtgaa cggcgttgac ggtcggatg gttcggccgg tgagcgcggt    15120
gatgtgggcc cttcaggtcc tgccggcccg caaggtgcac agggtgaacg gggtcctatt   15180
gggcctcagg gtccgcaggg ttctgccggt gctgacggca cgaatggtaa agacggtaaa   15240
gatgggcgct cggttgtgtc tgtgtactgt tccgagggcc gcctggttgt gaaatatagt   15300
gacggtgtgg cttctacaat atcgagctcg gtggcctgcc agggtgtgaa accgtcgcct   15360
atagtgacta tatcatccca caagtaaaaa agaaaaggga agggtgttac tagtgttgat   15420
tgtggtgtta ggtggtgtgt ggtgagatac attcctgcgg cgcatcattc tgccggctcg   15480
aatagtccgg tgaataggggt tgtgattcat gcgacgtgcc cggatgtggg gtttccgtct   15540
gcctcgcgta aagggcgggc ggtgtctaca gcaaactatt tcgcgtcccc atcgtcgggt   15600
ggttcggcgc attatgtttg cgatattagt gagactgtgc agtgcttgtc ggagtctacg   15660
attgggtggc atgccccgcc gaatccgcat agtttgggta tcgagatttg cgcggatggg   15720
ggttcgcacg cctcgttccg ggtgccgggg catgcttaca ctcgggagca gtggcttgat   15780
cctagggtgt ggcctgcggt ggagaaggct gccatcctgt gtagacgttt gtgtgacaaa   15840
tataatgttc cgaagaggaa gcttagtgca gccgatttga aggctggtag gcggggtgtg   15900
tgcggccatg tggatgtgac ggatgcgtgg catcagtcgg atcatgacga tccggggccg   15960
tggtttccgt gggacaggtt tatggccgtt gtcaacggca agatgagag tggggagtta     16020 actgtggctg atgtgaaagc cttgcatgat cagattaaac aattgtctgc tcagcttact   16080
ggttcggtga ataagctgca ccatgatgtt ggtgtggttc aggttcagaa tggtgatttg   16140
ggtaagcgtg ttgacgcctt gtcgtgggtg aagaatccgg tgacggggaa gctgtggcgc   16200
acaaaggatg ctttgtggag tgtctggtat tacgtgctgg agtgtcgtag ccgtattgac   16260
aggcttgagt cgactgtcaa cggtttgaaa aagtgatggt ggtttgttgt gggtaaacag   16320
ttttggttgg gcttgtttga gcgtgccctg aaaacttta ttcaaacgtt tgttgctgtg    16380
cttggtgtga ctgcgggtgt cacgtatacg gcggagtcgt ttcgcggttt gccgtgggag   16440 tcggcccctga ttacgccgg ggttgctgca atactgtcgg ttgctacctc gtttggtagc    16500
ccgtcgtttg tggccggcaa acctaaaacc acggttgtgg atgctggtct tgttccaccg   16560
gatgatgggg gcatggttga gccgcactcg gtggatgtgt cggatcctgg catgattgag   16620
ccgacagatg atgtggatgg ttttgtcggc tatgtgccga ggcgtgcagc cgagtctgag   16680
```

```
gttggcacga tagagccgat cgaatgataa gtgaacatag atgtgtgccc cagcggtgct   16740
gccacgatcg tgtggtggtt gccgctgggg cactatttct gtttatgcgg tgtggctata   16800
attcgttgcg gtcgatggtg tcttcgagca tctgatacag gtggaggcag gtagagatcg   16860
tatcgctggc ctggtctaga acgttccggc cgataacgtt tttgtggttg tcgcggtggc   16920
ggatgatagc ccacatgatc tcgtcggctg ccgcctgcaa tagttttgcc tggtatgcga   16980
ttccggcgag ccagtctagt gcttcctggc ttgcataggg gctctggtcc tcgctgttgt   17040
cacgggtgtt gctgttgttt gtggggcgtc ctgcactgtc gcataaccac aggatttcgc   17100
tgcactcgtc tagcgtgtcc tggtcgatag cgagatcgtc gaggctgact tcgttgacgg   17160
taaggttcac gttgtcgagg gagatgggta caccgtactg gttttcgaca ctgtcaacaa   17220
tgttttccag ctgttgcatg ttggtgggct gttgttggac gatacggtgt atcgctgtgt   17280
tgagggtggt gtaggtgata ttgtgtgtgt tgttcatggt tttatccaat ccctgtgctt   17340
tcgtcgtttt cgtctggata gtatctactg tttgcgtagc ctgttagggt gatcagtgtt   17400
tggtctgccc actgtttcac ggtttgtctt gtcactccga gtcgttgggc ggctgtggcg   17460
taggtttggt catacccgta tacttccctg aaggctgcga gcctggctag ccgttttcgc   17520
tgtttggatg gctggcaggt gagggtgtag tcgtcgatgg ctagctgcaa atcgatcatg   17580
gagacgatgt tgttgccgtg gtgttgtggc gcggttggtg gtggtggcat gcctggttcg   17640
acactcggtt tccatgggcc tccgttccag atccattggg cggcttggat gatgtcggcg   17700
gtggtgtagg ttcggttcac tggtaatcct taaacaagtc gttcatgttg ctggtgttgg   17760
tggtgtcgaa tcgtccgacg cagtggcagt agtcgtacat gagtttaata atgtgttggt   17820
ggtcgccgag gtaggtgttg ccgctgatac tgtaggtggc tgtgccgtct ttgctgatgg   17880
tgtatttggc ggtgatggtt tcgggtgttt cggtgttggt gatgatggct gtggtggtgg   17940
cgcctacggt ttgtagtctg gtggtttggg tgccgtcgtc gaggatggtg gtgaccatta   18000
tgattctcct tagttgctgg tttggttgtc ggctatggct gtgatttctt gtaccggttt   18060
gggtagatct aaatgctgtg tggttttgtt tgctagtcgt tgggctacac ggtagcccat   18120
ttgggtccac tggttgcctt ccagctggtg gtattggttg cgtacggcta tgtagaggag   18180
tgcgtcttga tagaggtcgt cggggttgat ggccgggtag tggcgcgcaa tgttggtgca   18240
ggctttgtgt agctggtgtt ggtggtgtgg ggttgcccat tcccagttgg cggtggtggc   18300
ttgttctact ttggttggtc gtctgctcat ggcactatta cctggctatc tggtagttgt   18360
tgggtgtttt gttgttgata gtgtagcaca cgagtccggg gtggccggtg gtgcctgtgc   18420
ggtgccggta ccagacggat tctccttcca tggatgggca ttggatgaag gtgcgttgtc   18480
cttgctctga gatttcgagg tggtgccggt gccctgccat gagaatatta gatacggtgc   18540
cgttgtggaa ttcttggccg cgccaccatt cgtagtgttg gttgttgcgc cattggtgtc   18600
cgtgggcgtg caggatagta gccccggcta cgtttacggt ggtggtcatt tcgtccctgt   18660
cagggaagtg gaagtgtagg ttggggtagt ggttggtgag ttggtaggct tctgcgatgg   18720
cgcggcagca gtccacgtcg aaggagtcgt cgtaggtggt gacgcctttg ccgaagcgca   18780
cggcttcacc gtggttgccg gggatggatg tgatggtcac attttttgcag tggtcgaaca   18840 tgtggacgag ttgcatcatg gccatgcggg tgagcctgat ttgttccgtc aagggtgttt   18900
gtgtgcgcca ggcgttgttg ccgccttgtg acacgtatcc ttcgatcatg tcgccgagga   18960
atgcgatgtg gactcgttgc ggtttgcctg cttgctgcca gtagtgtttg gcggctgtga   19020
```

```
gggagcgtaa atagtcgtcg gcgaagtgtg atgtttcccc gccggggatg cctttgccga    19080
tttgaaagtc tcccgcccct accacgaacg caacattgct gtagtcggtg tgtgtgtctt    19140
ggttgggttt gggggggtgtc cattcggcta gtttatcgac gagttcgtcg accggatagg   19200
ggtcggttgc gggttggtgg tcgatgattt tttgtatgga tcggcctgtt tctccgttgg    19260
ggagtgtcca ttcggagatg cgtgtgcgcc gtacagtacc attggctaga ttgtcgtcga    19320
tggtgtcgat ggcgttgtcg tggttggcta gttgtgtgag gagccggtct atattgtcta    19380
tcatcggata tcctcttcct tttgcggggt ggtgttggct tgtttgcggc ggtagtcttt    19440
tataacggtg gcggagatgg ggtatcctgc ctgggtgagc tgttttgcta gccatgaggc    19500
ggggatggtt ttgtcggcga gcacgtctgc agccttgttg ccgtagcgtt gaataagggt    19560
ttcagttttg gttgccatga tgtcccatcg gttgtgtggt gggctgccat cctgtgcggc    19620
agtcgccgtc gtgtcctggt ttgcgggtgc accacgatac ggttccgtct gtgtggttga    19680
gtgttttgcc gcacatgacg tcacgtaggt gctcgggaaa ctcatcgttg ttgttgtccc    19740
cgtgcatgtc gatcaagtgt tgggttttag taaccatcat gcctcctatg tgtgaaagag    19800
tgtgcaaata ctatgcaggt gtcatggatg tttatgcggg tatggttttc atcaccttgc    19860
tgaacgttac ttggttactg tacatcatct gagtgatttc ctgatcagtc ttatcggggt    19920
gctgctttcg caggttcgcc cactggcagg cgttttcggt ctcctgctgt aaacgtgtca    19980
ggtgctgctc gttgatgatg tgtttccaca ttgtccatga cacgtcgagc ctgcggagca    20040
tgttcatggc tggcacgttg aaggaattga ggaagagtat ttcttcggtg tagtactgtt    20100
tttcgtattg gtcccatccg cttcggtgcc tgttgggctg gtttttgggg taggcttccc    20160
ggcagatttt tgtgtaaccgt ttggccatgt cgtcgggtag tttaatgtcg gggttggcgc   20220
ggatcatgga tcgcatcccg tcataggtgg tgccccaggt gtgcatgata tgcagtgggt    20280
cttcaccgtc tgcccatttt tctgcacaga tggcgaggcg gatacgcctc ctggctgttt    20340
ggctggtgtt gcgccggttg gggatggggc acgtgtcgag gggatccatg atgttttggt    20400
gtacctttct ggtttcgtgt tgttgacgtg ttttactgta gcacagtgtc tagtgcttgt    20460
gtcaaccctg tttttccggc ctgcaggtag gtgtctgtga catcccccag ggtgaggggc    20520
acatgggtgg cttgcggtaa tgcttgggtt agggtttggg ccatctggtc gcctgcgggg   20580
tctgggtctg accagatgta gatgtggtcg tagccttcga aaaatttggt ccaaaagttt    20640
tgccacgagg ttgcgccggg tatggctacg gctggccatc cgcattgttc gaggatcatg    20700
gagtcgaatt cgccttcgca aatgtgcatt tcggctgccg ggttggccat ggcggccatg    20760
ttgtagatgg agcctgtgtc tcctgccggg gttaagtatt tggggtggtt gtgggttttg    20820
cagtcgtgtg ggagtgagca gcggaaacgc attttttcgta tttcggctgg ccgcccccaa    20880
actgggtaca tgtatgggat ggtgatgcac tggttgtagt tttcgtggcc tggtatgggg    20940
tcattgttga tgtatccaag gtggtggtag cgggctgttt cttcgctgat gcctcttgcc    21000
gagaggaggt cgagtatgtt ttcgaggtgg gtttcgtagc gggctgaggc tttctggatt    21060
cggcggcgtt ccgcaatgtt gtatgggcgt atgctgtcgt acattcgggt tttctttctc    21120
taattgttgt tgtagcttgg cgagtccgcc tccgataccg catgtgtggc agtaccagac    21180
gcccttgtcg aggttgatgc tcatggaggg ctggtggtcg tcgtggaacg gacagaggat    21240
gtgttgctcg tttttggatg ggttgtagcg tatctggtgg gtgtcgagga ggcggcgggt    21300
gtcagaggtg tgggaggagc tcgttgaggg ttgataccac ataggcttcg ctccaggggtt   21360
tgttgcgttg tttcatgatg acgagtccga tggtggaatt gttttgtttg tttcggtgtg   21420
```

```
tttcgtagtt gcgtgcctcc cggctggctt gtttcacgaa ttcggcgagg tgtggctggc    21480
cggctttggc ttcgatcaca taggttttgt tgccggttgt gaggataagg tcgccttcgt    21540
cttcacggcc gttgaggtgg aggcgttcta tatcatggcc ggtgtcgcgt agttggtgga    21600
ggagtcgtgt ttcccattct gcgccggccc tgcggtttct tgattgttgt gtcgacatga    21660
tagtcctttg tgtgttgtgg tcatattcca gggctgtttt tcggcgaggg gcccgaagaa    21720
ggtgtattcg ggataggctc gtagccgctc gtatcgggtg ccgtcggggc tggatttgcc    21780
tgtgcgctgt ttgaggacgg cgatgcgtgc ctctgccggg atcgatagcc cgttgccgtt    21840
atcctcgcca ccatacaacg agactccgag gatgagttgt ggttttttcgg agaggccgtt    21900 tttgattttct cgccgggcgg gcgggtgttc gatgtcggag ccggttttgt cggttgcgtg    21960
gtgtgtgaca ataatggtgg agccagtatc gcggccgagg gctgtgatcc attgcatggc    22020
ttcttgctgg gcctgatagt cactctcgca gtcttggatg tccatcaggt tgtcgataac    22080
gatgatgggt gggaaggtgt tccacatttc catgtaggct tgcagttcca tggtgatgtc    22140
tgtccatgtg atgggtgact ggaatgagaa tgtgatgtgt tggccgtggt ggatgctgtc    22200
tcgatagtat tctggcccgt agtcgtcgat gttttgttgt atctgggcgg tggtgtgttg    22260
ggtgttgagt gagatgattc gtgtggaggc ctcccagggt gtcatgtccc ctgatatgta    22320
gagggctggc tggttgagca tcgctgtgat gaacatggct agccctgatt tttggctgcc    22380
ggaccgcccc gcgatcatga cgagatcccc tttgtggatg tgcatatcct ggttgcggta    22440
gaggggttct agttgtggta tgcggggcag ctcggctgcg gtttgggagg ccctctcgaa    22500
ggatcgttgg agagagagca tcgggacctt atctatctat cggttacgat ttgtatgaat    22560
attggcggtt agatggagtc gatgtctaca tcatcactac cagtggtgtt gggctgactg    22620
tctcgctggt caacgtaggc tgctacaagg tcgtagatgg cgtcgtccaa tggtttgagc    22680
acgaccgcgt tgaagccgtt tttggtgcgc acgtggcga gtttgaaggc ttgctcttcg    22740
ccaaggtagg tttcgaggtc gcggatcatg gagtgtgggc ggtcgttgct gccgcgtact    22800
ttttcgatga tggcgttggg gatggtttct ggggtgctgt tgttgaggtc gtctagggtg    22860
tggaagatgg tgacatcagc gtagatgcga tcggcggtct gtccaccgta gccttcagtg    22920
ttgtgctcga cgtcgtggac tttgaaggcg atggcgtgg cgtcctggtt tcgggagggg    22980
ttgaagaagg tgctgttgct gttgtttcgg tagtttgcga gtcccattgt tgtttccttt    23040
actgttttgt tgatttgtgt cggtttttat cgggtgaggc tgtttcgttt gctgcggaac    23100
gcctcggata cgtcagtgtt gctggtgatg atcttcttgt actgtttcag aaggtcggct    23160
agctgtgctt tgcttgttgc attgttgatt ttgtcaatga tggtgttgtt tccttcactg    23220
gcaatgttgt ctacgtagtc tttggcggcc tggttgtatc ggtcttggag gatgatggat    23280
gcggaggcga tcagtgttgc caggtcccag ttccttgccg ccgagctgtt tttgagtccg    23340
cctagcaggt cgatgatagt cttctttact tcgtcggcgg tgtctccacg gatgactgtc    23400 catgggcgg cgtagtctcc gccgtatttg agtgtgatgg tgatgcgatc atcagtgctg    23460
ttggtgttat cgttcactgg tgctccttgc tttcttctgt tggggctgtg atggtggttt    23520
ctgtagggta cctgtaggcg tctttcccgt tgacggccca gcaggcgtcc ttgacggggc    23580
atcctttgca gagtgctgtg acgtggggta cgaagatgcc ttgactgatt cctttcattg    23640
cttgactgta catggatgat acatgctggt aggtgttgtt gtcaaggtcg tacagttcgg    23700
tggatgtgcc ttgtgtcggg gacttgtcgt cgttgcggct ggtggctggc gtccaaaaca    23760
```

```
tgccttttgt cacatcgttg ccgtgttggg cgagcatgta ccggtatgtg tgcagctgca   23820
tgctgtctgc tggtaggcgt ccggttttga ggtcgaggat gaaggtttcg ccggtgtcgg   23880
tgtcggtgaa aacgcggtcg atgtagccga cgatttgggt gccgtcgggg agggtggttt   23940
cgactgggta ttcgatgccg ggctggccgt ctaggactgc tgtgtggtat tgtggattgt   24000
ttgtgcgcca gttttccac cggttgacga aggtttggcc gtagagcatc caccagtcgt   24060 agtcttttt gtgtggcccg cccgactcgc acatgttttt gcatattctg ccggagggtt   24120
tgatttctgt gccttcggat tcggcgaggg ctacttgggt gtcgaaaatg tttttgaagg   24180
atgagagttt gtctggcagt gcagggtatt cggcggggtt gtacaggtgt aggtcgtatt   24240
gttcggtgat gtggtgtatg gcgcttccgg cgatggtggc gtaccaggtg tgatatgtgg   24300 cttttgtatcc gtgttggagg cgccattttt cgccgcattc ggcccactgt gacagtgatg   24360
agtaggagat gtggcctgga tggttgatgg ttttcgggta ttgtgctaga ggcattactt   24420
gtcgcttttg ttccatgggt tgcgggtgtc ctggccggcg tggtgttgct gataggcgag   24480
gagtgcgagg cagtgccagg cggcgtgtgc caggtggggt agccctgatt catcgtcgag   24540
gttgtgtcct tgctgccagg ctagcaggtg cctatagagg gcgtcgacac tgtggctcca   24600
cgggtatcct ccggtccagt tgttgtcgcc gtatttggtg gcaccgtagc ctgcaacctc   24660
gccgagagcg tgcaaggctg cggggtcgat gaggagagc ctgcagagtt tcaattcttt   24720
tttggcaccg ctgttggggt cggtgtacat gcgggttggc ttatccatgg ggtgtgtgct   24780
ccttgggggt gggttactgg ttgttgttgt gggctagggc gacggcgaga ataatgatgg   24840
cgagggtttc agcgatgagg attggtgttg tgatcatttg ttgttttttgg gctggtaggt   24900 gagtgtggag gcacccagga gggtggtgag ggcgcatgcg gcgatgatgg cgagggctgc   24960
cttgtgtggg gtgccggttg cgtacatcca tgtgatgatg gcgccttgga tccatgccag   25020
tgtggtgaag aacgtttcgt agctgtgtag ctcaatgttg ttgggtgtgt tcatgcttgc   25080
tcctggatga tggtgttgat ggttttgtag atgttgtaca ggtcggtttc gatggtttgt   25140
agctgtttga tttggtggtc gagatcaatg tttgggttga gggtgttgat gcggatgcg   25200 atgtcggtgg ctgtgcggag tgtgccgccg gtgtggtgaa tgatgtgtgc cgtgtcggcg   25260
agtccggtgg tgacagcgta gtgggagagg agaggcatag cggtccttgg cgggttagtg   25320
ttgcgggttg atgttgaggt cggtgacgtg gggtgtgttt tctgttccgg tgacgaggca   25380
gtggacggtg acgggtagtt tggatgctcc gggctggcgg acggtggcgc cgtagacgat   25440
agtaaaggtg tctttgtggg cgcctatgac tttgtggagt tggaggtcga tgtcgggtt    25500 gccgttccag ttgacaccgt gtgcggcggc ttgttgttcg gctttgcggt tgcaggtgtg   25560
tgcggcggtg atcatggtga gaccttgtga ggtttcttca ccgcgtgttt gggcttgccg   25620
gtgggctttc tgctgttcgg ctcgcagtga ctgttctgcg gcggcttgcc gggctttctt   25680
ttcggctttg cgctgttgga cggttttggg tgtccattcg gtgttggctg tggtggcctg   25740
tggggctggc tgtgaggcga gtggcggatt gtcgccgggg gctggcatga atgaggcggc   25800
ggcaatgatg gcggctgtga tgccggcgat ggtgtagcct gttttcttgt tcatgttttg   25860
tgtccccttt ccggggtgtt gttcgttgct gacatggtta atactttcag cgactgggcc   25920
cactgtcaag gctacgctca acgattgtga gcgattcgtg tgtggctagg ggttttatcg   25980
gctgtacagg gtgagtagat ggccaacgtt gatgcgggtc acatgccagt agagttgtgt   26040
ggcttcctca ctggtgagtg gcttccactc gttgtggctg aatacggtgc catcagtggc   26100
gataaacgtg ttggggcgta gcttgtggag ttcggcttcc acactctgtc ggtaggcttc   26160
```

```
ggcgaggccc tcaaaatcca tgtggtcgca ggagaggttt tcgaggcgtg tcaggtcgaa   26220
gggtgtgggg cagtcgtagc tggcgggggt gtagagctgg gtgaagtggt tggcgatctt   26280
ctgcatcatg attccttttc tggtgatggt gtgttgatgg tttttatcggg tggatgcgac   26340 caggatggcg tctacatcga tcatgtcgat catgtcgtgg agttcctcgg cctcattctc   26400
ggataggtgg cgccagtcac agtctccgta tacggcgccg tcgagggtga cagtccacaa   26460
tggccggatg agccgtatgg cttcttgtac tttagcgtgg tacatgcgac gcaccatatc   26520
gagatcgatg tcgtctgaat ggtttccggt gaggctgtgg aggctgaggg gtcgatttc    26580 tgtctgcctg tagagggatg tgaaggatgg tgtgacgagc gtgccatcca tagggtgtgt   26640
gctcctttcg gtggtgtagg ggttgttgtg gtttctagag tgtgcgggct gttaccccac   26700
tgtcaaggct acgctcattt ggattgagcg tttcatgggg gtgtgtcggg tgtgacagat   26760
gtcacttaag cctttattga ctctcccagc gtctcaaatc ttctgggggt aggattatgc   26820
agggttggcc ctggtagtcg attctaggga ccttctaggg cgtctcaggg gtatgtctga   26880
gtgatagcag gtctggtaga tgacccggca gatctacctt gattttcatg gcaggagtcg   26940
aggtgccata tatgggcata gaatctaaac cctcatactg tgtgagatgt atcacactcg   27000
cctagtatgg tgtgcactct cgggatcact ctgccgatct ggcgtggagg gtgtagccaa   27060
gaaatgccgt ttaaagcctt cgcatggcgc ctaggagcgc cttgcggggt ggggctagg    27120 tatttatacc cccagcatat tctgatcgat tctagacgta cccaaaagcc tgatatacga   27180
tcaaccatct cagcatagac catcagcccc tatcctggtt agctaagcct acactatgtg   27240
gacagtgtgg gataccgtgg gggaagaagg acacggtaaa agaaagaggg gggagcatca   27300
gccttcccac ctgaggtact tcagttcacc ttaaggtctt agcacttagc accgagcccc   27360
tcaaaggctc ggcatcagcc cgaacaggct cagccctgaa aggggtacac gtcatcagag   27420
aaggcttgag agtacgagga gccctagcga cgagtactcg aaagcctgag gaacaccct    27480 cagcactgat gggcctagcg tgttcggaaa ggacacaaga gtacagtgtg acagctatcc   27540
gggagtgaaa cccgttctga ctaggggttt cagccttaac caccctcaaa ggttacaaga   27600
ctttaagaaa atttaaggaa aagtttaggt ttaattttg gacctttacc accaaaaaca    27660
cccgtttaca cccctcaaac ccgcctatag agccaaatcc accagtttga ctcatcccag   27720
gtggggtatg ataggctgga caggtagcca gctggacgca aggccgaaat ccgctgacgc   27780
ggctttcacc cttacatcca tcagtctacc aaagacttaa agacctaagg gcttagcgct   27840
aaggtgctga tagcttagca ccgagcccct caagggctcg gcatcagtct taaagcctta   27900
aacacttcaa gtacatataa aactttaaga gcttaacact taaggttatc aataaacatt   27960
aaagctttaa agtcttaaag tacatataaa accttaacag ttaaacgtta aaagctttaa   28020
accttaacac ctaagttaag tataaaacct taaggatta gcacttaagg atataaactt    28080
aacatcagtg tttaagactt taaacttaa aataactatt aagacttaaa gacctataag    28140
ctttaaacac ttaaagtaac tataagactt taaaaaccctt aagtacttaa agttaaccat  28200
cagtcttaaa ctttactatt atacctataa gtcttaaagc ttataggtat aataatataa   28260
tataagtatt aaagcttata agttataaaa gttttagaag agctaagggg ttaacttctt   28320
tacttctctt ctctctttgg ttctttctct cttctcttct tttcttcatc aggggagaag   28380 aggaacccttt taccgtcaac gctgatgggc ttttcgccgt gtgtctcgtg taccaccggt   28440
cgcacgctcc cggtttgtac actccccaca ctctgacacc cgtgtccctt tcaggtttgg   28500
```

| | |
|---|---:|
| cgtgttcggc tgaaggcgta cggcgtgtca cgccaacacc cttaacacca ggtaagactt | 28560 |
| aaagtgcata ttatatgtag aagactttaa aaacctgtca ggtgttcctg ctgagcctgt | 28620 |
| gtcctacacc gctaggcgcc aagcgctaag ctgtgaaacg cgaacacaca ctcaccccct | 28680 |
| ttttctttcg tgtccttctc ttttgacaca gctgggggc gatgtgatct ttttcacacc | 28740 |
| cgttgggggt agtggagaaa acaaccaccc cggcacaaac agaacacccc ctcaaacgaa | 28800 |
| caaaacaggg cctagaatcg atcggcaggg caccggtaga gtattcatac ccccaacggt | 28860 |
| tcccaagccg ttacaggagc aatgagaggc tcacaggggc cataggagat caggggacgc | 28920 |
| gatggcacac accaaccgca cagccagcca agcccaccgg cgctggcggg caagactcat | 28980 |
| cacccaagcc cgacagcaag gccaaaccga atgcccactc tgcggagcca ccatcgcctg | 29040 |
| ggacacacac gacctgccaa ccagcccga agccgaccac atcacgcccg tcagcagggg | 29100 |
| aggactcaac accctcgaca acgggcaaat catctgcaga acatgcaaca gaagcaaagg | 29160 |
| caatcgcagc gaaccaaaca tcaaactcca acaacaaacc acaaaaacat tgattccatg | 29220 |
| gtgaaaaacc cgccaacccc caccggggac acccctgca caggcggcaa gacct | 29275 |

<210> SEQ ID NO 4
<211> LENGTH: 29153
<212> TYPE: DNA
<213> ORGANISM: Bacteriophage 103672

<400> SEQUENCE: 4

| | |
|---|---:|
| tcccttttgt ggattgtctg tttgtcgact ttttgtgttg gtggtgagtg ttgtgcagcc | 60 |
| tgagcttcct gatagtcgtg gatggtgtgg ggagacgcgt cgttggtggc gtgtgtgggg | 120 |
| tgaggatccg cgtgccgggt ttgtgtctga tgaggagtgg ctgtttctca tggatgctgc | 180 |
| ggtgattcat gattgtgtgt ggcgtgaggg tcgcgcggat ttggtggctt cgcttcgtgc | 240 |
| tcatgtgaag gcttttatgg gtatgttgga tcggtattcg gttgatgtgg cgtctggtgg | 300 |
| ccgtggtggg ggttctgcgg tggcgatgat tgatcggtat aggaagcgta ggggtgcttg | 360 |
| atgtctcggg tggtgggttc tcaggttcct cgtcaccgtg tggctgcggc gtattcggtg | 420 |
| tctgctggcg gtgatgctgg ggagttgggt cgtgcgtatg ggttgacgcc tgatccgtgg | 480 |
| cagcagcagg tgttggatga ttggctggct gtcggtggta atggcaggct tgcttcgggt | 540 |
| gtgtgtgggg tgtttgtgcc tcgccagaat ggcaagaatg ctatttggga gattgtggag | 600 |
| ttgtttaagg cgactattca gggtcgccgt attttgcata cggctcacga gttgaagtcg | 660 |
| gctcgtaagg cgtttatgcg gttgaggtcg ttttttgaga atgagcggca gtttcctgac | 720 |
| ttgtatcgta tggtgaagtc gattcgggcg acgaatggtc aggaggctat tgtgttgcat | 780 |
| catccggatt gtgccacgtt tgagaagaag tgtggctgca gcggttgggg ttcggtggag | 840 |
| tttgtggccc gttctcgggg ttctgctcgc gggtttacgg ttgatgattt ggtgtgtgat | 900 |
| gaggctcagg agttgtcgga tgagcagttg gaggctttgc ttcctacggt gagtgctgcc | 960 |
| ccgtctggtg atcctcagca gatttttctt ggcacgccgc ctggtccgtt ggctgatggt | 1020 |
| tctgtggtgt tgcgtttgcg tgggcaggct tgtcgggtg gtaaaaggtt tgcgtggacg | 1080 |
| gagttttcga ttcctgacga gtctgatccg gatgatgtgt cgcggcagtg gcggaagttg | 1140 |
| gctggggaga cgaatccggc gttggggcgg cgtttgaatt ttgggactgt gtcggatgag | 1200 |
| catgagtcga tgtctgctgc cgggtttgct cgggagcggc ttggctggtg ggatcgtggc | 1260 |
| cagtctgctt cgtctgtgat tcctgcggat aagtgggctc agtctgcggt ggatgaggcg | 1320 |
| gctctggttg gcgggaaagt gtttggtgtc tcgtttctc gttctgggga tcgggttgct | 1380 |

```
ttggcgggtg ccggtaaaac tgatgctggg gttcatgttg aggttattga tgggctgtcg    1440
ggaacgattg ttgatggtgt gggccggttg gctgactggt tggcggttcg ttggggtgat    1500
actgaccgga ttatggttgc cgggtctggt gcggtgttgt tgcagaaggc gttgacggat    1560
cgtggtgttc cgggccgtgg cgtggtggtt gccgatactg gggtgtatgt ggaggcttgt    1620
caggcgtttt tggagggtgt caggtcgggt gtgatcagtc atcctcgtgt tgattctcgc    1680
cgtgacatgt tggagattgc tgtgaggtcg gctgttcaga agcgtaaggg gtctgcgtgg    1740 ggttgggggtt cctcgtttaa ggatggttct gaggttcctt tggaggctgt atcgttggcg    1800
tttttggggg ctaaacgtgt tcgtcgtggc cgtcgggagc gtagtggtag aagcgggtg    1860 tctgtggtat gaactcggat gagttggctt tgattgaggg tatgtacgat cgtatccaaa    1920
ggttgtcttc gtggcattgt tgcattgagg gctactatga gggctctaat cgggtgcgtg    1980
atttgggggg ggctattcct ccggagttgc agcgtgtgca gactgtggtg tcgtggcctg    2040
ggattgcggt ggatgctttg gaggagcgtc tggattggct tggctggact aatggtgacg    2100
gctacgtttt ggatggtgtg tatgctgcga atcggcttgc tacggcgtcg tgtgatgtgc    2160
atttggatgc gctgatttt gggttgtcgt ttgtggctgt tatcccccag ggggatgggt    2220
cggtgttggt tcgtccgcag tcgccgaaga attgtactgg ccggttttcg gctgacgggt    2280
ctcgtttgga tgctggtctt gtggtgcagc agacgtgtga tcctgaggtt gttgaggcgg    2340
agttgttgct gcctgatgtg attgttcagg tggagcggcg tgggtctcgt gagtgggttg    2400
agacgggccg tatcgtgaat agtcttggtg cggttccgtt ggtgccgatt gtgaatcggc    2460
gtaggacgtc gcgtattgat ggccgttcgg agatcactcg gtctattagg gcttacacgg    2520
atgaggctgt gcgcacactg ttgggggcagt ctgtgaatcg tgacttctac gcttatcctc    2580
agcgttgggt gactggtgtg agcgcggatg agttttcgca gcctggctgg gtcttgtcga    2640
tggcttctgt gtgggctgtg gataaggatg atgatggtga tacccccgaat gtggggtcgt    2700 ttcctgtcaa ttcgcctaca ccgtattcgg atcagatgag actgttggcg cagttgacgg    2760
cgggtgaggc tgcggttccg gaacgctatt tcgggtttat cacgtctaac ccgcctagtg    2820
gggaggcttt ggctgccgag gagtctcggc ttgtgaagcg tgctgaacgc aggcagacgt    2880
cgtttggtca gggctggctg tcggttggtt tcctggctgc taaggcgttg gattctcgtg    2940
ttgatgaggc cgatttttt ggtgatgtgg gtttgcgttg gcgtgacgct tcaacgccga    3000
ctcgggcgga tacggctgat gctgtgacga agcttgttgg tgccggtatt ttgcctgctg    3060
attctcgtac ggtgttggag atgttggggc ttgatgatgt gcaggttgag gctgtgatgc    3120
gtcatcgtgc cgaatcttcg gatccgttgg cggcgctggc tggggctatt tctcgtcaaa    3180
ctaacgaggt ttgatgaatg gcttcgggtg ctatgtcgag gcttgctgcg actgagtatc    3240
agcgtgaggc ggtcaggttt gctgggaagt atgcgggcta ttattctgag cttggtcgtt    3300
tgtggcattc cgggaagatg acagatgcgc agtatgtgcg tttgtgtgtg gagttggagc    3360
gtgccggcca tgatggttcg gcatcgttgg ctgccaggtt tgtgcaagat tttcgccggt    3420
tgaacggtgt cgatcctggt ttgattgtgt atgacgagtt tgatgctgcg gcggcgttag    3480
ctcggtcgtt ttcgactatg aagattcttg agagtgaccc ggataggtgg aatgacacga    3540
ttggtgcgat ggctgcgggt gttaatcggg ctgtcatgaa tgctggccgt gacacggttg    3600
agtggtcggc gggtgcgcag ggtaggtcgt ggcgtcgggt tactgatggt gatccgtgcg    3660
cgttttgtgc catgttggct acgaggtcgg attatacgac tcgggagcgg gcgcttacta    3720
```

-continued

```
cgggtcatac tcggcgtcat aagcgtgccg gtaagcgtcc gcttggttcg aagtatcatg      3780
atcattgtgg gtgtacggtg gttgaggttg ttggtccttg ggaaccgaat agggctgatg      3840
ccgcatatca gaggacgtat gagaaggctc gtgagtgggt tgatgatcat ggggttgcagc     3900 agtcgcctgg caatattttg aaggctatgc gtactgttgg cgacatgaga tgatggtttc      3960
cggttgtgtg ccgccggtta tcggtgcaca gggttgtctc ccgcacgggg gtcaacaatg      4020
ttgtgttgtt ttccgcaagg agtatagggt taggctatgg ccgatcaaaa agttgaagaa      4080
cagaatgttg acaatgatgc tgttgagccc ggaaagggtg gagatgttgt tgatgttgtg      4140
aaggatgggc aggctgccgg cgatgatcat gccggtgatg tttccgtgaa ggaggagtct      4200
tcttctggca cggattggaa ggctgaggcc cgtaagtggg agtctcgtgc taaaagtaat      4260
ttcgccgagt tggagaagct tcgcgcctcg gatggtgatg cggggtctgt gattgatgag      4320
cttcgccgca agaatgagga actcgaagac cggatcaacg ggtttgttct tgagggtgtg      4380
aagcgcgagg tggcttcagg gtatggtttg tccagtgatg cgatcgcttt cttgtcgggt      4440
ggcgataagg agtcgcttgc cgagtctgcg aaagctttga agggtttgat cgaccatagt      4500
agtggtggcg tgggtgtgcg ccgtcttgcg gggagtgccc ccgttgatga tgttaaacga      4560
cgtgagggtg tcgcgtttgt ggatgctctt gtcaataatt ctaggagatg atttgtgatg      4620
gctgacgatt ttcttcctgc agggaagctt gagcttcctg gttctatgat tggtgcggtt      4680
cgtgaccgtg ctatcgattc tggtgttttg gcgaagcttt cgccggagca gccgactatt      4740
ttcggtcctg ttaagggtgc cgtgtttagc ggtgttcctc gcgctaagat tgttggtgag      4800
ggcgaggtta agccttccgc gtctgttgat gtttcggcgt ttactgcgca gcctatcaag      4860
gttgtgactc agcagcgtgt ctcggacgag tttatgtggg ctgacgccga ttaccgcctg      4920
ggtgttttgc aggatctgat ttccccggct cttggtgctt cgattggtcg cgccgtggat      4980
ctgattgctt tccacggtat tgatccggct acgggtaagc tgctgcggc tgtcaagtct      5040 tcgctggata agacgaagca tattgttgat gcaaccgata gcgctacggc tgatctgatt      5100
aaggctgttg ggctgattgc tggtgccggt ttgcaggttc ctaacggggt tgctttggat      5160
ccggcgttct cgtttgccct gtctactgag gtgtatccga aggggtctcc gcttgccggc      5220
cagcctatgt atcctgccgc cgggttcgcc ggtttggata attggcgtgg cttgaatgtt      5280
ggtgcttctt cgactgtttc gggtgtcccg gagatgtcgc ctgcctctgg tgttaaggct      5340
attgttggtg atttctcgcg tgttcattgg ggtttccagc gtaacttccc gatcgaactg      5400
atcgagtatg gtgacccgga tcagacgggg cgtgaccta agggccataa tgaggttatg      5460
gttcgcgccg aggctgtcct gtatgtggct atcgagtcgc ttgactcgtt tgctattgtg      5520
aaggagaagg ctgccccgaa gcctaatccg ccggccgaga actgatctat ttgttgctat      5580
aatgttcatg ctgtgtgcag ggggtggtat tgatgggtat cattttgaag cctgaggata      5640
ttgagccttt cgccgatatt cctagagaga agcttgaggc gatgattgcc gatgtggagg      5700
ctgtggctgt cagtgtcgcc ccctgtatcg ctaaaccgga tttcaaatac aaggatgccg      5760
ctaaggcgat ccttcgtcgg gctttgttgc gctggaatga taccgggggtt tctggccagg      5820 tgcagtatga gtctgcgggt cctttcgctc agactacacg gtctaatact cccacgaatt      5880
tgttgtggcc ttctgagatt gccgcgttga agaagttgtg tgagggtgat ggtgggcctg      5940
gtaaggcgtt cactattaca ccgaccatga ggagtagtgt gaatcattct gaggtgtgtt      6000
ccacggtgtg gggtgagggt tgctcgtgcg ggtcgaatat taacggctac gctgcccttt      6060
tgtgggagat atgatatgac cagttttcct tatggtgaaa cggttgtgat gcttcagccg      6120
```

```
actgttcgtg tcgatgatct tggtgacaag gtggaagact ggtctaagcc tgtcgagact   6180
gtgttccata acgtggccat ctatgcttcg ttgtcgcagg aggatgaggc cgcggggcgt   6240
gactcggatt atgagcattg gtcgatgctt ttcaagcagt ctgttgtggg tgccggttat   6300
cgttgtaggt ggcgtattcg gggtgttgtg tgggaggctg acgggtctcc tatcgtgtgg   6360
catcacccca tgtctggctg ggatgcgggc acgcagatca atgtgaagcg taagaagggc   6420
tgatgggtag tggctcagga tgtgaatgtg aagctgaact tgccgggtat tcgtgaggtg   6480
ttgaagtctt ctggggtgca ggctatgttg gctgagcgtg gcgagcgtgt caagcgtgcg   6540
gcctcggcga atgtgggcgg taacgctttc gatagggccc aataccgtaa tggtttgtcg   6600
tcggaggtgc aggttcaccg tgttgaggct gtggcgagga ttggcactac ctataagggt   6660
gggaagcgta ttgaggcgaa gcatggcacg ttggcgaggt cgattggggc tgcgtcgtga   6720
tcgtttacgg tgatccgcgt gtgtgggcta acgcgtgct caaggatgat ggctggctgt   6780
caggtgtgcc ttgtgtgggg acggtgcccg atgattttac gggtgacctg atttggttgg   6840
cgttggatgg tggcccgcag ttgcatgtgc gtgagcgtgt ttttttgcgc gtgaatgtgt   6900
tttcggatac gccggatcgt gctatgtcgt tggcgcgtcg tgttgaggct gtgctggctg   6960
atggtgtgga tggtgaccct gtggtgtatt gtaaacggtc tactggccct gatttgctgg   7020
ttgatggtgc acgttttgat gtgtattcgc tgttcgagct gatatgtagg cctgtcgaat   7080
ctgaataagc ttattgtttt tgttttaatg taattgtttg atatttaatg ggggttgtga   7140
tggctgcaac acgtaaagcg tctaatgttc gctctgctgt tacgggtgac gtttatattg   7200
gtgccgcgca cgcgggtgac actattgatg gtgtgaagac ggttcctgac ggtcttaccg   7260
ctttaggta cctgtctgat gacgggttta agattaagcc tgagcgtaaa acggatgatt   7320
tgaaggcttg gcagaatgcg gatgttgttc gcactgtggc tactgagtcg tctatagaga   7380
tttctttcca gctgatcgag tctaagaagg aggttatcga gctgttttgg cagtcgaagg   7440
ttactgccgg atccgattcg ggttcgttcg atatttctcc gggtgccacg acgggcgtgc   7500
acgctttact gatggatatt gttgatggtg atcaggttat tcgctactat ttccctgagg   7560
ttgagttgat cgatcgtgac gagattaagg gtaagaatgg cgaggtttac gggtatggtg   7620
tgacgttgaa ggcgtatcct gcccagatta ataagaaggg tgatgcggtg tctggtcggg   7680
ggtggatgac ggctttaaaa gctgatactc ctccggttcc gccttctccg aagcctcagc   7740
cggatccgaa tccgccgtct aataactgat acacagtttt aagggattgt tgatagatga   7800
gtgacactgg tttcacgttg aagattggtg accgtagctg ggtgttggcg gatgcggagg   7860
agacggctca ggctgttcct gcccgcgtgt ttcgccgtgc cgccaggatt gcccagtcgg   7920
gggagtctgc ggatttcgcc caggttgagg tgatgttttc tatgctagaa gcggccgcct   7980
cggctgacgc ggtggaggct ttggaggggc ttcctatggt tcgtgttgcc gagattttcc   8040
gtcagtggat ggaatacaag cccgaccaga aagcagcctc cctgggggaa tagtttggct   8100
ccacggcctg attgatgatt atcgtggggc catcgaatac gatttccgca ctaaatttgg   8160
tgtttctgtt tatagtgttg gtggcccgca gatgtgttgg ggtgaggctg tccggctggc   8220
tggcgtgttg tgtaccgata cgtctagcca gttggcggcc cacctgaatg gttggcagcg   8280
cccgtttgag tggtgcgagt gggctgtgtt ggacatgctg gatcattaca ggtctgctaa   8340
tagtgagggg cagccggagc ctgtggcgag gcctacggat gagcgtaggg cccggtttac   8400
gtcggggcag gtggacgata ttttggcgcg tgttcgtgcc ggtggcgggg tgtctcgcga   8460
```

```
gattaatatt atgggg tgaa tagtgtatgt ctggtgagat tgcttccgca tatgtgtctt   8520
tgtatacgaa gatgccgggt ttgaaagcgg atgttggtaa acagctttcc ggggtgatgc   8580
ctgcggaggg tcagcgttcg ggtagcttgt ttgctaaggg catgaagttg gcgcttggtg   8640
gtgccgcaat ggtgggtgct atcaatgttg ctaagaaggg cctcaagtct atctatgatg   8700
tgactattgg tggcggtata gcgagggcta tggctattga tgaggctcag gctaaactta   8760
ctggttttggg tcacacgtct tctgacacgt cttcgattat gaattcggct attgaggctg   8820
tgactggtac gtcgtatgcg ttgggtgatg cggcttctac tgcggcggcg ttgtctgctt   8880
cgggtgtgaa gtctggcggg cagatgacgg atgtgttgaa gactgtcgcc gatgtgtctt   8940
atatttcggg taagtcgttt caggatacgg gcgctatttt tacgtcggtt atggcgcgcg   9000
gtaagttgca gggcgatgac atgttgcagc ttacgatggc gggtgttcct gtactgtctt   9060
tgcttgccag gcagacgggt aaaacgtcgg ctgaggtgtc gcagatggtg tcgaaggggc   9120
agattgattt tgccacgttt gcggctgcga tgaagcttgg catgggtggt gctgcgcagg   9180
cgtctggtaa gacgtttgag ggtgctatga agaatgttaa gggcgccctg ggttatcttg   9240
gtgctacggc tatggcgccg tttcttaacg gcctgcggca gatttttgtt gcgttgaatc   9300
cggttatcaa gtctatcacg gattctgtga agccgatgtt tgctgccgtc gatgctggta   9360
ttcagcgtat gatgccgtct atttttggcgt ggattaatcg tatgccgggc atgatcactc   9420
gaatgaatgc acagatgcgc gccaaggtgg agcagttgaa gggcatttttt gcgagaatgc   9480
atttgcctgt tccgaaagtg aatttgggtg ccatgtttgc gggtggcacc gcagtgttcg   9540
gtattgttgc tgccggtgtg gggaagcttg tcgtagggtt tgccccgttg gcggtgtcgt   9600
tgaagaatct gttgccgtcg tttggtgctt tgaagggtgc cgccgggggg cttggcggcg   9660
tgtttcgcgc cttgggtggc cctgtcggta ttgtgatcgg cttgtttgct gccatgtttg   9720
ctacgaacgc ccagttccgt gccgctgtta tgcagcttgt ggctgtggtt ggccaggcgt   9780
tggggcagat tatggccgct attcagccac tgttcgggat tattgctggc gtggttgcca   9840
ggttggcgcc agtgttcggc cagattatcg gtatggttgc tggtttggct gcccaactgg   9900
tgcctgttat tggtatgctt attgcccggc tggttcctgt tattacccag attattggta   9960
tggtaaccca ggttgctgcg atgattttgc ctatgctgat gccggttatt caggctgttg  10020
ttgctgtgat acggcaggtt gttggcgtga tcatgcagtt ggtgcctgtt ttgatgcctg  10080
tgattcagca gattttgggt gctgtcatgt ctgttttgcc gccgattgtt ggtttgatac  10140
ggtcgctgat accagtcatc atgtcgatta tgcgtgtggt ggtgcaggtt gtttcggttg  10200
tgttgcaggt ggtggcccgt attattccgg ttgttatgcc gatttatgtt gcggtgattg  10260
gattcattgg caagatttat gctgcggtta tcggttttga ggctaaggtt attggcgcta  10320
ttcttcgtac tattacgtgg attgtgaatc atttagtgtc tggcgtcagg tctatgggca  10380
cggccatcca gaatggctgg aatcatatca aatcgtttac gtcagcgttt attaacggtt  10440
tcaaatctgt tatttctggc ggcgtgaacg ctgttgtggg gtcttttgcc cggcttggtt  10500
cttcggttgc ctcccatgtg aggtctggtt ttaacgcggc ccggggtgct gtttcttctg  10560
cgatgaattc tatccggggt gttgtgtctt cggtggcgtc tgctgttggt gggttttttca  10620
gttcgatggc gtcagggtt cgtagtgtg ctgtgcgcgg gtttaatggt gcccggagtg  10680
cggcttcttc tgctatgcat gctatgggt ccgctgtgtc tagcggggtg catggtgtgc  10740
tgggtttttt ccggaatttg cctggcaata ttcggcatgc tctcggtaat atgggtcac  10800
tgttggtgtc tgctggccgt gatgtggtgg ccggtttggg taacggtatt aagaatgcta  10860
```

```
tgagtggcct gttggatacg gtgcgtaaca tgggttccca ggttgctaat gcggcgaagt   10920
cggtgttggg tattcattcc ccgtctcggg tgtttcgtga ccaggttggc cggcaggttg   10980
ttgccggttt ggctgagggg atcaccggga atgcgggttt ggcgttggat gcgatgtcgc   11040
gtgtggctgg acggcttccg gatgctgttg atgcccggtt tggtatgcga tcgtctgtgg   11100
gctcgtttac accgtacgac cggtatcggc gtgcgagcga aagagtgtt gtggtgaatg    11160
tgaatgggcc tacttatggg gatcctgccg agtttgcgaa gcggattgag cggcagcagc   11220
gtgacgcttt gaacgcgttg gcttacgtgt gattgagggg gtgttgtgca tgtttattcc   11280
tgacccgtct gatcgttctg gtttgactgt gacgtggttt atggatccgc tgtttggcga   11340
cgagcgtgtg cttcatttga cggattatac gggtgcgtct cctgtcatgt tgttgaatga   11400
ttcgttgcgc ggtttgggtg ttcccgaggt tgagcatttt tctcaaacac atgttggggt   11460
gcacggctcg gagtggcgcg ggtttaatgt gaagcctcgc gaggtgacgc tgccggtttt   11520
ggtgtcgggt gttgacccgg atccggatgg cgggtttcgt gacggttttt tgaaagccta   11580
tgacgagttg tggtcggcgt ttccctcggg cgaggtgggg gagttgtcgg ttaaaacccc   11640
gtctggtcgt gagcgtgtgt tgaagtgccg gtttgattcg gtggatgaca cgtttacagt   11700
tgatccggtg aacagggggct atgcgcgcta tctgttgcat ttgacagcgt atgacccgtt   11760
ttggtatggg gaggagcaga agtttcgttt tagtaacgcg aagttgcagg attggttggg   11820
tggcggccct gtcggcaagg atggcacggc gtttcctgtg gtgttgacgt ctggtgttgg   11880
ttctggctgg gataatctgt ctaataaggg tgatgtgcct gcgtggcctg ttattcgtgt   11940
tgagggcct ttggagtcgt ggtctgtgca gattgatggt ttgcgtgtgt cttcggatta    12000
tcctgtcgag gagtttgatt ggatcactat tgatacggat cctcgtaaac agtctgcgtt   12060
gttgaacggg tttgaggatg tgatggatcg tttgacagag tgggagtttg cccctatccc   12120
gcctggcggt tcgaagagtg tgaatattga gatggttggt ttgggtgcca ttgttgtgtc   12180
ggtgcagtac aggttttga aggcttggtg aatagttgat gactgatctg gttccgcatg    12240
taacattgtt tacaccggat tatcgccgtg tggcgcctat caattttttt gagtcgttga   12300
agttgtcgtt gaagtggaat ggtttgtcga cgctggagtt ggtggtgtct ggtgatcatt   12360
ctaggcttga cgggttgact aggccggtg cacggctggt tgttgattat ggtggtggcc    12420
agattttttc tgggcctgtg cgtcgggtgc atggtgtggg tccgtggcgt tcttcgcggg   12480
tgactatcac gtgtgaggat gatatccgcc tgttgtggcg tatgttgatg tggcctgtga   12540
attatcgtcc tggtatggtt ggtatggagt ggcgtgccga cagggattat gcccactatt   12600
cgggtgcggc ggagtcggtt gctaagcagg tgttggggga taatgcttgg cgttttccgc   12660
ctggtttgtt tatgaccgat gatgagagtc gtggccgcta tattaaggat tttcaggtgc   12720
ggtttcacgt gtttgccgat aagttgttgc cggtgttgtc gtgggctcgg atgactgtca   12780
cggtgaacca gtttgagaat gcgaagtttg atcagcgtgg tttggtgttt gattgtgtgc   12840
ctgctgtgac ccggaagcat gtgttgactg ccgagtctgg ttcgattgtg tcgtgggagt   12900
atgtgcgtga cgcccctaag gctacttcgg tggtggttgg tggccgcggc gagggtaagg   12960
atcggctgtt ttgtgaggat gttgattcga tggccgaggg ggattggttt gatcgtgtcg   13020
aggtgtttaa ggatgcccgt aacacggatt ctgaacatgt gcatctcatc gatgaggctg   13080
agcaggtgct gtccgagtcg ggggccacgt cggggtttaa gatcgagttg gctgagtcgg   13140
atgtgttgcg gtttgggccc ggcaatctga tgccgggtga tttgatttat gtggatgtgg   13200
```

```
gttctggccc tattgcggag attgttcggc agattgatgt ggagtgtgta tcgcctggtg    13260
acgggtggac gaaggtgact cctgttgctg gggattatga ggataatccg tcggccctgt    13320
tggctcgccg tgttgccggt ttggctgccg gtgtgcggga tttgcaaaag ttctaaaaag    13380
attaggggtt tgttgtgggt attgtgtgta aagggtttga tggtgtgttg accgagtatg    13440
attgggctca aatgtctggt ctgatgggta atatgccgtc tgtgaagggc ccggacgatt    13500
ttcgtgtcgg cacgacgatt cagggtgcca cagtgttgtg tgaggtgttg ccggggcagg    13560
cttgggctca cggggtgatg tgcacgtcga atagtgttga dacggtgacg ggccagcttc    13620
cgggccctgg tgagacccgc tacgactatg tggtgttgtc tcgggattgg gagcagaaca    13680
cggccaagtt ggagattgtt cccgggggggc gtgcggagcg tgcccgggat gtgttgcgtg    13740
ccgagcctgg cgtgtttcat cagcagttgt tggctacttt ggtgttgtcg tctaacgggt    13800
tgcagcagca gctggatcgg cgtgctatag cggctagggt tgcgtttggg gagtctgctg    13860
cgtgtgatcc taccoctgtg gagggtgacc gggtgatggt tccttcgggg gctgtgtggg    13920
ctaaccattc gggtgagtgg atgttgttgt cacccaggat agagacgggt tctaagtcga    13980
tcatgtttgg cgggtcggct gtgtatgctt acatgatccc gtttgagcgg ccgtttagta    14040
gtgcgcctgt tgtggtggcg tctatggcta cggcggctgg gggtacgcag cagatcgatg    14100
tgaaagccta caatattact aataaggatt ttagtttagc gttttattacg aatgatggtt    14160 ctaagccttc tggtgtgcct gcggtggcta actggattgc tgtgggcgtg tgaccgggct    14220
gttgttgtgg cggatggtgt gatgttgggg gggctgtggt gtcgtggttt actcctgcac    14280
tggtggcctc tatttgtacc gcgttggcca cgattttggg ttctgttcag gcggtcacat    14340
cccgttctag gcggcgtttg cggcggctgt cggctcaggt ggatgcgatg gaagagtata    14400
cgtggggtgt tcggcgtgag gttcgccggt ttaactcgcg gcttcctgac gaggtggagc    14460
ctatgcgtct tcctgatgtg cccgagtttt tgaaagatac tgttgatggt ggaggtgagt    14520
agggttgagg gagttggagg aggagaagcg gcagcgccgc tcgtttgaga aggcttccct    14580
gatactgttg ttcctgtcgc ttgtactgtt ggcggtggtt gccggggggtg ctttacggta    14640 cgggtctgtg gcttcccaaa gggattcaga gcaggctaaa gcccagtcga atggtacagc    14700
cgctaaaggt ttggctgccc gtgtgaagca ggcgtgtgcc tctggcgggc aggagtctgt    14760
gcggcttcac cagtctggct tgtgtgtgga tgctgtgcgt gttgagcgga gtgtgcatgg    14820
tgtgccgggc ccggccggtg agcgcggccc gcaaggccct gcaggtgttg acggccggga    14880
tggtgttaat ggttcggctg ggctggttgg ccctgttggt ccgcagggtt ctcccggttt    14940
gaatggtgtg aagggtccgc agggttctgc cggtgcgaac ggatcggatg gccatgatgg    15000
tgttccaggt cgtgcaggtg ctgacggtgt gaacggcgct gatggtcgag atggtcctgc    15060
cggtaagcgc ggtgatgtgg gcccttcagg tccggccggc ccgcaaggtg cacagggtga    15120
acggggtcct attgggcctc agggtccgca gggttctgcc ggtgcgaacg gatcggatgg    15180
ccatgatggt aaagatgggc gttctgtggt gtctgtgtac tgttccgggg ccgcctggt     15240 tgtgaaatat agtgacggta tggtttctac catatcgggt tctgtggcct gtgagggtgt    15300
gaaaccgtcg cctatagtga ctatatcatc ccacaaatag aaaggagtgg ctgtgatggt    15360
agtgtttggt ggtggtgtgt ggtgaggttt attcctgctg cgcatcattc tgccggctcg    15420
aatagtccgg tgaatagggt tgtgattcat gcgacatgcc cggatgtggg gtttccgtcc    15480
gcttcccgta aggggcgggc ggtgtctacg gcgaactatt tcgcgtcccc atcggcgggc    15540
ggttctgccc attatgtgtg cgatatttcg gagacggtgc agtgcttgtc ggagtctacg    15600
```

```
attgggtggc atgccccgcc gaatccgcat agtttgggta tcgagatttg cgcggatggg   15660
ggttcgcacg cctcgttccg tgtgccaggg catgcttaca cgagggagca gtggctggat   15720
cctagggtgt ggcctgcggt ggagaaggct gccatcctgt gtagacgttt gtgtgacaaa   15780
tataatgttc cgaaaaggaa gcttagtgca gccgatttga aggctggcag gcggggtgtt   15840
tgcgggcatg tggatgttac ggatgcgtgg catcagtcgg atcatgacga tcctgggccg   15900
tggtttccgt gggacaaatt tatggctgtg gtgaatggcc acggcggcgg ttcaagtagt   15960
gaggagttaa cggtggctga tgtgaaagcg ttacataatc agattaaaca attgtctgct   16020
cagcttactg gttcggtgaa taagctgcat cacgatgttg gtgtggttca ggtgcagaat   16080
ggtgacctgg cgcgccgtgt tgatgccttg tcgtgggtga agaatccggt gacggggaag   16140
ctgtggcgca ctaaggatgc cctgtggagt gtctggtatt acgtgctgga gtgtcgtagc   16200
cgtattgaca ggcttgagtc tgctgttaac ggtttgaaaa agtgatggtg gtttgttgtg   16260
ggtaaacagt tttggttagg tttactggag cgggcggcta agacttttgt gcaaacgttt   16320
gttgctgtgt tgggggtgac ggcgggtgtc acctatacgg cggagtcgtt tcgcggtttg   16380
ccgtgggagt ctgccctgat cacagctacg gtggctgcgg tgttgtcggt tgctacatcg   16440
tttggtagcc cgtcgtttgt ggctggcaaa cctaaaacca cgcctgtgga tgcgggtttg   16500
gttccaccgg atgatggggg cttggttgag ccgcacatgg ttgatgtgtc ggatcctggc   16560
atgatcgagc cgattgatga tgcggatgtt gtcggctatg tgccgaggcg tgccgccgag   16620
tcggaggttg acacggtaga gtctactgtt gcataattga atatgtgtgt gccccagcgg   16680
tgctgccacg atctgtggtg gttgccgctg gggcactatt tttgtgtcta tagtattcta   16740
tgattcgttg ttgttgatgg tttcttcgat cagctggtcc aggtggaggc aggtagagat   16800
cgtttcgttg gcctggtgca gaacatcctg gccgataaca ttttgtggt tgtcgcggtg    16860
gcagatgatt gactgcatga tatcgtcggc ttccgattgt agtagtttgg tttggtatgc   16920
gattcctgcc agccaatcta tggcttcctg gcttgcccgt gtgtcgtctg gaatgccacg   16980
ggtgttgctg ttgtttgggt atcctgcact gtcgcagtcc cacaagattt cgctgcactc   17040
gtctagcgtg tcctggtcga tagcaaggtt gtcgaggctg acttctttga cggtaaggtt   17100
cacgttgtcg agtgagatgg gtacacggta ctggttttcg acaccgtcaa caatgttttg   17160
cagctgttgc atgttggttg gctgttgttg gatgattcgg tgtactactg ttttgagggc   17220
agtgtagggg atattggttg tgttgttcat ggttttatcc catccctgtg ttgtcgtcgt   17280
tgccgtcttg gtagtatcga ctgtttgcgt atcctgtgag ggtgatgagt gtttggtctg   17340
cccactgttt caccgtctgc cgggttactc cgagtcgttg ggctgccacc gaataggttt   17400
ggtcgtaccc gtatacttca cggaatgcgg ccaggcgtgc caaatgtttt cgctgtttgg   17460
atggctggca ggtgagggtg tagtcgtcga tggcgagctg taaatcgatc atggtaacga   17520
tgttgttgcc gtggtgttgt ggcgcggttg gtggggtgg catgcctggt tcgacggagg    17580
gtttccatgg gcctccgttc cagatccatt gggcggcttg gatgatgtcg gcggtggtgt   17640
aggttcggtt cactggtcat cccctgaata ggttgtcgag gttgtctggg ttgctggtgt   17700
tggtggtgtc gaatcgtccc acacagtggc agtagtcgta catgagtttg ataatgtgtt   17760
ggtggtcgcc gaggtaggtg tttccgctga tactgtaggt ggctgtgccg tctttactga   17820
tggtgtattt ggcggtgatg gtttcgggtg tttctgtgtt ggtgatgatg gcggtggtgg   17880
tggcgcctac tgtttgtagc ctggtggttt gggtgccgtc gtcgaggatg gttgtgacca   17940
```

```
tggtgtgtgt tctccttttta aatgcttgtt tggttgtcgg ctagatgaat gatatcggat    18000
aaaggtttcg gctggtctag gtgttgtatg gttttgttgg ctagccgttt ggctaccctg    18060
tagcacattt tggtgtagtg tttgttgtct aggttgtggt attgttcccg caccgcaata    18120
tatagtaggg agtcttggta gaggtcgtct gcactgattg cggggtagtg tccggctgtt    18180
ttggtgcatg cccggtggag tgtgcgtaga tgatggtctg tggcccacac ccacgatgcg    18240
gtggtggcta ggtcggcttt tgttggtcgt ctgctcatag catctctttc atctggctat    18300
ctggtagttg tttggtgttt tgttgttgat agtgtagcac acgagtccgg ggtttccggt    18360
ggtgcctgtg cggtgccgga accatgtgga ttcgccttcc atggatgggc attggatgaa    18420
ggtgcgttgt ccttgctcag agatttcgag gtggtgccgg tgcccggcca tgagaatatt    18480
agatacggtg ccgttgtgga attcttggcc gcgccaccat tcgtattgtt tgccggtttt    18540
ccattggtgt ccgtgggcgt gcaggatttg tgtgcctgcc acatcaacgg tggtggtcat    18600
ttcgtctcgg ctggggaagt ggaagtgaag gttggggtat tggttgttga gctggtaggc    18660
ttctgcgatg gcgcggcagc agtccacgtc gaaggagtcg tcgtaggtgg tgacgccttt    18720
gccgaagcgt acggcttctc cgtggttgcc ggggatggat gtgatggtga cgttggcgca    18780
gtggtcgaac atgtggacga gttgcatcat ggccatgcgg gtgagcctga tttgttccgt    18840
caagggtgtt tgtgtgcgcc aggcgttgtt gccgccttgt gacacgtatc cttcgatcat    18900
gtcgccgagg aaggcgatgt ggactcgttc gggtttgcct gcctgttgcc agtagtgttt    18960
tgcgactatg agggagtgca aatagtcgtc ggcgaagtgt gctgtttctc cgccggggat    19020
gcctttgccg atttggaagt ctcctgcccc gatgacgaag gccgcagtgc tgtagtcggt    19080
gtgggtgttg tcggctggtt ttgggggtgt ccatttggct agtttatcga cgagttcgtc    19140
tacagggtag gggttggttg cgggttggtg gtcgatgatt ttttgtatgg atcggccggt    19200
ttctccgttc ggtaaggtcc attcggagat gcgtgtgcgg cgtacagtac cattggctag    19260
attgtcgtcg atggtgtcga tggcgttgtc gtggttggct agctgtgtga gtagccggtc    19320
tatattgtct atcactggtt ttcctcttct gtttgtgggg tggtgttggc ttgtttgcgg    19380
cgatagtctt tgatgacggt ggcggagatg gggtatccgg cttgggtgag ctgttttgct    19440
agccatgagg cggggatggt tttgtcggcg aggacgtctg cggctttgtt gccgtagcgt    19500
tggataaggg tttcagtttt ggttgccatg atgtcctagg ggttgtgtgg tgggctgcca    19560
tcctgtgcgg cagtcgccgt cgtgtcctgg tttgcgtgtg caccatgaga cttcgccggc    19620
attgtggatg atggcacggc cgcatatgac gtcatgtagg tgttcgggaa acttatcgtt    19680
gttgttgtcc ccgtacatgt cgatcaagtg ttgggtttta gtaaccatca tgtctcctat    19740
gtgtgaaaga gtgtgcaaat actatgctgg tgtcatggat gtttatgcgg gtatggtttt    19800
catcaccttg ctgaacgtta cttggttact gtacatcatc tgggtgattt cctgatccgt    19860
tttgtcgggg tgctgttttc gcaggtttgc ccattggcag gcgttgtcgg tttcttgctg    19920
gagccgggtg agattgtttt cggtgatgat ttgtttccac attgtccacg agacgtcgag    19980
tcgtttgagc atgtcgatgg ctggcacgtt gaaggagttg aggaagagta tttcctccgt    20040
gtagtagtct ttttcgtatt ggtcccatcc gcttcggtgt ctgttgggct ggttttt ggg    20100 gtaggcttcc cggcatactt tgtgcaaacg tttggccatg tctttgggta gcctaatgtc    20160
ggggttggcg cggatcatgg atcgcatccc atcataggtg gtgccccagg tgtgcatgat    20220
atgtagtggg tcttccaccat cagcccattt ttctgcacag atggcgaggc ggatacgcct    20280
cctagtggcc ttactcgtgt cgcggcggcc ggggatgggg catgtgtcga gggggtccat    20340
```

```
gatgctttt  atgcctttct  tggagtgatg  ttttgtttgt  ctggttttat  tgtagcactg   20400
tgtctagtgc  ttgtgtcaac  cctgttttc   cggcctgcag  ataggtgtct  gtgacatccc   20460
ccagggtgag  gggtacgtgt  atggcttggg  ggagtgccgt  ctggatggtt  tgtgccatct   20520
ggtcgcctgc  tttgtcgggg  tcggaccaga  tgtagatgcg  gtcgtagcct  tcaaaaaatt   20580
tggtccaaaa  gttttgccac  gaggttgcgc  cgggtagggc  tacggccgac  catccgcatt   20640
gttcgaggat  catggagtcg  aattcgcctt  cgcaaatgtg  catttcggct  gccgggttgg   20700
ccatggcggc  catgttgtag  atggagcctg  tgtccctgc   cggggttaga  tatttggggt   20760
ggttgtgggt  tttgcaatca  tgctggagtg  agcagcggaa  acgcattttt  cgtatttcgg   20820
ctggctcccc  ccagacgggg  tacatgtagg  ggatggtgat  gcactggttg  tagttttcgt   20880
ggcctgggat  ggggtcattg  tcgatgtatc  caaggtggtg  gtagcgggct  gtttcttcgc   20940
tgatgcctct  tgctgagagg  aggtcgagta  tgttttcgag  gtgggtttcg  tagagggctg   21000
aggctttctg  gattcggcgg  cgttccgcaa  tgttgtaggg  ttgtaggctg  tcgtacatta   21060
gggttttctt  tctctagttg  ttgtttcagt  tgggcgagtc  cgcctccgat  accgcatgtg   21120
tggcagtacc  agacgcccctt  gtcgaggttg  atgctcatgg  agggctggtg  gtcgtcgtgg   21180
aacgggcaga  ggatgtgttg  ctcgttcctg  gaaggattgt  accgtatctg  gtgggtgtcg   21240
aggaggcggc  gggtgtcaga  ggtgtgggag  gagctcgttg  agggttgata  ccacataggc   21300
ttcgctccag  ggtttgttgc  gctgtttcat  gacgacgagt  ccgatggtgg  aattgtttg   21360 tttgtttcgg  tgtgtttcgt  agttgcgtgc  ctcccggctg  gcttgtttca  cgaattcggc   21420
gaggtgtgcc  tgtccggctt  tcgcctcgat  aatgtaggtt  tgttgccgg   ttgtgaggat   21480 gaggtcgcct  tcgtcttcgc  ggccgttgag  gtggaggcgt  tctatatcat  ggccggtgtc   21540
gcgtagctgg  tggaggagtc  tggtttccca  ttcggctccg  gctcggcggt  tgcgtgcctg   21600
ttgtgtcgac  atgatagtcc  tttgtggtgt  tcggtcatgt  tccatggctg  tttttctgcg   21660 agggcccga   agaatgtgta  ttcggggtag  gctcgtagtc  gttcgtatcg  ggttccgtct   21720
gggctggatt  tgcctgtgcg  ctgtttcaac  actgcgatgc  gtgcctctgc  cggtatcgtg   21780
agcccgttgc  cgttgtcctc  gccaccataa  agtgagactc  cgaggatgag  ttgtggtttt   21840
tcggagaggc  cgttttgat   ttccctgcgt  gctggcgggt  gttcgatgtc  ggttccggtt   21900
ttgtcggttg  cgtggtgtgt  gacaataatg  gtggagccag  tatccctgcc  caatgctgtg   21960
atccattgca  tggcttcttg  ctgtgcctgg  tagtcggatt  cgcagtcttg  gatgtccatc   22020
aggttgtcga  tgacgatgat  gggtgggaag  gtgttccaca  tttccatgta  ggcttgcaat   22080
tccatggtga  tgtctgtcca  tgtgatgggt  gactggaatg  agaatgtgat  gtgttggccg   22140
tggtggatgc  tgtctcgata  gtattctggc  ccgtagtcgt  cgatgttttg  ttgtatctgt   22200
gtggtggtgt  gttgggtgtt  gagtgagatg  attcgtgtgg  aggcctccca  gggtgtcatg   22260
tcccctgata  tgtagagggc  gggctggttg  agcatggcgg  tgatgaacat  ggctagccct   22320 gattttggc   tgccggaccg  ccccgcaatc  atgacgagat  cccctttgtg  gatgtgcatg   22380
tccaggttgc  ggtagagggg  ttctagttgt  ggtatgcggg  gcagtcggc   tgcggttgg    22440 gaggctctct  cgaaggatcg  ttgtagagag  agcatcggga  ccttatctat  ctattggttg   22500
gatgtgtatt  ggtggtcaga  tggagtcgat  atcgatgtca  gtagaggctg  tggtgtcgtc   22560
tagctggccg  ttatcgcgct  tgtctacgta  ttcggccacc  ttatcgtaga  tggcgtcgtc   22620
taatggtttg  agcacaaccg  cgttgaagcc  gttttggtg   cgtacggtgg  cgagtttgaa   22680
```

```
ggcctgctcc tcgccaaggt aggtttctag atcgcggatc atggagtggg ggcggtcgtt    22740
gttgccgcgt gctttctcga taatggcgtt ggggatggtt tctggggtgc cgttgttgag    22800
atcgtctagg gtgtggaaga ttgtgacatc agcgtagatg cggtctgcga cctgtccacc    22860
gtagccttcg gtgttgtgtt cgacgtcgtg gactttgaag gcgatggcgg tggcgtcctg    22920
gtttcgggag gggttgaaga aggtgctgtt actgttgttg tttcggtagt ttgcgagtcc    22980
cattgttgtt tcctttactg tttgtgttgt tttgtttgtt ggtttgtgtc ggtttatcgg    23040
gtgaggctgt ttcgtttatt ccggaaagct tcggacacgt cactgttact agtgatgatc    23100
tttttgtact gtttcagaag gtcggctagc tgtgccttgc ttgtggcatt gttaattttg    23160
tctatgacga tgctgttttc gtttgatgcg atattgttta cgtagtcttt ggcggcttgg    23220
ttgtatcggt cttggaggat gatggatgct gtggcgatca gtgttgccag gtcccagttc    23280
cttgccgcgg agctgttttt gagtccgcct aacaggtcga tgatagtctt ctttacctgg    23340
tcggcggtgt ctccgcggat gacggtccat ggggcggcgt agtcgcctcc gtatttgagt    23400
gtgacggtga atcggtcttc gtctgtgttg tcggtcactg gtgctccttg tcttctttttg    23460 ttggggctgt gatggtggtt tctataggga acctgtaggc atctttcccg ttgacagccc    23520
agcaggcgtc ctggacgggg cagcctttgc agagtgctgt gacgtggggt acgaatatgc    23580
cttggctgat tcctttcatt gcttgactgt acatggatga tacatgccgg taggtgttgt    23640
tgtcaagatc gtacagttcg gtggccgttc cctgcttggc ggactgtttg tctgttttgg    23700
ttgatgcggg tgtccaaaac atgccttttg tcacatcgtt gccgtgttgt tctagcatgt    23760
acctgtatgt gtgcagctgc atactgtcgg cgggtagacg gccggttttg aggtcgagga    23820
tgaaggtttc gccggtgttg gtgtcggtga aaacgcggtc gatgtagcca acgatctggg    23880
tgccgtcctg gagggtggtt tctaccgggt attcgatgcc cggctcgccg tcgataacag    23940
cgatagcata ttctgggtgg ttgctcctcc atgttttcca gcggtccaca aaggtggggc    24000
cgtaaaccat ccaccagtcg tagtctttct tgtgtggccc gcccgactcg cacatgtttt    24060
tgcatattct gccggagggt ttgatttctg tgccttcgga ttcggcgagg gcgacttggg    24120
tgtcgaaaat gttttttgaag gatgcaagtt tgtctggcag tgcagggtat tcggcgggat    24180
tgtacaggtg taggtcgtat tgttcggtga tgtggtgtat ggcgcttccg gcgatggtgg    24240
cataccaggt gtggtgttgg gcatggtagc cgtgggatag gcgccatttt tctccgcatt    24300
cggcccactg tgacagtgat gagtaggaga tgtggcctgg atggttgatg gttttcgggt    24360
attgtgctag aggcattact ggtcgccttt gtgggtgttc catgggttgc gggtgtcttg    24420
gccggcattg tgttgctggt atgcgaggag tgcgaggcag tgccaggcag catgtgccag    24480
atgcggcaaa tgtgattcgt ggtcgaggtt gttgccttgc tgccatgata gtaggtgccg    24540
gtagagggcg tcaacgctgt ggctccacgg gtatcctccg gtccagttgt tgtcgccgta    24600
tttggtggca ccgtatccgg ctacttcgcc tagggcgtga agggatgcgg ggtcgatgag    24660
ggagagcctg cagagtttca attcttttcg ggcaccgctg ttggggtcgg tgtacatgcg    24720
ggtgggctca tccatgagat gtgtgctcct taagggtggg ttactggttg ttgtgggcga    24780
gtgctactgc gagaataatg atggcgaggg tttcagcgat cagtatgggt gttgtgatca    24840
tttgctgtct ttgggctggt aggtgagggt tgaggcaccc aggagggtgg cgagggcgca    24900
tgcggcgatg atggcgaggg ctgccttgtg tggggtgctg gttgcgtaca tccatgtgat    24960
gatgccgcct tggatccagg ctaggctggt gaagaacgtt tcgtaactgt gtagctcaat    25020
gttgttgttg ggtgtgttca tgcttgctcc tgaagaatgg tgttgatggt tttataaatg    25080
```

```
ttgtacaggt cggtttcgat agataacagt tggttgattt ggtggtcgag gttgatgtct   25140
gggttgaggg tgttgatgcg ggaggcgata tcggtggctg tgcgtagtgt gccgccggtg   25200
tggtgaataa tgtgtgccgt gtcggcgagt ccggtggtga cagcgtagtg ggagaggata   25260
ggcatagcgg gggaatgttc cttggcgggt tactgttgcg ggttgatgtt gaggtcggtg   25320
acgtgcgggt ggtcttctgt tccggtgacg aggcagtgga cggtgacggg tagtttggat   25380
gcgccgggct gtttcatggt ggcgccgtag acgatgctga atgtgtcttt accgatggtt   25440
ttgtggagtt ggaggtcgat gtcggggttg ccgttccagt tgacgccttg tgctgcggcc   25500
tgttgttcgg ctttgcggtt gcaggtgtgt gctgccgtga tcatggtgag tccggttgcg   25560
gtttcttcac cccttgcttg ggcttgcttg tgggttttgg cctgctcggc ttgtagggat   25620
cgggtggcgg ctgcctgccg tgccgctttc tcggctttgc gctgttgggt agtcttgggg   25680
gtccattcgg tgttggctgt ggtggcctgt ggggcgggtt gtgaggcgag tgcggattg    25740
tcgtctgggg ctggcaggaa ggatgcggcg gcaatgatgg cggctgtgat tccggcgatg   25800
gtgtagccgt ttttcttgtt catgactgtt gtccccttc cggggtgttg ttcgttgctg    25860
acatgattaa tacttccagt gactggacct catgtcaaga ctgcgctcaa atgttgtgag   25920
cgtttcctgt atggttagat gttttatcgg gcacacaggg tgagtagatg gccaacattg   25980
atgcaggtca cgttccagta gagttgtgtg gcttcaccgc cggtgagcgg cttccactcg   26040
ttgtggctga acacggtgcc atcggatgct atgaatgtgt tggggcgtag cttgtgaagc   26100
tcggcttcca cgctctgccg gtaggcttcg gcgaggccct caaaatccat gtggtcgcag   26160
gagagatttt cgaggcgtgt caggtcgaag ggtgtggggc agtcgtagct ggcggggtg   26220
tagagctggg tgaagtggtc ggcgatcttc tgcatgatta tttcctttc gttgctgata    26280
acgttgttga gggtttatcg ggtggatgcg acaaggatgg cgtctacatc gatcacgtcg   26340
atcatgtcgt ggagttcctc cgcttcgttc tcggcgagtg gctgccagtc gtagtcgccg   26400
tacacggcgc cgtcaagggt gacagtccac agtggccgga tgagtcgtat ggcttcttgt   26460
actttagcgt ggtacatgcg gcgcaccata tcgagatcga tgtcgtctga atggtttccg   26520
gtgaggctgt ggaggctaag cgggtcgatt tctgtctgcc tgtagaggga tgtgaaggat   26580
ggggtgatga gtgtgccatc catgggtgat gttcctttct ggattgtctt ggttgttgtg   26640
gtttctagag tgtgtgggct gcgactcaca gtcaaggctg cgctcaatcc gaatgagcgt   26700
ttcatgctgg agtgtcgggt gtgacagatg tcactgaagc ctttatggcc tctcccagcg   26760
tctcaaatct tctaggggta ggattatgca gggttgacca tactagtcga ttctagggcc   26820
attctagggc gtctgagggg tatatctggg tgatagcagg tgtggcagat gatctagcga   26880
gtcaaggtgc cgagcttaga cataagatct atcatctagg tgtgtgagat gtatcacact   26940
ctcctggctt ggtgtgcact ctcgaggcca ctctgccgat ctggcgtgga gggtgtagcc   27000
cagaaatgcc gtttaaatcc ttcacgcgga gcctaggagc gccttgcagg gtggggcta    27060
ggtatttata cccccagcat attctgatcg attctatacg ccccagaag cctgatacac     27120
gattcgctat ccaggcgcag atcatcagcc cctatcctgc ttagctaagc ctcaactatg   27180
tggacagtgt tggatgctaa gagggaagaa ggatacggta aaagaaagaa ggggagtat    27240
cagccttcac accggaggta cttaagttca ccttagagac ttagcactga gcattgagca   27300
ctgagcagga tcagcccaga aaggggtaca cgccatcagg ggaggcttga gagtacgagg   27360
agccctagcg acgagtactc gaaagcctga gggaatacc tcagcactga tgggcctagc    27420
```

-continued

```
gtgttcggaa aggacacagg agtacagtgt gacagtcttt ccgggagcta aactccttcc    27480
ggctagggca acacccgtc ctaggctagc ccacaccctc atctgttaac cttccgttca    27540
ttaaacgtta aggaaacttt taggtttgat ttttggacct ttactaccaa aaacaccegt    27600 ttacacccct caaacccgcc tatagagcca aacgccggtg ttgagggtat ctctacctag    27660
tgtgataggc tggacaggta gccagctgga cgcaaggccg aaatccgctg acgcggcttt    27720 caccettaca tccatcagtc taccaaacac tttaaagctt caaggcttag cgctaagccc    27780
ttaaaacctt aacgcttagc accgagccct tgaggggctc ggcatcagtc ttaggtactt    27840
taagtaactt taaaaccttc aaggcttagc ccttaaggat ctaagttact cttaaagctt    27900
taaagtctta aaataaatat ataaccttaa tagttaaacg ttaaaagctt taaaccttaa    27960
cacttaagtt aagtataaaa ccttaaaggc ttagcactta aggatataaa ctttacatca    28020
gtgtttaaga ctttaaaact taaagtaatt attaaaactt aaaggtttat aagctttaag    28080
cacttaaagt aactataaga ctttaaagac cttaagtact taaagttaac catcagtctt    28140
aaactttaat attataccta taagtcttaa agcttatagg tataaaagtt ttagaagagc    28200
taaggggtta acttctttac ttctctactc tctttggttc tttctctctt ctcttctttt    28260
cttcatcagg ggagaagaga aacctttttac cgtcaacgct gatgggcttt tcgccgtgtg    28320
actcgtgtgc ttctggtcgc aagctcccat cgcacactcc ccacactctt tcacccgtgt    28380 ccccttttcag gcttagcatg ttcggctgaa ggcgtacggc gtgtcacgcc aacacccctta   28440 acaccaggta agacttaaag tacatattat atgtagaaga ctttaaaacc ttaagggtgt    28500
tcccgcttgg cccgtgtcct ttaacgctag gcgctaagcc tgaaacgcga acacccatcc    28560
acccccattt tgcttccgtg tccttctctt tttgacaccg ctggggggcg atgtgatctt    28620
tctcacatgc caggggttag tggagaaaac aaacacccca ccacaaacag aacacccct    28680 caaacgaaca aaacagggcc tagaatcgaa tagaagggca ccgtagagt attcctaccc    28740 ccaacacgtt ccaggctgtt acaggagcaa tgagaggctc acaggggcca taggagatca    28800
gggggcgtga tggcacacac caaccgcaca gccagccaag cccaccggcg ctggcgggcg    28860
cgactcatca cccaagcacg caagcaaggc caaaccgaat gcccactctg cggagcccag    28920
atagcctggg acacacacga cctgccaacc agccccgaag ccgaccacat cacacccgtc    28980
agccgcggag gactcaacac cctcgacaac gggcaaatca tctgcagaac atgcaacaga    29040
agcaaaggca atcgcagcga accaaacatt agtttccaac aacaaaccac aaaaaccttg    29100
atttcatggt gaaaaaaccc acaaacccca cgggaaccac cccctgcaca ccc    29153
```

<210> SEQ ID NO 5
<211> LENGTH: 29109
<212> TYPE: DNA
<213> ORGANISM: Bacteriophage 1894

<400> SEQUENCE: 5

```
tcccttttgt ggattgtctg tttgtcgact ttttgtgttg gtggtgagtg ttgtgcagcc      60
tgagcttcct gggtctcgtg agtggtgtgg ggagacgcgt cagtggtggc gtgtgtgggg     120
tgaggatagt cgcgcgcagt acgtgtctga tgaggagtgg ctgtttctca tggatgctgc     180
ggtgattcat gattgtgtgt ggcgtgaggg tcgcgcggat ttggtggctt cgttgcgtgc     240
tcatgtgaag gcttttatgg gcatgttgga tcgttattcg gttgatgtgg cgtctggtgg     300
ccgtggtggg ggttctgcgg tggcgatgat tgaccggtat aggaagcgta aagggggccta    360 atgtcgagtg ttgttggttc tcaggttcct cgtcaccggg tggctgcggc gtattcggtg    420
```

-continued

```
tctgctggcg gtgatgctgg ggagttgggt cgtgcgtatg ggttgacgcc tgatccgtgg    480
cagcagcagg tgttggatga ttggctggct gtcggtggta atggcaggct tgcttcgggt    540
gtgtgtgggg tgtttgtgcc tcgccagaat ggcaagaatg cgatccttga ggttgtggag    600
ttgtttaagg cgactattca gggtcgccgt attttgcata cggctcacga gttgaagtcg    660
gctcgtaagg cgtttatgcg gttgaggtcg ttttttgaga atgagcggca gtttcctgac    720
ttgtatcgta tggtgaaaac gatcagggcg acgaatggtc aggaggctat tgtgttgcat    780
catccggatt gtgccacgtt tgagcgtaag tgtggttgtc cggttggggg ttcggttgag    840
tttgtggccc gttctcgggg ttctgctcgc gggtttacgg ttgatgattt ggtgtgtgat    900
gaggctcagg agttgtcgga tgagcagttg gaggctttgc ttcctacggt gtctgcggct    960
ccttcgggtg atccgcagca aattttttg ggtacgccgc ctgggccgtt ggctgatggt   1020
tctgtggtgt tgcgtttgcg tgggcaggct tgtcgggtg gtaagaggat tgcgtggacg   1080
gagttttcga ttcctgacga gtctgatccg gatgatgtgt cgcggcagtg gcggaggttg   1140
gcgggtgaca ctaatccggc gttgggtcgc cgcctgaatt ttgggactgt cagcgatgag   1200
catgagtcga tgtctgctgc cgggtttgct cgggagcggc ttggctggtg ggatcgtggc   1260
cagtctgctg cgtctgtgat tccggcggat aagtgggctc agtcggctgt ggatgaggcg   1320
agtttgtctg gcggtaaagt gtttggtgtc tcgttttctc gttctgggga tcgggttgct   1380
ttggcgggtg ctggccggac tgatgctggt gttcatgttg aggttattga tgggctgtcg   1440
ggaacgattg ttgatggtgt gggccggttg gcggactggt tggcggttcg ttgggtgat   1500 actgaccgga ttatggttgc cgggtctggt gcggtgttgt tgcagaaggc gttgacggat   1560
cgtggtattc cgggccgtgg cgtgattgtg gctgatactg gcacctatgt ggaggcgtgt   1620
caggcgtttt tggagggtgt gcgttcgggt gttgtgtctc atccgcgtgc cgattctcgc   1680
cgtgacatgt tggatattgc ggtgaggtcg gcggttcaga agaagaaagg ctctgcgtgg   1740
ggttggggtt cctcgtttaa ggatggttct gaggtgcctt tggaggctgt gtcgttggcg   1800
ttttgggggg ctaaacgtgt tcgtcgtggc cgtcgggagc gtagtggtag gaagcgggtg   1860
tctgtggtat gaactcggat gagttggctt tgattgaggg catgtacgat cgtatccaaa   1920
ggttgtcttc gtggcattgt cgcattgagg gctactatga gggttctagc cgggtgcgtg   1980
atttgggggt tgctattcct ccggagttgc agcgggtgca gacggtggtg tcgtggcctg   2040
gtatagctgt ggatgctttg gaagagcgtc tggattggct tggctggact aatggtgacg   2100
gctacggcct ggatggtgtg tatgctgcga atcggcttgc tacggcgtcg tgtgatgtgc   2160
atttggatgc gctgattttt gggttgtcgt ttgtggctgt tatcccccag gatgatgggt   2220
cggtgttggt tcgtccgcag tcaccaaaga attgcacagg caagttttcg gctgacgggt   2280
ctcgtctgga tgctggcctt gtggtgcagc agacgtgtga tcctgaggtt gttgaggcgg   2340
agttgttgct tcctgatgtg attgttcagg ttgagcggcg gggttcgcgt gaatgggttg   2400
aggtggatcg tataccgaat gtgttgggtg ctgttccgct tgtgcctatt gtgaatcgtc   2460
gccgtacttc taggattgat ggccgttcgg aaattacgag gtctattagg gcttacacgg   2520
atgaggctgt gcgcacactg ttggggcagt ctgtgaatcg tgattttat gcgtatcctc   2580 agcgttgggt gactgcgtg agtgcggatg agttttcgca gcctggctgg gtcctgtcta   2640
tggcttctgt gtgggctgtg gataaggatg atgatggtga cactccgaat gtggggtcgt   2700
ttcctgtcaa ttcgcctaca ccgtattcgg atcagatgag actgttggcg cagttgactg   2760
```

```
cgggtgaggc ggctgttccg gaacgctatt tcgggtttat cacgtctaac ccacctagtg   2820
gggaggcttt ggctgccgag gaatctcggc ttgtgaagcg tgctgagcgg cgtcaaacgt   2880
cgtttggtca gggctggctg tcggttggtt ttttggctgc caaggcgttg gattctcgtg   2940
ttgatgaggc cgattttttt ggtgatgttg gtttgcgttg gcgtgatgct tcgacgccta   3000
cccgggcggc tacggctgat gctgtgacga agcttgtggg tgccggtatt ttgcctgctg   3060
attctcgtac ggtgttggag atgttggggc ttgatgatgt gcaggttgag gctgtgatgc   3120
ggcatcgtgc tgagtcgtct gacccgttgg cggcactggc tggggctata tcgcgtcaaa   3180
ctaacgaggt atgataggcg atggcttcgg gggttgaggc gaggcttgcg gcgactgagt   3240
atcagcgtga ggcggtcagg tttgctggga agtatgcggg ctattattct gagcttggtc   3300
gtttgtggcg tgccggcagg atgagtgaca cgcagtatgt tcgtttgtgt gtggagttgg   3360
agcgtgccgg ccatgatggt tcggcatcgt tggctgccag gtttgtgtcg gattttcgcc   3420
gattgaatgg tgtggatcct ggtttgatcg tgtatgacga gtttgatgct gcggcggctt   3480
tggctaggtc tatttcgacc acgaagattc ttgagagcga cccggatagg gcgaatgaca   3540
caattgatgc gatggcggcg ggttttgatc gggctgttat gaatgctggc cgcgacacgg   3600
ttgagtggtc tgcgggtgcg cagggcaggt cgtggcgtcg ggttactgat ggtgatccgt   3660 gtgcttttg tgccatgttg gctacgaggt cggattatac gaccaaagaa agggcgctca   3720
ctactggaca tacgcggcgt cataagcgtg gcggtaagcg cccgtttggt tcgaaatatc   3780
atgatcattg cgggtgtacg gtggttgagg ttgttggccc ttgggaacca aatagggctg   3840
atgccgagta tcagaggacg tatgagaagg cccgtgagtg ggttgatgat cacgggttgc   3900
agcagtcgcc tggcaatatt ttgaaggcta tgcgtactgt tggcggcatg agataatttg   3960
ctgtggtttc cggttgtgcg ccgccggtta ttggtgcaca ttgttgtctc ccgcacgggg   4020
gtcaacaatg ttgtgttgtt ttccgcaagg agtgtagggt taggctatgg ccgatcagag   4080
tgttgaggaa cagaatgttg acaatgatgt tgtggagtcc ggaaaggata acggcattgt   4140
tgatacagta aaagatgatg gcgggcagga ggtagccgac aatcagttga agaatgaagg   4200
cgagggtaaa tcgccgggga ctgattggaa ggcggaggcc cgtaagtggg agtctcgtgc   4260
taaaagtaat ttcgccgagt tggagaagct tcgtacatcg agtgaagatt ctggatctac   4320
tattgatgag cttcgccgca agaatgagga actcgaagac aggatcaacg ggtttgttct   4380
tgagggtgtg aagcgcgagg tggcttcaga gtatggtttg tccagtgatg cgatcgcttt   4440
cttgtcgggt ggcgataagg agtcgcttgc cgagtctgcg aaagctttga agggtttgat   4500
cgaccatagt agtggtggcg cgggtgtgcg ccgtcttgcg gggagtgccc ccgttgatga   4560
tgttaaacga cgtgagggtg tcgcgtttgt ggatgctctt gtcaataatt ctaggagatg   4620
atttgtgatg gctgacgatt ttctttctgc agggaagctt gagcttcctg gttctatgat   4680
tggtgcggtt cgtgaccgtg ctatcgattc tggtgttttg gcgaagctct cgccggagca   4740
gccgactatt tttggccctg ttaagggtgc cgtgtttagt ggtgttcctc gcgctaagat   4800
tgttggtgag ggcgaggtta agccttccgc ttctgttgat gtttcggcgt ttactgcgca   4860
gcctatcaag gttgtgactc agcagcgtgt ctcggatgag tttatgtggg ctgatgctga   4920
ttaccgtctg ggtgttttgc aggatctgat ttccccggcg cttggtgctt cgattggtcg   4980
cgccgtggat ctgattgctt tccatggtat tgatcctgcc actggtaaag cggctgccgc   5040
tgtgcatact tcgctggata agacgaagca tattgttgat gccacggatt ctgctacgac   5100
cgatctggtc aaggctgtcg gcctgattgc gggggctggt ttgcaggttc ctaacggggt   5160
```

```
tgctttggat ccggcgttct cgtttgctct gtctactgag gtgtatccga agggggtctcc   5220
gcttgccggt cagccgatgt atcctgctgc cgggtttgcc ggtttggata attggcgcgg   5280
ccttaatgtt ggtgcttctt cgactgtttc gggtgccccg gagatgtcgc ctacctctgg   5340
tgttaaggct attgttggtg atttctctcg tgttcattgg ggtttccagc gtaacttccc   5400
gatcgagctg atcgagtatg gcgatccgga tcagactggt cgtgacctta agggccataa   5460
tgaggttatg gttcgcgccg aggctgtcct gtatgtggct atcgagtcgc ttgattcgtt   5520
tgctgttgtg aaggagaagg ctgcaccgaa gccgaatcct ccggccgaga actgattcat   5580
ttgttgcggt gatatgtaca tgtgcagggg gtggtgttga tgggtatcat tttgaggcct   5640
gaggatattg agcctttcgc cgatattcct cgagagaagc ttgaggcgat gattgccgat   5700
gtggaggctg tggctgtcag tgtcgccccc tgtatcgcta aaccggattt caaatacaag   5760
gatgccgcta aggctattct gcgcagggct tgttgcgct ggaatgatac tggcgtgtcg   5820
ggtcaggtgc agtatgagtc tgcgggtcct ttcgctcaga ctacacggtc taatactccc   5880
acgaatttgt tgtggccttc tgagattgcc gcgttgaaga agttgtgtga gggtgatggt   5940
ggggctggta aggcgttcac tattacaccg accatgagga gtagtgtgaa tcattctgag   6000
gtgtgttcca cggtgtgggg tggcggctgt tcgtgcggtt ctgatattaa cggctgcgat   6060
ggtcctttgt gggagatatg atatgactcg ttttccttat ggtgaaacgg ttgtgatgct   6120
tcagccgact gttcgtgtcg atgatcttgg cgacaaggtg gaagactggt ctaagcctgt   6180
cgagactgtg ttacataacg tggccatcta tgcttccgtt tcgcaggagg atgaggccgc   6240
ggggcgtgac tctgactatg agcattggac actgcttttc aagcagcctg ttgaagctgc   6300
cggttatcgt tgccggtggc gtatccgggg tgttgtgtgg gaggctgacg ggtctcctat   6360
ggtgtggcat catccgatgt ctggctggga tgctggtacg caggttaatg tgaagcgcaa   6420
gaagggctga tagattgtgg ctcaggatgt gaatgtgaag ctgaacttgc cgggtattcg   6480
tgaggtgttg aagtcttctg gggtgcaggc tatgttggct gagcgtggcg agcgtgtcaa   6540
gcgtgcggcc tcgcgaatg tgggcggtaa tgctttcgat aaggcccaat accgtaatgg   6600
tttgtcgtcg gaggtgcagg ttcaccgtgt tgaggctgtc gctcgtatag gcaccacata   6660
taagggtggg aagcgtattg aggcgaagca tggtacgttg gctcgttcga ttggggctgc   6720
gtcgtgatcg tctacgatga ccccaggaag tgggctaaac gcgtgctcaa ggatgatggc   6780
tggctgtctg atataccctg tgtggggacg gtgcccgatg attttacggg tgacctgatt   6840
tggttggcgt tggatggtgg cccgcagttg catgtgcgtg agcgtgtttt tttgcgcgtg   6900
aatgtgtttt ctgatacgcc tgatcggct atgtctttgg cgcgtcgtgt tgaggctgtt   6960
ctggctgacg gggttgatgg tgatccggtg gtgtactgta aacggtctac tggtcctgat   7020
ttgctggttg atggtgcacg tttttgatgtg tattcgctgt tcgagctgat atgtaggcct   7080
gcggagtctg agtaagctta ttgtttttgt tttaatgtaa ttgtttgata tttaatgggg   7140
gttgtgatgg ctgcaacacg taaagcgtct aatgttcgct ctgctgttac gggtgacgtt   7200
tatattggta aagctcatgc cggtgatact attgatggtg tgaaaacggt tcctgatggg   7260
ctgactgctt taggatattt gtcggatgac gggtttaaga ttaagcctga gcgtaaaacg   7320
gatgatttga aggcttggca gaatgcggat gttgttcgca cggttgctac cgagtcgtct   7380
atcgagattt cttttccagtt gatcgagtct aagaaggagg ttattgagct gttttggcag   7440
tcgaaggtta ctgctggatc cgattcgggt tcgttcgata tttctccggg tgccacgacg   7500
```

```
ggtgttcacg ccctgttgat ggatattgtg gatggcgatc aggttattcg ctactatttc   7560
cctgaggttg agttgatcga tcgtgacgag attaagggta agaatggcga agtgtacggg   7620
tatggtgtga cgttgaaggc gtatcctgcc cagattaata ataagggtga tgcggtgtcg   7680 ggtcggggt ggatgacggc tttaaaagct gatactcctc cggttccgcc ttctccgaag    7740
cctcagccgg atcctaatcc tccgtccgag aactgataca cgattttagg gattgttgat   7800
agatgagtga cacaggttac acgttgaaga ttggtgaccg tagctgggtg ttggcggatg   7860
cggaggagac ggctcaagct gtgcctgccc gcgtgtttcg ccgtgcagct aagattgccc   7920
agtcggggga gtctgcggat ttcgcccagg ttgaggtgat gttttctatg ttggaggctg   7980
ccgccccggc tgacgctgtg gaggccctgg aggggcttcc tatggttcgt gttgccgaga   8040
ttttccgtca gtggatggaa tacaagcctg accagaaagc ggcctccttg ggggaatagt   8100
ttggctccac ggcctgattg atgattatcg tggggccatc gaatatgatt ggaggacccg   8160
gttcggttgc tcgtttatg atgttggtgg cccgcagatg tgttggggtg aggctgtccg    8220
gctggctggc gtgttgtgta ccgatacgtc tagccagctg gcggcccacc tgaatggttg   8280
gcagcgtccg tttgagtggt gcgagtgggc ggtgttggac atgctggatc attacaggtc   8340
tgctaatagt gaggggcagc cggagcctgt ggcgaggccg acggatgagc gtagggcccg   8400
gtttacgtct gggcaggtgg acgatatttt ggcgcgtgtt cgtgccggtg gcggggtgtc   8460
tcgcgagatt aatattatgg ggtgaatagt gtatgtctgg tgagattgct ccgcatatg    8520 tgtcgttgta tacgaagatg ccgggtttga aggcggatgt tggtaaacag ctttctgggg   8580
tgatgcctgc ggagggtcag cgttcgggta gcttgtttgc taagggcatg aagttggcgc   8640
ttggtggtgc cgcaatggtg ggtgccatca atgttgctaa gaagggcctc aagtctatct   8700
atgatgtgac tattggtggc ggtattgctc gcgctatggc tattgatgag gcgcaggcta   8760
aactgactgg tttgggtcat acgtcttctg acacgtcttc gattatgaat tcggctattg   8820
aggctgtgac tggtacgtcg tatgcgttgg gtgatgcggc ttctactgcg gcggcgttgt   8880
ctgcttcggg tgtgaagtct ggcgggcaga tgacggatgt gttgaagact gtcgccgatg   8940
tgtcttatat ttcgggtaag tcgtttcagg atacgggcgc tattttttacg tctgtgatgg   9000 ctcgcggtaa gttgcagggc gatgacatgt tgcagcttac tatggcgggt gttcctgtgc   9060
tgtctttgct tgctaggcag acgggtaaaa cgtctgctga ggtgtcgcag atggtgtcga   9120
aggggcagat tgattttgcc acgtttgcgg ctgcgatgaa gcttggcatg ggtggtgctg   9180
cgcaggcgtc tggtcagacg tttgagggcg ctatgaagaa tgttaagggc gccctggatt   9240
atcttggtgc tacggctatg gcgccgtttc ttaacgggtt gcggcagatt tttgttgcgt   9300
tgaatccggt tatcaagtcg gtgacggatt ctgtgaagcc gatgtttgct accgtcgatg   9360
ctggtattca gctatgatg ccgtctattt tggcgtggat taaccgtatg ccggctatga    9420
tcactcgaat gaatgcacag atgcgcgcca aagtggagca gttgaagggc attttttcga   9480
gaatgcattt acctgtccct aaagtgaatt tgggtgccat gtttgctggc ggcaccgcag   9540
tgtttggtat tgttgctgcg ggtgtgggga agcttgttgc agggtttgcc ccgttggcgg   9600
tgtcgttgaa gaatctactg ccgtcgtttg gtgctttgaa gggtgccgcc ggcgggcttg   9660
gcggcgtgtt tcgcgccctg ggtggccctg ttggtattgt gatcggcttg tttgctgcca   9720
tgtttgctac gaacgcccag ttccgtgccg ctgttatgca gcttgtggct gtggttggcc   9780
aggcgttggg ccagattatg gccgctattc agccgctgtt tggtttggtt gctgggctgg   9840
tggcccagtt ggcgccagtg tttgcccaga ttatcggtat ggttgccggt ttggctgccc   9900
```

```
agttggtgcc tttgattagt atgcttgtcg cccggctagt tcctgtgatc acgcagacta   9960
ttggtgcggt gacgcaggtt gctgccatgt tgttgcctgc gcttatgccg gttattcagg  10020
ctgttgtggc tgtgatacgg caggttgttg gcgtgatcat gcagtggtg cctgttttga  10080
tgcctgtgat tcaacagatt ttgggtgcgg tcatgtctgt gctgccgcct atcatcggcc  10140
tgatccggtc gctgatacca gtcatcatgt cgattatgcg tgtggtgatg caggttgttg  10200
gtgtcgtgct acaggtggtg gcccgcatta ttccggttgt gatgccaatt gtgacagctg  10260
tgatcgggtt tgttgcacgt attcttggcg ctattgtgtc tgctgcagcc cgcattattg  10320
ggactgtcac ccgtgtcatc tcatgggttg tgaatcattt agtgtctggc gtgaggtcta  10380
tgggtacggc catcttgaat ggctggaatc atattagagc gtttacgtct gcgtttatta  10440
acggtttcaa gtcggtgatt tctggcggcg tgaacgctgt tgtggggttt tttgcccggc  10500
tgggttcttc ggttgcttct catgtgaggt ctggttttaa cgcggctcgt ggcgctgttt  10560
cttctgcgat gaatgctatt cggagtgttg tgtcttcggt ggcgtctgct gttggcgggt  10620
ttttcagttc gatggcgtct agggttcgta gtggtgctgt gcgcgggttt aatggtgccc  10680
ggagtgcggc ttcttctgct atgcatgcta tgggttctgc ggtgtctagt ggtgtgcatg  10740
gtgtgctggg ttttttccgg aatttgcctg gcaatattcg gcgtgcgctt ggtaatatgg  10800
ggtccctgtt ggtgtctgct ggccgtgatg tggtgtctgg tttgggtaat ggtatccgga  10860
atgctatgag tggcctgttg gatacggtgc gtaatatggg ttctcaggtt gcgaatgcgg  10920
cgaagtcggt gttgggtatt cattccccgt cgagggtgtt tcgtgaccag gttggccggc  10980
aggttgttgc cggtttggct gagggtatta ctggtaatgc tggtttggcg ttggatgcga  11040
tgtctgatat ggcgggacgg ctgcctgatg cggttgatgc ccggtttggt gtgcgatcgt  11100
ctgtgggctc gtttaccccg tatggcaggt atcagcgtgc gaatgataag agtgttgtgg  11160
tgaatgtgaa tggacccacg tatggtgatc ctaacgagtt tgcgaagcgg attgagcggc  11220
agcagcgtga cgctttgaat gcgttggctt acgcgtgatt gggggtgttg ttcatgtttc  11280
ttcctgaccc gtctgatcgt tctggtttga ctgtgacgtg gttgatggat ccgctgtttg  11340
gtggggagcg tgtgcttcat ttgacggatt atacgggtgc gtctcctgtc atgttgttga  11400
atgattcgtt gcgcggtttg ggtgttcccg aggtggagca ttttctcaa actcatgttg  11460
gggtgcacgg ctcggagtgg cgcgggttta atgtgaagcc tcgcgaggtg acgctgcctg  11520
tgttggtgtc gggtgttgac ccggatccgg atggcgggtt tcgtgacggt tttttgaaag  11580
cctatgacga gttgtggtct gcgtttcccc cgggggagga gggcgagttg tcggtgaaga  11640
ctcctgccgg ccgtgagcgt gtgctaaaat gcaggtttga ttcggtggat gacacgttta  11700
ctgttgatcc ggtgaatcgc ggctatgccc gctatgtgat tcatttgaca gcttatgacc  11760
cgttttggta tggggatgag caaaagtttc gttttagtaa cgcgaagttg caggattggt  11820
tgggtggcgg ccctgtcggc aaggatggta ccgcgtttcc tgtggtgttg acgcctggtg  11880
ttggttcggg ttgggataat ctgtctaata agggtgatgt gcctgcgtgg cctgtgattc  11940
gtgttgaggg cccgttagag tcgtggtctg tgcagattga tggtttgcgt gtgtcttcgg  12000
attatcctgt cgaggagtat gattggatca ctattgatac ggatcctcgt aaacagtctg  12060
cgttgttgaa tgggtttgag gatgtgatgg atcgtttgaa ggagtgggag tttgcgccta  12120
tcccgcctgg cggttctaag agtgtgaata ttgagatggt gggtttgggt gccattgttg  12180
tgtcggtgca gtacaggttt ttgagggctt ggtgaatagt tgatggctgg tcttgttccg  12240
```

```
catgtaacat tgtttacgcc ggattatcgt cgtgtggcgc ctatcaatttt ttttgagtcg    12300
ttgaagttgt cgttgaagtg gaatggtttg tctacgctgg agttggtggt gtcgggggat    12360
cattcaaggc ttgacgggtt gactaagccg ggtgcacggc tggttgttga ttatggtggt    12420
ggccagattt tttctgggcc tgtgcgtaag gttcatggtg tgggtccttg gcgttcttcg    12480
cgggtgacta tcacgtgtga ggatgatatt cgcctgttgt ggcgtatgct gatgtggcct    12540
gtgaattatc gtcctggttt ggtcggtatg gagtggcgtg ccgacaggga ttatgcccac    12600
tattcgggtg cggcggagtc ggttgctaag caggtgttgg gggataatgc ttggcgtttt    12660
ccgcctggtt tgtttatgac cgatgatgag agtcgtggcc gctatattaa ggattttcag    12720
gtgcggtttc acgtgtttgc cgataaattg ttgccggtgt tgtcgtgggc tcggatgact    12780
gtcacggtga accagtttga gaatgcgaag tttgatcagc gtggtttagt gtttgattgc    12840
gtgcctgctg tgacgcgtag tcacgtgttg actgccgagt ctggttcgat tgtgtcgtgg    12900
gagtatgtgc gtgacgcccc gaaggcgaca tctgtggtgg ttggtggccg cggcgagggc    12960
aaggatcggc tgttttgcga ggatgttgat tcgatggccg aggggattg gtttgatcgt     13020
gtcgaggtgt ttaaggatgc ccgtaacacg gattctgagc atgtgcatct cattgatgag    13080
gctgagcagg tgctgtccga gttaggggct acttcggggt ttaagatcga gttggctgag    13140
tcggatgtgt tgcggtttgg gccaggcaat ctgatgccgg tgatttgat ctatgtggat      13200
gtgggttctg ggcctattgc ggaaattgtt cggcagattg atgtggagtg tgtatcgcct    13260
ggtgatggtt ggacaaaggt gacaccggtt gcgggtgatt atgaggataa tccgtcggcc    13320
ctgttggctc gccgtgttgc cggtttggct gcgggtgtgc gggatttgca aaagttttag   13380
taagtgattg gggtttgttg tgggtattgt gtgtaaaggg tttgatggtg tgttgaccga    13440
gtatgattgg gctcaaatgt ctggtctgat gggtaatatg ccgtctgtga aaggggcagga   13500
cgattttcgt gtcggcacta cggttcaggg tgccacagtg ttgtgtgagg tgttgcctgg    13560
gcaggcttgg gctcacgggg tgatgtgcac gtcgaatagt gttgagacgg tgacggggca    13620
gctgcctggt tctggcgaga cccgctacga ctatgtggtg ttgtctcggg attgggagca    13680
gaacacagcc aggttggaga ttgttcctgg ggggcgtgcg gagcgtgccc gtgacgtgtt    13740
aagggctgag cctggcgtgt ttcatcagca gttgttggct actttggtgg tgtcgtctaa    13800
cgggttgcag cagcagttgg ataggcgtgc tatagcggcc cgtgtggcgt ttggggagtc    13860
tgctgcgtgt gatcctaccc ctgtggaggg tgaccgggtg atggttcctt ctggtgctgt    13920
gtgggctaat catgcgggcg agtggatgtt gttgtctccg cgtatcgaga cgggttctaa    13980
gtcgatcatg tttggcggat ctgctgtgta tgcttacacg attccgtttg atcgccagtt    14040
tagtagtccg cctgttgtgg tggcgtctat ggctacggcg gctgggggta cgcagcagat    14100
cgatgtgaaa gcctacaata ttactaataa ggatttttat ttagcgttta ttacgaatga    14160
tagttcgaag ccttctggtg tgcctgcggt ggctaactgg attgctgtcg gcgtgtaatg    14220
tgcggcctgc aggtatgtga cgtgttgtgg tggttgtagt ggtagggggc tgtagtgtca    14280
tggtttacac ctgcactggt ggcctctatc tgtaccgcgt tggccacggt tttgggttct    14340
gttcaggcgg tcacgtctaa atctcggagg cgtttgcggc ggctgtcggc tcaggtggat    14400
gcgatggaag agtatacgtg gggtgtgcgg cgcgaggtgc gaaggtttaa cgccgggctt    14460
cctgatgatg tggagcctat gcatctccct gatgtgcccg agtttttgaa agatactgtt    14520
gatggtggag gtgagtaggg ttgagggagt tggaggagga gaagcggcag cgccgcaatt    14580
ttgagaaggc ttcactggtg ttgttgtttt tgtcgcttgt gttgttggcg gtggttgctg    14640
```

```
cgggtgctttgcgtttcggtgctgtatcctctgagcgggattcggagcaggctagggccc      14700
agtcgaatggtacagcggctcggggtttagccagccgtgtgaagtgggtgtgtgcttcgg      14760
gtggggtggagtctgcgcggcttcaccgttctggtttgtgtgtggatgctgtgcgtgttg      14820
agcagcgtgttcagggtgtgccgggcccggctggtgagcgcggcccgcaaggccctgcag      14880
gtgctgacggccgggatggtgttaatggttcggctgggctggtgggccctgttggtccgc      14940
agggctctcccggtttgaatggtgtgaaaggtcctgacggttgcctggcgcgaatggat      15000
cggatggccatgatggtgttccaggtcgtgcaggtgctgacggtgtgaacggggttgacg      15060
gcgctgatggtcgggatggtgttaatggttcggctggtgagcgcggtgatgtgggcccttt    15120
caggtcctgccggccctcaaggtgcacagggtgaacggggtcctgctggccctgttggtc     15180
cgcagggttctgccggtgccgatggcacgaatggtaaagacggtaaggatgggcgctcgg     15240
tggtgtctgtgtactgttccgggggtcgcctggttgtgaaatatggtgacggtgtggctt    15300
ctaccatatcgggttcggtagcctgcgagagtgtgaaaccgtcacctatagtgactatat    15360
catcccacaaatagaaaggagtggctgtgatggtagtgttggtggtgacatgtgtgag     15420
gtttattcctgctgcgcatcactcggccggttcgaatagtccggtgaaccgggttgtgat    15480
tcatgcaacatgcccggatgtggggttttccgtccgcttcgcgtaaaggacgggcggtgtc    15540
tacagcgaactatttcgcgtccccatcgtcgggcggttcggcgcattacgtttgcgatat    15600
tggggagacggtgcagtgcctgtcagagggactattgggtggcatgcccgccgaatcc    15660
gcatagtttggtatagagatttgcgcggatgggggttcgcacgcctcgttccgtgtgcc    15720
ggggcatgctacacgagggagcagtggctgatcctcgcgtgtggcctgcggtggagcg     15780
tgccgccatcctgtgtagacgtttgtgtgacaaatataatgttccaaagaggaagcttag     15840
tgcagccgatttgaaggctgcaggcggggtgtgtgtggccatgtggatgttacggatgc      15900
atggcaccagtcggatcacgatgatccgggccgtggtttccgtgggacaggtttatggc      15960
cgtcgtgaacggcggcagtgagagagtgaggagttaacggtggctgatgtacaagcgtt     16020
acataatcagattaaacaattgtctgcccagcttactggtcggtgaataagctgcacca     16080
tgatgttggtgtggtgcaggtgcagaatggtgatttgggtaaacgtgtggatgccctgtc     16140
gtgggtgaagaacccggtgacggggaagctgtggcgtactaaggatgctttgtggagtgt     16200
ctggtattacgtgctggagtgtcgcagccgaatagacaggctcgagtctactgttaacgg     16260
tttgaaaaagtgatggtggtttgttgtgggtaaacagttttggttgggcctgctggagcg     16320
tgccctgaaaacttttattcaaacgtttgttgctgtgttgggtgtgacggcgggtgtcac     16380
gtatactgcggagtcgtttcgcggtttgccgtggagtctgccctgataacagccacggt     16440
tgctgcaatactgtcgattgctacatcgtttggtaatccgtcgtttgtggccggcaagtc     16500
gaaggtgacgcctgttgatgctgggcttgtccacccgccgatacgggcatggttgagcc     16560
gcacatggttgatgtgttggatcctggcatgatcgagccgatggatgatgctgatcttgg    16620
tggctatgtgccgaggcgtgccgccgagtcggaggttggcacggtagagtctactgttgc     16680
ataattgaatatgtgtgtgcccagcggtgctgccacgatcgtgtggtggttgccgctgg     16740
ggcacaatttttgtgttctacagtattctatgattcgttgttgtctatagtttcttcgag    16800
catctgatacaggtggaggcaggcggagatagtatcgttggcctggtctagaacgttctg    16860
gccgataacattttgtggttgtcgcggtgcagatgatagaccgcatgatatcgtcggc     16920
cgccgattgcagtagtttggtttggtatgcgattccggcgagccaatctatggcttcctg    16980
```

-continued

```
gcttgcccgt gtgtcgtctg gcatgccacg ggtgttgctg ttgtttgtgg ggtatcctgc    17040
actgtcgcag taccacaaga tttcgctgca ctcgtctagc gtgtcctggt cgatagccag    17100
atcgtcgagg ctgacttctt tgacggtaag gttcacgttg tcgagtgaga ttggtacacg    17160
gtactggttt tcgacaccgc caacaatgtt ttctagctgt tgcatgttgg tgggctgttg    17220
ttggatgatt cggtgtaccg ctgttttgag ggcagtgtag ggggtatttt gtgtgttgtt    17280
catggtttta tcccatccct gtgctgtcgt cgttgccgtc tggatagtat ctactgtttg    17340
cgtagcctgt tagggtgatg agtgtttggt ctgcccactg tttcactgtt tgtcttgtca    17400
ccccgagtcg ttgggctgcc accgaatagg tttgatcata cccgtatact tccctgaatg    17460
cggcaagccg tgctagccgt tttcgctgtt tggatggctg gcaggtgagg gtgtagtcgt    17520
cgatggccag ttgtagatcg atcatggaga cgatgttgtt gccgtggtgt tgtggcgcgg    17580
ttggtggggg tggcatgccc ggctctacac tcggtttcca tggtccgccg ttccagatcc    17640
attgggcggg ttgatgatg tcggcggtgg tgtaggtttg gttcactggt cacccctgta    17700
acaggttgtc gaggttgtct gggttgctgg tgttagtggt gtcgaatcgt ccgacgcagt    17760
ggcagtagtc gtacatgagt ttgataatgt gttggtggtc tcccaaatag gtgttgccgc    17820
tgatgctgta ggtggctgtg ccgtctttac taataatgta ttttgcggtg atggtttcgg    17880
gtgtttcggt gttggtgatg atggctgtgg tggtggcgcc tacggtttgt agcctggtgg    17940
tttgggttcc gtcgtcgagg atggtagtaa ccatgagggt tgtcctttag atgctggttt    18000
ggttgtcgga tagatgaata atatcggata aaggtttcgg ctggtctagg tgttgtatgg    18060
ttttgttggc tagccgtttg gctaccctgt aacacatttt ggtatagtgt ttgttgtcta    18120
ggttgtggta ttgttcccgc accgcaatat atagtaggga gtcttggtac aggtcgtctg    18180
cactgattgc ggggtagtgt ccggctgttt tggtgcatgc ccggttgagt gtgcggagat    18240
gatggcctgt ggcccatccc cacgatgcgg tggcggccag gtcggctttt gttggtcgtc    18300
tactcatggc actatttcat ctcgctatct ggtagttgtt tggtgttttg ttgttgatag    18360
tgtagcacac gagtccgggg tggcggtgg tgcctgtgcg gtgccggaac catgtggatt    18420
cgccttccat ggatgggcat tggatgaagg tgcgttgtcc ttgctcggag atttcgaggt    18480
ggtgccggtg cccggccatc agaatattag atacggtgcc gttgtggaat tcttggccgc    18540
gccaccattc gtagtgttgg ttgttgcgcc attggtgtcc gtgggcgtgc aggatttgtg    18600
tgccggccac attgacggtg gtggtcattt cgtccctgtc agggaagtgg aagtgtaggt    18660
tggggtagtt gttggtgagc tggtaggctt ctgcgatggc gcggcagcag tccacgtcga    18720
aggagtcgtc gtaggtggtg acgcctttac cgaatcttac ggcttcgccg tggttgccgg    18780
ggatggatgt gactgtcaca ttttggcagt ggtcgaatat gtggactaac tggagcatgg    18840
ccatgcgggt gagcctgatt tgttccgtca agggtgtttg ggtgcgccag gcgttgttgc    18900
cgccttgtga cacgtatcct tcgatcatgt cgccaaggaa tgcgatgtgg actcgttgcg    18960
gctgtcctgc ttgccaccag tagtgtttgg cggatgtgag ggagtgcaaa tagtcgtcgg    19020
cgaagtgtgc tgtttctcct ccggggatgc ctttgccgat ttggaagtct cctgccccga    19080
tgacgaaggc tgcagtgctg tagtcggtgt gggtgtcttg ttcgggtttt ggtggctgcc    19140
attcggctag tttatcgacg agttcgtcta caggtaggg gtcggttgta ggctggtggt    19200
cgatgatttt ttgtatggat cggccggttt ctccgttcgg taaggtccat tcggagatgc    19260
gtgtgcggcg cacggtgccg ttggctatgt tgtcgtcgat ggtgtcgatg gcgttgtcgt    19320
ggttggctag ctgggtgagg agccggtcta tgttgtctat catcgggtat cctcctcttg    19380
```

```
ttgctgggtg gtgttggctt gtttgcggcg atagtctttg atgacggtgg cggagatggg    19440
gtatcctgcc tgggtgagtt gttttgctag ccatgaggcg gggatggttt tgtcggcgag    19500
gacatctgcg gctttgttgc cgtagcgttg aatgagtgtt tcagttttgg ttgccatgat    19560
gtcctagggg ttgtgtggtg ggctgccatc ctgtgcggca gtcgccgtcg tgtcctggtt    19620
tgcgtgtgca ccacgatacg gttccgtctg tgtggttgag tgttttgccg cacatgatgt    19680
cacgtaggtg ctcgggaaac ttatcgttgt tgttgtcccc gtgcgtgtcg atcaagtgtt    19740
gggttttggc gaccatcatg tttcctatgt gtgaaagagt gtgcaaatac tatgcaggtg    19800
tcatgggtgt ttatgcgggt atggttttca tcaccttgct gaacgtcacc tggttactgt    19860
acatcatctg ggtgatttcc tgatccgttt tgtcggggtg ctgctttcgc aggttcgccc    19920
actggcaggc gttgtcggtt tcctgctgta aacgtgtcag gtgctgctct gcgatgatgt    19980
gtttccacat ggtccatgat atgtcgagcc gtttgagcat gtcgatggct ggcacgttga    20040
acgagttgag gaagagtatt tcttcggtgt agtactgttt ttcgtattgg tcccatccgc    20100
ttcggtgcct gttgggctgg ttttgggt aggcttcccg gcagattttg tgtaaccgtt    20160
tggccatgtc gtcgggtagc ttgatgtcgg ggttggcgcg gatcatggat cgcatcccgt    20220
cgtaggtggt gccccaggtg tgcatgatgt ggagtgggtc ttcaccatca gcccattttt    20280
ctgcacagat ggcgaggcgg atgcgcctcc tggcggcctt agaggtgtcg ctgcggccgg    20340
ggatggggca ggtgtcgagg ggatccatga tgctttagtg tacctttctt ggtttcgtgt    20400
tgttgtctgg ttttattgta gcactgtgtt gagtgcttgt gtcaaccctg ttttgccggt    20460
tttcaggtag gtgtctgtga catccccgac agtgaggggc acgtgggtgg cttggggag    20520 tgctacctgg agggtttggg ccatctggtc tcccgctttg tctgggtcgg accagatgta    20580
gatgtggtcg tagccttcga agaatttggt ccagaaggtt tgccacgagg tggcgccggg    20640
tagtgctacg gccgaccatc cgcattgttc gaggatcatg gagtcgaatt cgccttcgca    20700
aatgtgcatt tcggctgccg ggtttgctag ggcggccatg ttgtagatgg agcctgtgtc    20760
tcctgccggg gttaggtatt tggggtggtt gtgggttttg cagtcgtgcg ggagtgagca    20820
gcggaaacgc attttcgta tttctgctgg cccttcccat gtggggtaca tgtaggggat    20880
ggtgatgcac tggttgtagt tttcgtggcc gggtatgggg tcattgtcga tgtatccaag    20940
gtggtggtag cgggctgttt cttcgctgat gcctcttgct gagagcaggt cgagtatgtt    21000
ttcgaggtgg gtttcgtaga gggctgaggc tttctggatt cggcggcgtt ccgcaatgtt    21060
gtatgggcgt atgctgtcgt acattcgggt tttctttctc taatcgttgt tgtagcttgg    21120
cgagtccgcc tccgacaccg catgtgtggc agtaccagac gcccttgtcg aggttgatgc    21180
tcatggaggg ctggtggtcg tcgtggaacg ggcagaggat gtgttgctcg ttcctggacg    21240
ggttgtaccg tatccggtag gtgtcgagga ggcggcaggt atcagaggtg tgggaggagc    21300
tcgttgaggg ttgataccac ataggcttcg ctccatggct tgttgcgctg tttcatcact    21360
acgagtccga tagtggactg gcttttctcgg ttgcggtgtg tttcgtagtt gcgtgcctcc    21420
cggctggctt gtttcacgaa ttgggctagg tgtggctggc cagctttcgc ctcgatcacg    21480
tatgtgtggt ttttggtttt gaggatgagg tcgccttcgt cttcgcggcc gttgaggtgg    21540
aggcgttcta tatcatgacc ggtgtcgcgt agctggtgga ggagtcgtgt ttcccattct    21600
gcgcctgccc tgcggttgcg tgcctgttgt gttggcatga tagtcctttg tgtgttgggg    21660
tcatgttcca tggctgtttt tcggcgaggg gtccgaagaa tgtgtattcg gggtaggctc    21720
```

```
gtagccgttc gtattgggtg ccgtcggggc tggatttgcc tgtgcgctgt ttcaacactg    21780
cgatgcgtgc ctctgccggg atcgataggc cgttgccgtt atcctcgcca ccatacaggg    21840
agactccgag gatgagttgt ggttttcgg agaggccgtt tttgatttct cgccgggcgg     21900
gcgggtgttc gatgtcggag ccggttttgt cggttgcgtg gtgtgtgaca ataatggtgg    21960
agtccgtgtc cctgcccaat gctgtgatcc attgcatggc ttcttgctgg gcctggtagt    22020
cactctcgca gtcttgtatg tccatcaggt tgtcgataac aatgagtggt ggaaaggtgt    22080
tccacatttc catgtaggct tgcagttcca tggtgatgtc tgtccatgtg atgggtgact    22140
ggaatgagaa tgtgatgtgc cgccgtggt ggatgctgtc tcgatagtat tctggcccgt     22200
agtcgtcgat gttttgttgt atctgtgcgg tggtgtgttg ggtgttgagt gagatgattc    22260
gtgtggaggc ctcccagggt gtcatgtccc ctgatatgta gagggcgggc tggttgagca    22320
tcgctgtgat gaacatggct agcccggatt tttggctgcc ggagcgcccc gcaatcatga    22380
cgagatcccc tttgtggatg tgcatgtcca ggttgcggta gaggggttct agttgtggta    22440
tgcggggcag ctcggctgcg gtttgggagg ctctctcgaa ggatcgttgt agagagagca    22500
tcggagcctt aatctatctg tttgttggat gtgtattggt ggtcagatgg agtcgatgtc    22560
tacatcatca ctaccagtgg tgttgggctg gctgtctcgc cggtcaacgt aggctgctac    22620
gaggtcgtag atggcgtcgt cgaggggttt gagcacgacc gcgttgaagc cgttttggt    22680
gcgcacggtg gctagtttga aggcctgctc ctcgccaagg tatgcttcta ggtcgcggat    22740
catggagtgt gggcggtcgt tgttgccgcg tgctttctca ataatagcgt tggggatggt    22800
ttctggggtg ccgttgttga gatcgtctag ggtgtggaag atggtgacat cagcgtagat    22860
gcgatcggcg gtctgtccgc cgtagccttc ggtgttgtgc tggacgtcgt ggactttgaa    22920
ggcgatggcg gtggcgtcct ggtttcggga ggggttgaag aaggtgctgt tgctgttgtt    22980
gcggtagttg gcgagtccca ttgttgtttc ctttactgtt tgtgttgttt tgtttgtcgg    23040
ttttatcggg tgaggctgtt tcgtttcgtg cggaaggctt cggatacgtc actgttactg    23100
gtgatggtct ttttgtactg tttgagaagg tcggctagct gtgctttgct tgtggcattg    23160
ttgattttgt cgatgatggt gttgtttcct tctgatgcga tgttgtctac gtagtctttg    23220
gcggctggt tgtatcggtc ttggaggatg atggatgctg tggcgatcag tgttgccagg    23280
tcccagttcc ttgccgccga actgttttg agtccgccta acaggtcgat gatagtcttc    23340
ttcacctggt cggcggtgtc tcccctaatg acggtccatg gggcggcgta gtctccgccg    23400
tatttgaggg tgacggtgaa tcggtcgtcg tctgtgttgt cggtcactgg tgctccttgc    23460
cttcttctgt tggggctgtg atggtggttt ctatagggta cctgtaggcg tctttcccgt    23520
ctacagccca acaggcgtcc ttgacggggc atcctttaca gagtgctgtg acgtgggta    23580
cgaagatgcc ttcgctgatt cctttcattg cttgactata catggatgat acatgccggt    23640
aggtgttgtt gtcaaggtcg tacagttcgg tggatgtgcc ttgtgtcggg gacttgtcgt    23700
cgttgcggct ggtggctggc gtccaaaaca tgcctttcgt gacatggatg tcgtgttggt    23760
tgagcatgta ccggtaggtg tgcagctgca tgctgtcggc gggtaggcgt ccggttttga   23820
ggtcgaggat gaaggtttcg ccggtgtcgg tgttggtgaa gattcggtcg atgtagccga    23880
cgatctgggc gccgtcgggg agggtggttt ctaccgggta ttcgatgcct ggctggccgt    23940
ccagaattgc ggtgatgtat tctgggtggt tgcgcctcca gttttccac cggtccacaa     24000
aggtgggggcc gtaaaccatc caccaattgt agtcttttt gtgtgccccg cctgactcgc    24060
acatgttttt gcatattctg ccggagggtt tgatttctgt gccttcggat tcggcgaggg    24120
```

-continued

```
cgatttgggt gtcgaaaatg ttttttgaagg atgagagttt gtcgggcagt gcagggtatt   24180
cggcgggatt gtacaggtgt aggtcgtatt gttcggtgat gtggtgtatg gcgcttccgg   24240
cgatggtggc ataccaggtg tggtgttggg catggtagcc gtgttggagg cgccattttt   24300
ctccgcattc ggcccactgg gtgagtgaac tgtaggagat gtggcctgga tggttgatgg   24360
ttttcgggta ttgtgctagg ggcattactt gtcgcttttg ttccatgggt tgcgggtgtc   24420
ttggccggcg tggtgttgct ggtatgcgag gagtgcgagg cagtgccagg cggcgtgtgc   24480
cagatgcggc aaatgtgatt cgtggtcgag gttgttgcct tgctgccatg atagtaggtg   24540
cctgtagagg gcgtcgacac tgtggctcca cgggtatcct ccggtccagt tgttgtcgcc   24600
gtatttggtg gcgccgtagc ctgctacttc gcctagggcg tgaagggatg ctgggtcgat   24660
gagggatagc ctgcattgtt tgagttcttt tcgggcaccg ctgttcgggt cggtgtacat   24720
gcgggtgggc tcatccatgg ggtgtgtgct ccttaagggt gggttactgg ttgttatcgt   24780
gggctagggc gacggcgaga ataatgatgg cgagggtttc tgcgatcagt atgggtgttg   24840
tgatcattta gtgtctcggg gattgttggt gagggttgag gcgcctagga gggtggcgag   24900
ggcgcatgcg gcgatgatgg cgagggctgc cttgtgtggg gtgccggtgg cgtacatcca   24960
tgtgatgatg ccgccttgga tccaggctag gctggtgaag aacgtttcgt aactgtgcag   25020
ctcaatgttg ttgttgggtg tgttcatgct tgctcctgaa gaatggtgtt gatggtttta   25080
taaatgttgt acaggtcggt ttcgatagat aacagttggt tgatttggtg gtcgagatca   25140
atgtctgggt tgagggtgtt gatgcgggag gcgatatcgg tggctgtgcg tagtgtgccg   25200
ccggtgtggt gaatgatgtg tgccgtgtcg gctagtccgg tggtgacggc gtagtgggag   25260
aggagaggca tagcagggat gctccttgac gggttactgt tgcgggttga tgttgaggtc   25320
ggtgacgtgc gggtggtctt ctgttccggt gacgaggcag tggacggtga ctgggagttt   25380
ggatgcgccg ggctgtttca tggttgcacc gtagacgatg gagaaggtgt ctttaccgat   25440
ggttttgtgg agttggaggt cgatgtcggg gttgccgttc cagttgacac cgtgtgcggc   25500
ggcctgttgt tcggctttgc ggttgcaggt gtgtgccgcg gtgatcatgg tgagtccggt   25560
ggcggtttct tcaccccgtg tttgggcttg cttgtgggtt ttggtctgct cggcttgtag   25620
ggagcgggtg gcggctgcct gacgtgccgc tttctcggct ttgcgctgtt ggacggtttt   25680
gggggtccat tcggtgttgg ctgttgtggc ctgtggggct ggctgtgagg cgagtggcgg   25740
attgtcgtct gggctggca tgaaggaggc tgcggcgatg atggcggctg tgatgcctgc   25800
gatggtgtag ccttctcttc tgttcatggc tgttgtcccc tttccggggt gttgttcgtt   25860
gctgacatga tcaatacttc cagtgactgg accgcgtgtc aaggctgcgc tcaacgattg   25920
tgagcgatcc ttgtgtggct aggggtttta tcgggcacac agggtgagta gatggccaac   25980
attgatgcgg ctcacattcc agtagagttg tgtggcttca ccgccggtga gcggcttcca   26040
ctcgtcgtgg ctgaacacgg tgccatcggt ggcgatgaat gtgtttgggc gtagtttgtg   26100
aagttcggct tccacgctct gccggtaggc ttcggcgagg ccttcaaaat ccatgtggtc   26160
gcagtggagg ttttcgaggc gtgtcaggtc gaagggtgtg gggcagtcgt agctggtggg   26220
ggtgtagagc tgggtgaagt ggttggcgat cttttgcatc atgattcctt ttctggtgat   26280
ggtgtgttga ggatttatcg ggtggatgcg acaaggatgg cgtctatgtc gatcatgtcg   26340
atgagatcgt ggagttcctc ggcttcattc tcggtgagcg gctgccagtc gtagtccccg   26400
tatagggcgc cgtcgagggt gacagtccac agtggccgga tgagtcgtat ggcttcttgt   26460
```

```
actttagcgt ggtacatgcg gcgcaccata tcgagatcga tgtcgtctga atggtttccg   26520
gtgaggctgt ggaggctgag cgggtctatt tctgtctgcc tgtagaggga tgtgaaggat   26580
ggggtgatga gtgtgccatc catgggtgat gttcctttct ggattgtctt ggttggttgt   26640
tgtggttttt atggtgtgag ggttgtgatc catagtcaag gctgcgctca ttcggtttga   26700
gcgtttcata tgggtgtggc atggggtgtg gcgtatctca cttaagcctt tatggcctct   26760
ctcggcgtct caaatcttct aggggtagga ttatataggg ttgaccctgc tgatcgattc   26820
tagggccctt ctagggcgtc tcagaggtat gtctgagtga tagcaggtcc ggtagatgac   26880
ccggcagatc tgccttggct ttcatcgcgg gggtcgaggt gccagatctg gcatggaat    26940 ctacaccctc ataccgtgtg agataggcca cactcgcctc gtatggtgtg caccccaag    27000 gccactctgc caatctggcg tggagggtgt agcccagaaa tgccgtttaa agcctcaggg   27060
atacgcctag gagcgccttg cggggtgggg gctaggtatt tataccccca gcacattctg   27120
atcgattcta gacgcccac agagcctgat acacgatcaa ccatcccagc atagatcacc    27180 agccctatc ctgcttagct aagcctcaac tatgtggaca gtgtgggata ctgtggggga   27240
agaaggacac ggtaaaaaga agggggggcat cagccttcac acctgaggta cttaagttaa  27300
ccttagggtc ttagcgctga gcatttagca ccgagcccct caagggctcg gcataagccc   27360
gagcaggctc agccgatcag gcacagccct gaaaggggta cacgccatca ggggaaggctt  27420 gagagtacga ggagccttag cgacgagtac tcgaaagcct gagggaacac cctcagcact   27480
gatgggccta gcgtgttcgg aaaggacaca agagtacagt gtgacagctg tccgggagtg   27540
aaacccgttc tgactagggg tttcagcctt aacaaccctc aaaggttaca agactctaag   27600
aaaatttaag gaaaagttta ggtttaatt ttggaccttc actaccaaaa acacccgttt    27660
acacccatca aacccgccta tagagccaaa tccaccagtt tgactcatcc caggtggggt   27720
atgataggct ggacaggtag ccagctggac gcaaggccga aatccgctga cgcggctttc   27780
acccttacat ccatcagtct accaaacact ttaaagcttc aagggcttag cgctaagcac   27840
cgagcccctc aagggctcgg catcagtctt aaagccttaa acacttaaag tacatataaa   27900
accttaacag ttaaacgtta aaagctttaa accttaacac ctaagttaag tataaaacct   27960
taaaggctta gcacttaagg atataaactt aacatcagtg tttaagactt taaaacttaa   28020
aataactatt aagactttaa aaaccttaag tacttaaagt taaccatcag tcttaaactt   28080 taatatttata acctataagt cttaaagctt ataggtatta tattataata taagtattaa   28140
agcttataag ttataaaagt tttagaagag ctaagaggtt aacttcttta cttctctact   28200
ctctttggta cttctctctc tctcttcttt tcttcatcag gggagaagag gaaccttta    28260 ccgtgtgact cgtgtgcttc tggtcgcaag ttcccatcgc acactcccca cactctgaca   28320
cccgtgtccc tttacggctt ggcgtgttcg gctgaaggcg tacggcgtgt cacgctcaca   28380
cccttaacac cagatgagac ttaaagtgta tattatatgt agaagacttt aaaacctat    28440 aaggtgttcc tgctgagcct gtgtccttta acgctaggcg ccaagcgcta agctgtgaaa   28500
cgcgaacaca cacccacccc cattttcttt ccgtgtcctt ctcttttgac acaaccgggg   28560
ggcgatgtga tcttttttcac atgccggggg gtatgagtag aaaacaaaca ccccggcaca  28620
aacagaaacc cccctcaaac aaacaaaaca gggcctagaa tcgatcggca gggcaaggggt  28680 agagtattta taccoctaga cgatcccaag cccttataga ggcaaataag acccgtacag   28740
ggctaggcga ggaacagaca catcatggca cgcaccaacc gcacagccag ccaagcccac   28800
cggcgctggc gggcaagact catcacccaa gcccgacaac aaggccaaac cgaatgccca   28860
```

```
ctctgcggag cccagatcgc ctggggcaca cacgatctac caaccagccc cgaagccgac    28920
cacatcacac ccgtcagccg cggggactc aacaccctcg acaacgggca atcatctgc     28980 agaacatgca acagaagcaa aggcaacaga acacaaccaa acatcaaatt ccaacaacaa    29040
accacaaaaa ccttgattcc atggtgaaaa acccgccaac ccccaccggg cacacccct     29100 gcacacccg                                                            29109
```

<210> SEQ ID NO 6
<211> LENGTH: 855
<212> TYPE: DNA
<213> ORGANISM: Bacteriophage 103609

<400> SEQUENCE: 6

```
gtgagataca ttcctgcggc gcatcattct gccggctcga atagtccggt gaatagggtt     60
gtgattcatg cgacgtgccc ggatgtgggg tttccgtctg cctcgcgtaa agggcgggcg    120
gtgtctacag caaactattt cgcgtcccca tcgtcgggtg gttcggcgca ttatgtttgc    180
gatattagtg agactgtgca gtgcttgtcg gagtctacga ttgggtggca tgccccgccg    240
aatccgcata gtttgggtat cgagatttgc gcggatgggg gttcgcacgc ctcgttccgg    300
gtgccggggc atgcttacac tcgggagcag tggcttgatc ctagggtgtg gcctgcggtg    360
gagaaggctg ccatcctgtg tagacgtttg tgtgacaaat ataatgttcc gaagaggaag    420
cttagtgcag ccgatttgaa ggctggtagg cggggtgtgt cggccatgt ggatgtgacg     480 gatgcgtggc atcagtcgga tcatgacgat ccggggccgt ggtttccgtg ggacaggttt    540
atggccgttg tcaacggcaa agatgagagt ggggagttaa ctgtggctga tgtgaaagcc    600
ttgcatgatc agattaaaca attgtctgct cagcttactg gttcggtgaa taagctgcac    660
catgatgttg gtgtggttca ggttcagaat ggtgatttgg gtaagcgtgt tgacgccttg    720
tcgtgggtga agaatccggt gacgggaag ctgtggcgca caaggatgc tttgtggagt      780 gtctggtatt acgtgctgga gtgtcgtagc cgtattgaca ggcttgagtc gactgtcaac    840
ggtttgaaaa agtga                                                     855
```

<210> SEQ ID NO 7
<211> LENGTH: 864
<212> TYPE: DNA
<213> ORGANISM: Baeriophage 103672

<400> SEQUENCE: 7

```
gtgaggttta ttcctgctgc gcatcattct gccggctcga atagtccggt gaatagggtt     60
gtgattcatg cgacatgccc ggatgtgggg tttccgtccg cttcccgtaa ggggcgggcg    120
gtgtctacgg cgaactattt cgcgtcccca tcggcgggcg ttctgccca ttatgtgtgc     180 gatatttcgg agacggtgca gtgcttgtcg gagtctacga ttgggtggca tgccccgccg    240
aatccgcata gtttgggtat cgagatttgc gcggatgggg gttcgcacgc ctcgttccgt    300
gtgccagggc atgcttacac gagggagcag tggctggatc ctagggtgtg gcctgcggtg    360
gagaaggctg ccatcctgtg tagacgtttg tgtgacaaat ataatgttcc gaaaaggaag    420
cttagtgcag ccgatttgaa ggctggcagg cggggtgttt cgggcatgt ggatgttacg     480 gatgcgtggc atcagtcgga tcatgacgat cctgggccgt ggtttccgtg ggacaaattt    540
atggctgtgg tgaatggcca cggcggcggt tcaagtagtg aggagttaac ggtggctgat    600
gtgaaagcgt tacataatca gattaaacaa ttgtctgctc agcttactgg ttcggtgaat    660
```

```
aagctgcatc acgatgttgg tgtggttcag gtgcagaatg gtgacctggc gcgccgtgtt    720
gatgccttgt cgtgggtgaa gaatccggtg acggggaagc tgtggcgcac taaggatgcc    780
ctgtggagtg tctggtatta cgtgctggag tgtcgtagcc gtattgacag gcttgagtct    840
gctgttaacg gtttgaaaaa gtga                                           864

<210> SEQ ID NO 8
<211> LENGTH: 858
<212> TYPE: DNA
<213> ORGANISM: Bacteriophage 1894

<400> SEQUENCE: 8
gtgaggttta ttcctgctgc gcatcactcg gccggttcga atagtccggt gaaccgggtt     60
gtgattcatg caacatgccc ggatgtgggg tttccgtccg cttcgcgtaa aggacgggcg    120
gtgtctacag cgaactattt cgcgtcccca tcgtcgggcg gttcggcgca ttacgtttgc    180
gatattgggg agacggtgca gtgcctgtca gaggggacta ttgggtggca tgccccgccg    240
aatccgcata gtttgggtat agagatttgc gcggatgggg gttcgcacgc ctcgttccgt    300
gtgccggggc atgcttacac gagggagcag tggcttgatc ctcgcgtgtg gcctgcggtg    360
gagcgtgccg ccatcctgtg tagacgtttg tgtgacaaat ataatgttcc aaagaggaag    420
cttagtgcag ccgatttgaa ggctggcagg cggggtgtgt gtggccatgt ggatgttacg    480
gatgcatggc accagtcgga tcacgatgat ccggggccgt ggtttccgtg ggacaggttt    540
atggccgtcg tgaacggcgg cagtggagag agtgaggagt taacggtggc tgatgtacaa    600
gcgttacata atcagattaa acaattgtct gcccagctta ctggttcggt gaataagctg    660
caccatgatg ttggtgtggt gcaggtgcag aatggtgatt tgggtaaacg tgtggatgcc    720
ctgtcgtggg tgaagaaccc ggtgacgggg aagctgtggc gtactaagga tgctttgtgg    780
agtgtctggt attacgtgct ggagtgtcgc agccgaatag acaggctcga gtctactgtt    840
aacggtttga aaaagtga                                                  858

<210> SEQ ID NO 9
<211> LENGTH: 40
<212> TYPE: DNA
<213> ORGANISM: Bacteriophage PA6

<400> SEQUENCE: 9
cttgtttgat ggttttgtag tagccgacga ggatgcgctg                           40

<210> SEQ ID NO 10
<211> LENGTH: 26
<212> TYPE: DNA
<213> ORGANISM: Bacteriophage PA6

<400> SEQUENCE: 10
agtattgtgc cgccacggcg tagcgg                                          26

<210> SEQ ID NO 11
<211> LENGTH: 57
<212> TYPE: DNA
<213> ORGANISM: Bacteriophage PA6

<400> SEQUENCE: 11
gaaggcgtcc cagcagtatt caataatgtg ttgtagtaca ctatcgggca tgtctcg        57

<210> SEQ ID NO 12
<211> LENGTH: 76
```

```
<212> TYPE: DNA
<213> ORGANISM: Bacteriophage PA6

<400> SEQUENCE: 12
ttcgtcgagc cacgcgtcga caatgatgtt gcgtatggcg cgtttgtctt tggtggtggg    60
tttgaatgcg atgctc                                                    76

<210> SEQ ID NO 13
<211> LENGTH: 379
<212> TYPE: DNA
<213> ORGANISM: Bacteriophage PA6

<400> SEQUENCE: 13
gatggcttct ttcgcccaat aggatgtgcc accgctggtc cagtatccga gtttgttgcg    60
ctgcatgccc ttggcgtcca tctcgtcgat agtgaggcac ctgcggcgat tggggcctgt   120
cttgaccccg tggtcgcctg tccggtgcat gtcgcctgag gtggtactcg tgaatgtttc   180
atggcagatg gtacagtgct ctggtcgata tccggtgatt gtgctatcgc acttgtggca   240
tgtccattcc atgattgctc ctattttcca ttataagact tcctgtagtg ccattttagc   300
gccttgcggg tcttgggggt acaactatat aggtcaggtg tttctaggcg attctaggct   360
cattgtgtgt ggctggggt                                                379
```